United States Patent
Scheidt et al.

(10) Patent No.: US 11,518,750 B2
(45) Date of Patent: Dec. 6, 2022

(54) 3-METHYLIDENEOXAN-4-ONE COMPOUNDS AND SUBSTITUTED DERIVATIVES THEREOF AS INHIBITORS OF TELOMERASE

(71) Applicant: NORTHWESTERN UNIVERSITY, Evanston, IL (US)

(72) Inventors: Karl A. Scheidt, Evanston, IL (US); Rick C. Betori, Gurnee, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 16/986,718

(22) Filed: Aug. 6, 2020

(65) Prior Publication Data
US 2021/0070725 A1    Mar. 11, 2021

Related U.S. Application Data

(60) Provisional application No. 62/883,588, filed on Aug. 6, 2019.

(51) Int. Cl.
*C07D 309/32*    (2006.01)
*C07D 405/06*    (2006.01)

(52) U.S. Cl.
CPC ......... *C07D 309/32* (2013.01); *C07D 405/06* (2013.01)

(58) Field of Classification Search
CPC .......................... C07D 309/32; C07D 405/06
See application file for complete search history.

(56) References Cited

FOREIGN PATENT DOCUMENTS

JP    WO2010/064705    * 10/2010

OTHER PUBLICATIONS

Mueller (Sel. Org. React. Database (SORD) 2005, (Jul. 1, 2014).*
PubChem [Internet], Bethesda (MD): National Library of Medicine (US), National Center for Biotechnology Information; 2004-. PubChem Compound Summary for CID 82277832, 3-Methylideneoxan-4-one. Available from: https://pubchem.ncbi.nlm.nih.gov/compound/3-Methylideneoxan-4-one (Oct. 20, 2014).*
STN/Chemical Abstracts registry No. RN1937361-27-7 (Jun. 23, 2016).*
Betori et al. ((2019): Targeted Covalent Inhibition of Telomerase. ChemRxiv. Preprint) posted on Jul. 23, 2019.*
Shen, Y., et al. (2008) hTERT-targeted RNA interference inhibits tumorigenicity and motility of HCT116 cells, Canc. Biol. Ther. 7, 228-236.
Singer, R. A., et al. (1995) Catalytic, Enantioselective Dienolate Additions to Aldehydes: Preparation of Optically Active Acetoacetate Aldol Adducts, J. Am. Chem. Soc. 117, 12360-12361.

(Continued)

*Primary Examiner* — Valerie Rodriguez-Garcia
(74) *Attorney, Agent, or Firm* — Quarles & Brady LLP

(57) ABSTRACT

Disclosed are 3-methylideneoxan-4-one compounds, derivatives thereof, and methods of their synthesis and methods of their use in treating a disease or disorder in a subject in need thereof, such as diseases and disorders that are associated with telomerase activity such as cancer. The disclosed compounds may be formulated in a pharmaceutical composition for treating diseases and disorders that are associated with telomerase activity such as cancer.

16 Claims, 26 Drawing Sheets

Specification includes a Sequence Listing.

(56) References Cited

OTHER PUBLICATIONS

Singh, J., et al. The resurgence of covalent drugs. Nat. Rev. Drug Discov. 10, 307-317 (2011).
Smith, A. B., et al. Total Synthesis of (−)-Okilactomycin. J. Am. Chem. Soc. 129, 14872-14874 (2007).
Tamakawa, R. A., et al. Telomerase Inhibition Potentiates the Effects of Genotoxic Agents in Breast and Colorectal Cancer Cells in a Cell Cycle-Specific Manner. Cancer research 70, 8684-8694 (2010).
Tenenbaum, J. M., et al. Synthesis of (−)-Okilactomycin by a Prins-Type Fragment-Assembly Strategy. Angew. Chem. Int. Ed. 50, 5892-5895 (2011).
Thomford, E. N., et al. (2018) Natural Products for Drug Discovery in the 21st Century: Innovations for Novel Drug Discovery, Int. J. Mol. Sci. 19.
Toledo Warshaviak, D., et al. (2014) Structure-Based Virtual Screening Approach for Discovery of Covalently Bound Ligands, J. Chem. Inf. Mod. 54, 1941-1950.
Tomlinson, C. G., et al. Quantitative assays for measuring human telomerase activity and DNA binding properties. Methods 114, 85-95 (2017).
Ward, R. A., et al. (2013) Structure- and Reactivity-Based Development of Covalent Inhibitors of the Activating and Gatekeeper Mutant Forms of the Epidermal Growth Factor Receptor (EGFR), J. Med. Chem. 56, 7025-7048.
Zhu, K., et al. (2014) Docking covalent inhibitors: a parameter free approach to pose prediction and scoring, J Chem Inf Model 54, 1932-1940.
Zuhl, A. M., et al. (2012) Competitive Activity-Based Protein Profiling Identifies Aza-ß-Lactams as a Versatile Chemotype for Serine Hydrolase Inhibition, J. Am. Chem. Soc. 134, 5068-5071.
Ahn, K., et al. (2007) Novel Mechanistic Class of Fatty Acid Amide Hydrolase Inhibitors with Remarkable Selectivity, Biochemistry 46, 13019-13030.
Arndt, G. M., et al. (2016) New prospects for targeting telomerase beyond the telomere, Nat. Rev. Canc. 16, 508.
Bachovchin, D. A., et al. (2010) Superfamily-wide portrait of serine hydrolase inhibition achieved by library-versus-library screening, Proc. Natl. Acad. Sci. U.S.A. 107, 20941.
Beattie, T. L., et al. (1998) Reconstitution of human telomerase activity in vitro, Curr. Biol. 8, 177-180.
Bermudez, Y., et al. (2006) Telomerase confers resistance to caspase-mediated apoptosis, Clin Interv Aging 1, 155-167.
Betori, R. C., et al. "Targeted Covalent Inhibition of Telomerase." ACS chemical biology 15.3 (Published online Feb. 4, 2020): 706-717.
Betori, R. C., et al. A Biocatalytic Route to Highly Enantioenriched ß-Hydroxydioxinones. Adv. Synth. Catal. 359, 1131-1137 (2017).
Bryan, T. M., et al. Telomere elongation in immortal human cells without detectable telomerase activity. The EMBO journal 14, 4240-4248 (1995).
Burger, A. M., et al. (2005) The G-Quadruplex-Interactive Molecule BRACO-19 Inhibits Tumor Growth, Consistent with Telomere Targeting and Interference with Telomerase Function, Cancer Res. 65, 1489.
Choi, S.-H., et al. (2005) Inhibitory effects of costunolide on the telomerase activity in human breast carcinoma cells, Cancer Lett. 227, 153-162.
Cohen, S. B. et al. A sensitive direct human telomerase activity assay. Nature Methods 5, 355 (2008).
Cohen, S. B. et al. Protein Composition of Catalytically Active Human Telomerase from Immortal Cells. Science 315, 1850-1853 (2007).
Crane, E. A., et al. (2010) Prins-Type Macrocyclizations as an Efficient Ring-Closing Strategy in Natural Product Synthesis, Angew Chem Int Edit 49, 8316-8326.
Crane, E. A., et al. Enantioselective Synthesis of (−)-Exiguolide by Iterative Stereoselective Dioxinone-Directed Prins Cyclizations. Angew. Chem. Int. Ed. 50, 9112-9115 (2011).

Custar, D. W., et al. Total Synthesis and Structural Revision of the Marine Macrolide Neopeltolide. J. Am. Chem. Soc. 130, 804-805 (2008).
Custar, D. W., et al. Total Synthesis and Structure-Activity Investigation of the Marine Natural Product Neopeltolide. J. Am. Chem. Soc. 131, 12406-12414 (2009).
Damm, K. et al. A highly selective telomerase inhibitor limiting human cancer cell proliferation. The EMBO Journal 20, 6958 (2001).
De Cian, A. et al. Reevaluation of telomerase inhibition by quadruplex ligands and their mechanisms of action. Proc. Natl. Acad. Sci. USA 104, 17347-17352 (2007).
De Lange, T. (2005) Shelterin: the protein complex that shapes and safeguards human telomeres, Genes Dev 19, 2100-2110.
De Lange, T. (2018) Shelterin-Mediated Telomere Protection, Annu. Rev. Genet. 52, 223-247.
Efimova, E. V. et al. Poly(ADP-Ribose) Polymerase Inhibitor Induces Accelerated Senescence in Irradiated Breast Cancer Cells and Tumors. Cancer Research 70, 6277-6282 (2010).
El-Daly, H., et al. (2005) Selective cytotoxicity and telomere damage in leukemia cells using the telomerase inhibitor BIBR1532, Blood 105, 1742-1749.
Feng, J. et al. The RNA component of human telomerase. Science 269, 1236 (1995).
Flanagan, M. E., et al. (2014) Chemical and Computational Methods for the Characterization of Covalent Reactive Groups for the Prospective Design of Irreversible Inhibitors, J. Med. Chem. 57, 10072-10079.
Ganesan, K., et al. (2018) Telomerase Inhibitors from Natural Products and Their Anticancer Potential, Int. J. Mol. Sci. 19, 1-26.
Ghosh, A. et al. Telomerase directly regulates NF-?B-dependent transcription. Nat. Cell Biol. 14, 1270 (2012).
Gillis, A. J., et al. Structure of the Tribolium castaneum telomerase catalytic subunit TERT. Nature 455, 633-636 (2008).
Hahn, W. C. et al. Inhibition of telomerase limits the growth of human cancer cells. Nat. Med. 5, 1164-1170 (1999).
Herbert, B. S. et al. Inhibition of human telomerase in immortal human cells leads to progressive telomere shortening and cell death. Proceedings of the National Academy of Sciences 96, 14276 (1999).
Huang, P.-R., et al. (2005) Potent inhibition of human telomerase by helenalin, Cancer Lett. 227, 169-174.
Johnson, D. S., et al. Strategies for discovering and derisking covalent, irreversible enzyme inhibitors. Future Med. Chem. 2, 949-964 (2010).
Kaschani, F., et al. (2012) Selective inhibition of plant serine hydrolases by agrochemicals revealed by competitive ABPP, Biorg. Med. Chem. 20, 597-600.
Kathman, S. G., et al. (2014) A Fragment-Based Method to Discover Irreversible Covalent Inhibitors of Cysteine Proteases, J. Med. Chem. 57, 4969-4974.
Kim, M.-Y., et al. (2002) Telomestatin, a Potent Telomerase Inhibitor That Interacts Quite Specifically with the Human Telomeric Intramolecular G-Quadruplex, J. Am. Chem. Soc. 124, 2098-2099.
Kuhn, B., et al. (2004) Prediction of pKa shifts in proteins using a combination of molecular mechanical and continuum solvent calculations, J. Comput. Chem. 25, 1865-1872.
Leung, D., et al. (2003) Discovering potent and selective reversible inhibitors of enzymes in complex proteomes, Nat. Biotechnol. 21, 687-691.
McDonald, B. R. et al. Pyranone Natural Products as Inspirations for Catalytic Reaction Discovery and Development. Acc. Chem. Res. 48, 1172-1183 (2015).
Mender, I., et al. (2015) Induction of Telomere Dysfunction Mediated by the Telomerase Substrate Precursor 6-Thio-2'-Deoxyguanosine, Cancer Disc. 5, 82.
Mitchell, M., et al. Structural basis for telomerase catalytic subunit TERT binding to RNA template and telomeric DNA. Nat. Struct. Mol. Biol. 17, 513 (2010).
Morris et al., "Stereoselective Synthesis of Tetrahydropyran-4-ones from Dioxinones Catalyzed by Scandium(III) Triflate," Org. Lett. 2005, vol. 7, No. 6, 1113-1116.

(56) References Cited

OTHER PUBLICATIONS

Mueller, S., et al. (2007) Targeting telomerase activity by BIBR1532 as a therapeutic approach in germ cell tumors, Invest New Drug 25, 519-524.

Naasani, I., et al. (1998) Telomerase inhibition, telomere shortening, and senescence of cancer cells by tea catechins, Biochem. Biophys. Res. Commun. 249, 391-396.

Nakai, R. et al. Telomerase Inhibitors Identified by a Forward Chemical Genetics Approach Using a Yeast Strain with Shortened Telomere Length. Chemistry & Biology 13, 183-190 (2006).

Neidle, S. (2010) Human telomeric G-quadruplex: The current status of telomeric G-quadruplexes as therapeutic targets in human cancer, FEBS Journal 277, 1118-1125.

Ouellette, M. M., et al. (2011) Targeting telomerase-expressing cancer cells, J. Cell. Mol. Med. 15, 1433-1442.

Pascolo, E. et al. Mechanism of Human Telomerase Inhibition by BIBR1532, a Synthetic, Non-nucleosidic Drug Candidate. J. Biol. Chem. 277, 15566-15572 (2002).

Rezler, E. M., et al. Telomeres and telomerases as drug targets. Curr. Opin. Pharmacol. 2, 415-423 (2002).

Roth, A., et al. Imetelstat (GRN163L)—Telomerase-Based Cancer Therapy. Small Molecules in Oncology 184, 221-234 (2010).

Seimiya, H., et al. (2002) Telomere shortening and growth inhibition of human cancer cells by novel synthetic telomerase inhibitors MST-312, MST-295, and MST-1991, Mol Cancer Ther 1, 657-665.

Sekaran, V., et al. Telomere maintenance as a target for drug discovery. J. Med. Chem 57, 521-538 (2014).

\* cited by examiner

B)

D)

| TRAP:Lysate | |
|---|---|
| Cell Line | $IC_{50}$ |
| A549 | 145 nM |
| MCF-7 | 90 nM |
| HeLa | 125 nM |
| MDA-MB-231 | 110 nM |
| ACHN | 95 nM |

E)

| TRAP:Cell | |
|---|---|
| Cell Line | $IC_{50}$ |
| A549 | 284 nM |
| MCF-7 | 270 nM |
| HeLa | 340 nM |
| MDA-MB-231 | 290 nM |
| ACHN | 380 nM |

| Cell Viability Panel | |
|---|---|
| Telomerase Positive Cell Line | IC$_{50}$ |
| A549 | 21 μM |
| MCF-7 | 35 μM |
| HeLa | 29 μM |
| MDA-MB-231 | 19 μM |
| ACHN | 34 μM |

| Cell Viability Panel | |
|---|---|
| Telomerase Negative Cell Line | IC$_{50}$ |
| Saos-2 | ND |
| WI-38 VA-13 | ND |

Cell Viability-Washout

| Condition | IC$_{50}$ |
|---|---|
| No Washout | 23 μM |
| 2 h | 27 μM |
| 4 h | 32 μM |
| 8 h | 35 μM |
| 12 h | 35 μM |
| 24 h | 41 μM |

| Telomerase Inhibition-Washout | |
|---|---|
| Condition | IC$_{50}$ |
| 2 h | 370 nM |
| 4 h | 360 nM |
| 8 h | 380 nM |
| 12 h | 410 nM |
| 24 h | 440 nM |

| No Covalent Telomerase Inhibitors | |
|---|---|
| Inhibitor | IC$_{50}$ |
| BIBR1532 | ND |
| MST-312 | ND |
| NU-1 | 360 nM |

3-METHYLIDENEOXAN-4-ONE COMPOUNDS AND SUBSTITUTED DERIVATIVES THEREOF AS INHIBITORS OF TELOMERASE

CROSS-REFERENCED TO RELATED PATENT APPLICATIONS

This application claims the benefit of priority under 35 U.S.C. § 119(e) to U.S. Provisional Application No. 62/883,588, filed on Aug. 6, 2019, the content of which is incorporated herein by reference in its entirety.

REFERENCE TO A SEQUENCE LISTING SUBMITTED VIA EFS-WEB

The content of the ASCII text file of the sequence listing named "702581 01801 ST25.txt" which is 1.91 kb in size was created on Nov. 13, 2020 and electronically submitted via EFS-Web herewith the application is incorporated herein by reference in its entirety.

FIELD

The field of the invention relates to 3-methylideneoxan-4-one compounds, derivatives thereof, and their use as inhibitors of telomerase. In particular, the field of the invention relates to 3-methylideneoxan-4-one compounds, derivatives thereof, and their use for treating cancers that are associated with telomerase activity.

BACKGROUND

The ends of chromosomes in human cells are capped by telomeres, 5- to 10-kb tandem arrays of 5'-TTAGGG-3' sequence/that, with the cognate six-protein shelterin complex,[2,3] protect chromosome ends against recognition as DNA damage. As telomeres progressively shorten with each cell division cycle, one or more may reach a critical length. The resulting DNA damage response blocks further proliferation and promotes apoptosis or cellular senescence.[4-6] Stem cells, embryonic cells, and germ cells overcome this proliferation limit by expressing telomerase, a ribonucleoprotein (RNP) complex that counteracts telomere shortening by synthesizing TTAGGG repeats at chromosome 3' ends.[7-9] The human telomerase core is composed of an RNA-dependent DNA polymerase, the human telomerase reverse transcriptase (hTERT),[10,11] and the human telomerase RNA (hTR)[12-14] which serves as the template for telomere repeat synthesis. Telomerase binds to the 3' single-strand telomeric overhang, aligning with the complementary sequence found on hTR, priming the DNA for nucleotide addition catalyzed by hTERT (FIG. 1A). Following nucleotide addition the RNA template translocates by six nucleotides relative to the catalytic center to promote an additional round of nucleotide addition. While hTR is broadly expressed, hTERT is normally silenced in somatic cells, although it is detectable in certain proliferating cells, stem cells and germ cells.[15] Reactivation of hTERT is observed in ~90% of human malignancies and has been directly linked to cancer cell immortality, making hTERT a compelling target for inhibition.[16] In addition to telomere maintenance, genetic studies of hTERT have identified multiple extra-telomeric activities that may promote malignancy including deregulation of oncogenic signaling pathways,[17,18] resistance to apoptosis[19,20], enhanced DNA repair[21-23] and promotion of telomere protective complexes.[24]

In recent decades, diverse strategies have been pursued to target telomerase in cancer,[25-29] including the non-competitive small-molecule inhibitor BIBR1532,[30-33] antisense oligonucleotide hTR binders such as imetelstat,[34] and G-quadruplex stabilizers designed to block telomerase from extending telomeres.[35-39] Moreover, nature has provided numerous unique scaffolds that have been proposed to inhibit telomerase activity[40] such as epigallocatechin gallate,[41,42] helenalin[43] and costunolide[44] (FIG. 1B). While nature serves as valuable information for the design of therapeutics and chemical probes, their implementation as tools to study biological processes is often limited by their isolation or synthesis.[45-47] Overall, these agents have contributed significantly to our understanding of telomerase and telomere biology, yet fail to provide a means to covalently and irreversibly block telomerase activity, a unique inhibitory mechanism that may provide further insight into the biological functions of telomerase. Despite concerns of off-target reactivity, small-molecule covalent inhibitors can have clear advantages over non-covalent therapeutics.[48,49] Their irreversible inhibition decreases dependence on affinity or drug levels and can raise the barrier to drug resistance.[50] The clinical success of ibrutinib,[51] a first-generation covalent inhibitor of Bruton's tyrosine kinase, has led to multiple second generation investigational agents with increased specificity, establishing the value of combining rational compound design and proteomic validation to accelerate development of targeted covalent inhibitors. Therefore, our goal was to design and develop natural product-inspired, synthetically accessible covalent inhibitors of telomerase as new tools to study the telomeric functions of human telomerase (FIG. 1C).

SUMMARY

Disclosed are 3-methylideneoxan-4-one compounds, derivatives thereof, and methods of their synthesis and methods of their use in treating a disease or disorder in a subject in need thereof, such as diseases and disorders that are associated with telomerase activity such as cancer. The disclosed compounds may be formulated in a pharmaceutical composition for treating diseases and disorders that are associated with telomerase activity such as cancer.

Also disclosed are pharmaceutical compositions that comprise the disclosed compounds with a carrier, diluent, or excipient. The pharmaceutical compositions may comprise an effective amount of the compounds (or salts thereof) for treating or preventing a disease or disorder that this associated with telomerase activity, such as cell proliferative diseases and disorders such as cancers.

Also disclosed are methods of treating or preventing one of the aforementioned diseases or disorders that include administering the disclosed compounds in an effective amount to a subject in need thereof in order to treat or prevent the disease or disorder. For example, the compound may be formulated in a pharmaceutical composition and administered to a patient having or suspected of having a disease or disorder that this associated with telomerase activity, such as cell proliferative diseases and disorders such as cancers.

BRIEF DESCRIPTION OF THE FIGURES

FIG. 5: A) Cell viability measurement of NU-1 in telomerase positive and negative cell lines. B) Different time points for cell viability-washout experiments. C) Different time points for TRAP-washout experiments. D) Washout experiments with non-covalent telomerase inhibitors.

DETAILED DESCRIPTION

Figure 1:
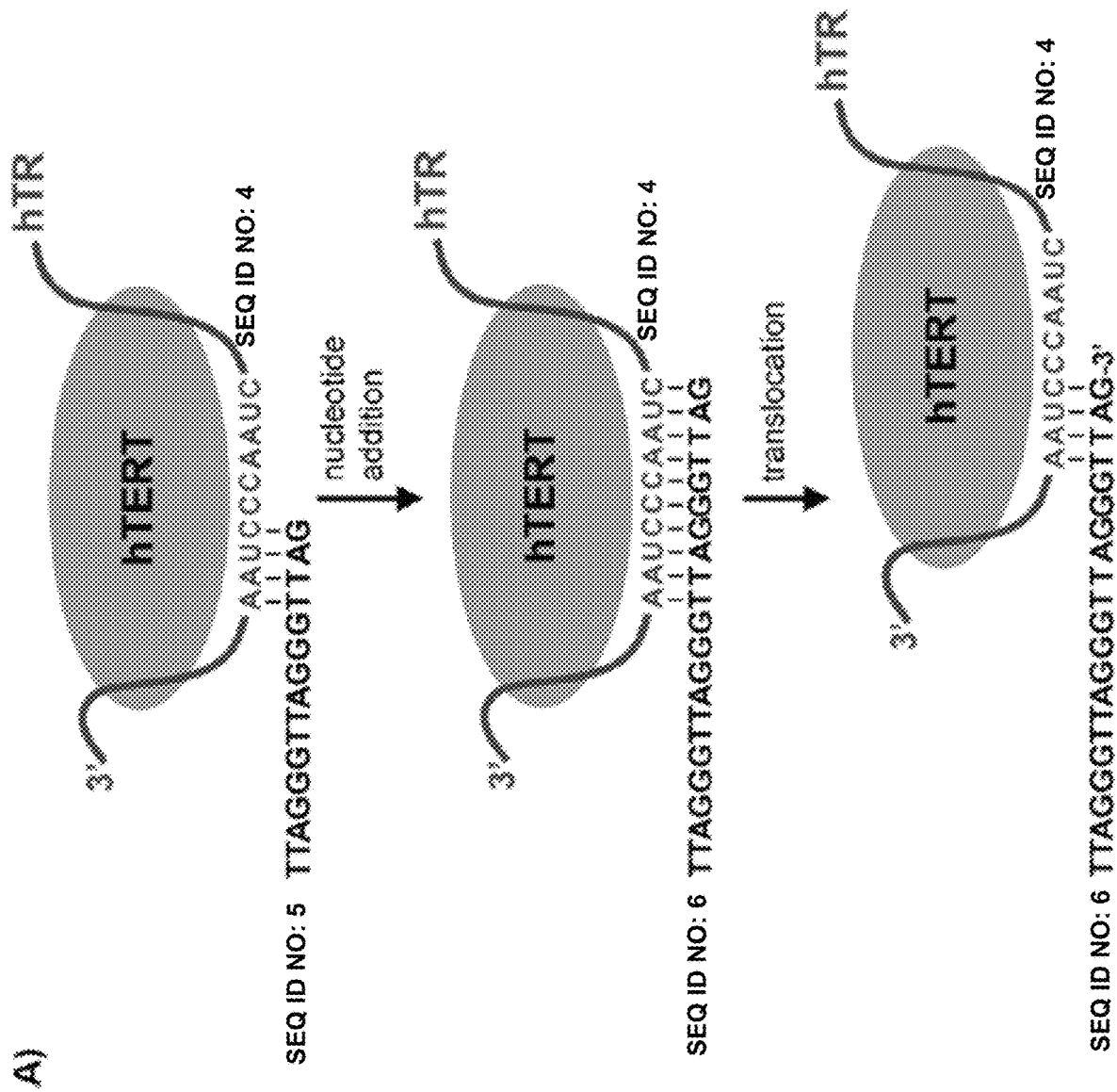
FIG. 1: A) Telomere extension by telomerase. B) Natural products postulated to inhibit telomerase activity through a covalent mechanism. C) Workflow for rational design of chrolactomycin inspired chemical probes.
Figure 1:
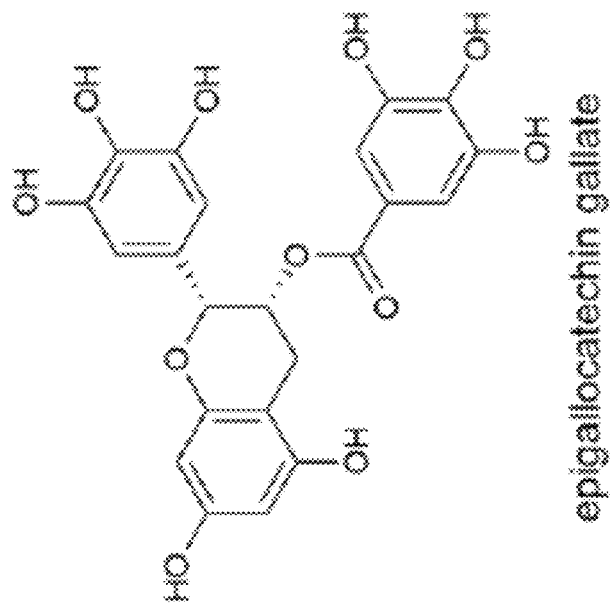
Figure 1:
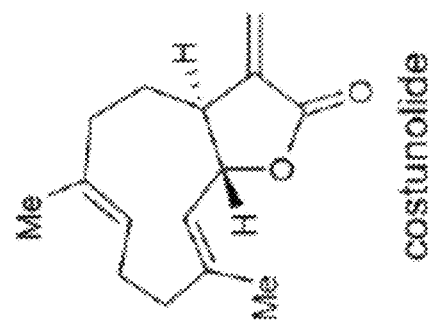
Figure 1:
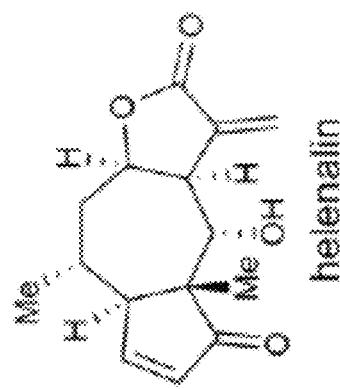
Figure 1:
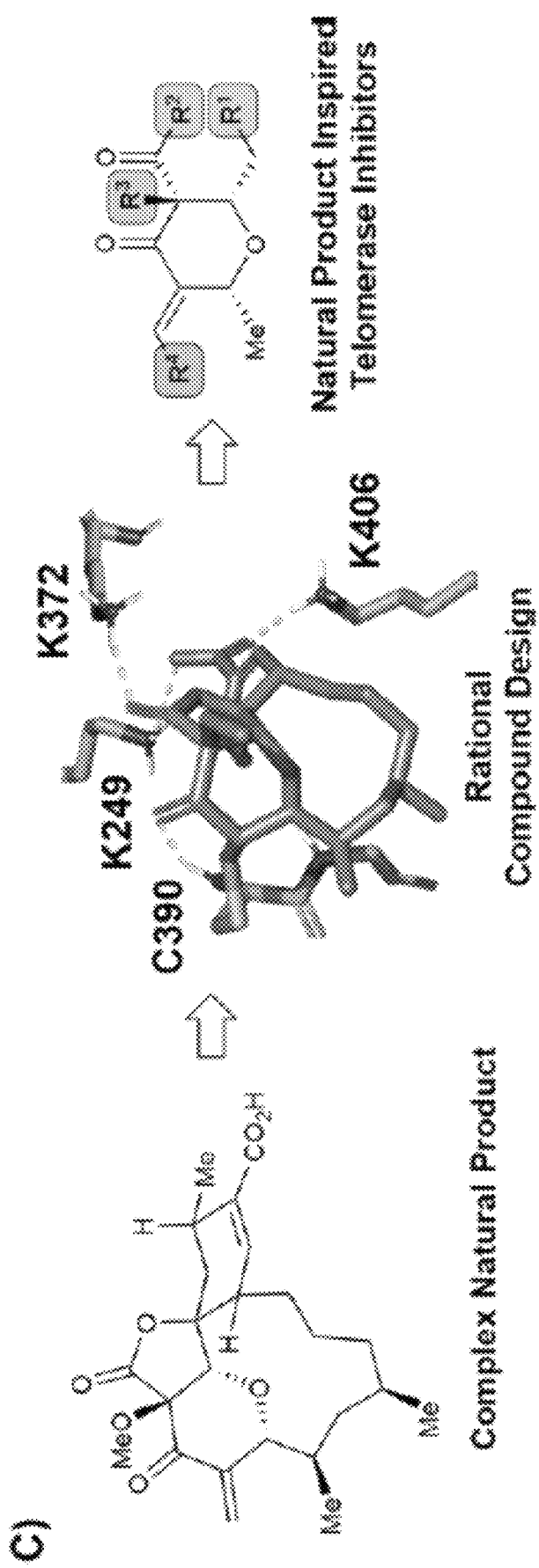

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein refers to a subject in need of treatment for a disease or disorder associated with a compound(s) disclosed herein, such as s-methylideneoxan-4-one compounds and derivatives thereof. The term "subject" may be used interchangeably with the terms "individual" and "patient" and includes human and non-human mammalian subjects. A "subject in need thereof" may include a subject having a disease or disorder that is associated with telomerase activity. A "subject in need thereof" may include a subject having a cell proliferative disease or disorder such as cancer.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —$CH_2$—, —$CH_2CH_2$—, —$CH_2CH_2CH_2$—, —$CH(CH_3)CH_2$—, —$CH_2CH(CH_3)CH_2$—, —$CH(CH_2CH_3)CH_2$—, and the like.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds..

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Pharmaceutical Compositions and Formulations

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates the telomerase activity may be administered as a single compound or in combination with another compound that modulates telomerase activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with telomerase activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating one or more of the aforementioned diseases or disorders.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

3-Methylideneoxan-4-one Compounds and Substituted Derivatives Thereof as Inhibitors of Telomerase The subject matter disclosed herein relates to 3-methylideneoxan-4-one compounds, derivatives thereof, and methods of their synthesis and methods of their use in treating a disease or disorder in a subject in need thereof, such as diseases and disorders that are associated with telomerase activity such as cancer. The disclosed compounds may be formulated in a pharmaceutical composition for treating diseases and disorders that are associated with telomerase activity such as cancer.

In some embodiments, the disclosed compounds have one of the following formulas or a salt or hydrate thereof:

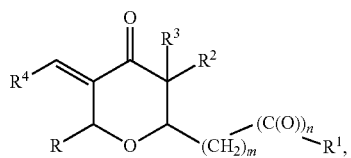

which is a keto form of the disclosed compounds

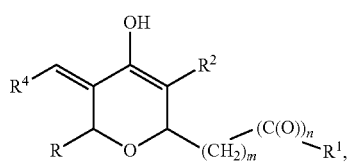

and
which is an enol form of the disclosed compounds,
where:
R is selected from hydrogen, alkyl (e.g., methyl, propyl, isopropyl, n-butyl, or isobutyl), cycloalkyl (e.g., cyclohexyl), aryl (e.g., phenyl), alkyl(aryl) (e.g., benzyl), and R is optionally substituted at one or more positions with halo;
m is selected from 0-3;
n is 0 or 1;

$R^1$ is selected from hydrogen, alkyl, cycloalkyl, aryl, arylalkyl(aryl) (e.g., benzyl), aldehyde, carboxyalkyl, alkynyl; or $R^1$ has a formula selected from —NH-aryl, —N-diaryl, or —NH-aryl(aryl), optionally wherein aryl is selected from phenyl (e.g., wherein $R^1$ is selected from —NH-phenyl, —N— diphenyl, or —NH-benzyl) or fluorenyl (e.g., wherein $R^1$ is —NH-fluoren-9-yl) and optionally wherein $R^1$ is substituted at one or more positions with alkyl (e.g., methyl), alkoxy (e.g., methoxy), hydroxyl, halo (e.g., F, Cl, or Br), and haloalkyl (e.g., trifluoromethyl); or $R^1$ has a formula selected from

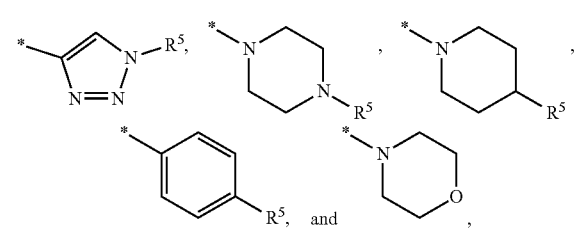

wherein $R^5$ is selected from hydrogen, alkyl, or benzyl, or $R^5$ has a formula selected from —C(O)—NH$_2$, —C(O)—NH-alkyl (e.g., —C(O)—NH—CH$_3$), —C(O)-phenyl, —C(O)—NH— phenyl, —C(O)—NH-benzyl, —CH$_2$—NH-phenyl, —NH—C(O)-phenyl, —N-alkyl-cycloalkyl, —O-phenyl, —O-benzyl, and $R^5$ optionally is substituted at one or more positions with alkyl (e.g., methyl), alkoxy (e.g., methoxy), hydroxyl, halo (e.g., F, Cl, or Br), and haloalkyl (e.g., trifluoromethyl), for example, wherein $R^5$ is substituted at one or more positions of a phenyl group;

$R^2$ is selected from hydrogen, alkyl, alky(aryl) (e.g., benzyl), carbonyl, carboxyl, and and —C(O)—O—$R^6$, wherein $R^6$ is selected from alkyl, cycloalkyl, alkyl(cycloalkyl), aryl, alkyl(aryl), and alkyl(alkoxy) (e.g., where $R^2$ is —C(O)—O-methyl, —C(O)—O-isopropyl, or —C(O)—O-benzyl);

$R^3$ is hydrogen or alkyl (e.g., methyl);

$R^4$ is hydrogen or alkyl (e.g., methyl);

optionally, wherein at least one of R, $R^1$, $R^2$, $R^3$, and $R^4$ is not hydrogen.

In some embodiments of the disclosed compounds R is alkyl which may be straight chain or branched alkyl. In some embodiments, R is selected from: —CH$_3$, —CH$_2$—CH(CH$_3$)$_2$, and —CH$_2$—CH$_2$-phenyl.

In some embodiments, $R^1$ may be selected from:

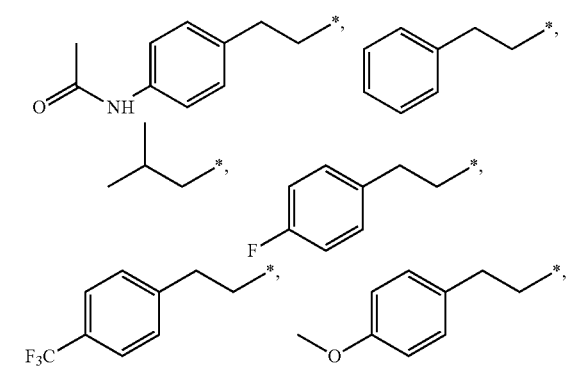

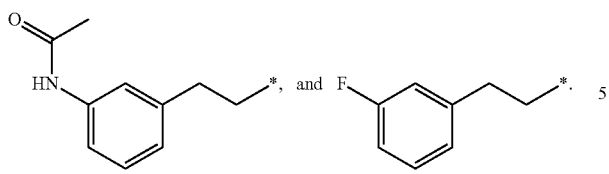

In further embodiments, $R^1$ is

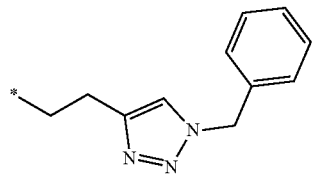 [SMILES: *CCc1cn(Cc2ccccc2)nn1]

and $R^1$ optionally is substituted at one or more positions with halo, for example where $R^1$ includes a halo substituted phenyl moiety.

In some embodiments, R2 includes an ester linkage. In some embodiments, R2 is selected from: —C(O)—O—CH$_3$, —C(O)—O—CH(CH$_3$)$_2$, —C(O)—O—(CH$_2$)$_3$—CH$_3$,

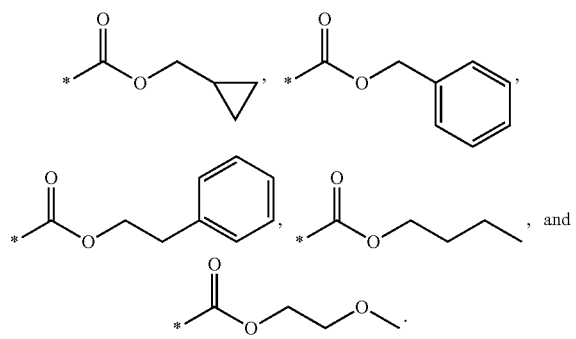

In some embodiments, $R^3$ is alkyl. In some embodiments, $R^3$ is selected from: —CH$_3$, —CH$_2$—CH$_3$, and —CH(CH$_3$)$_2$.

In some embodiments, the disclosed compounds may have a formula selected from:

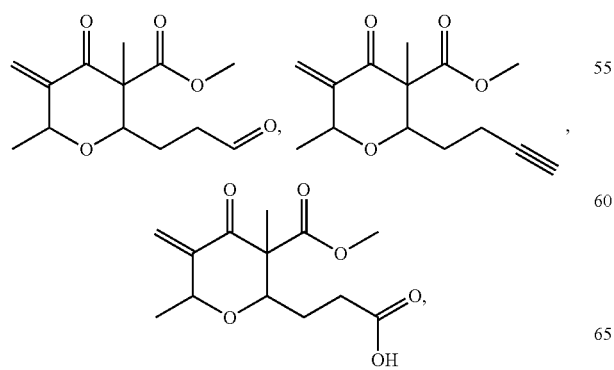

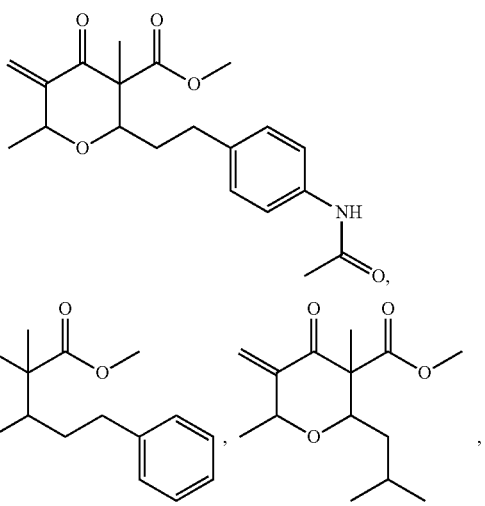

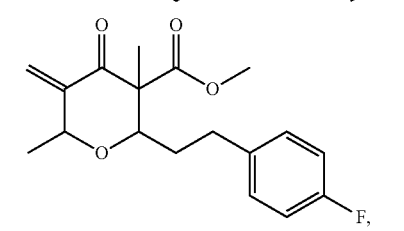

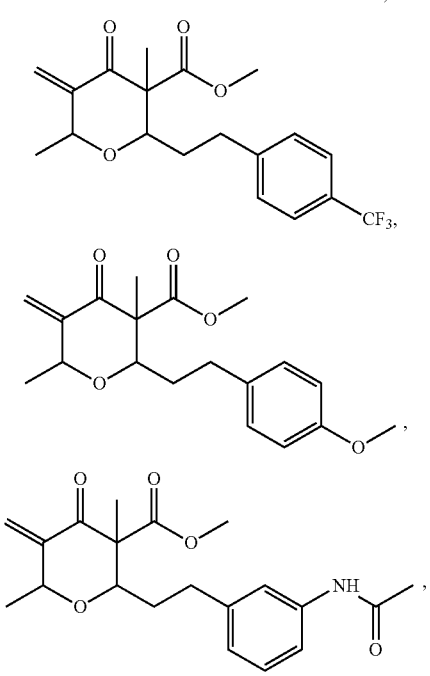

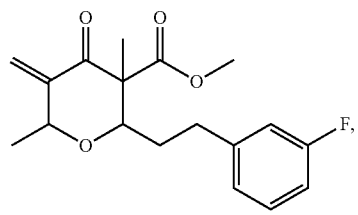

-continued
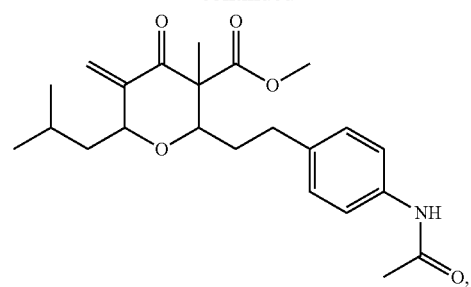
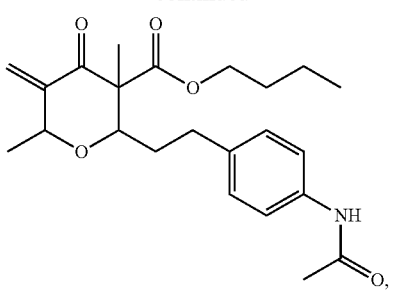
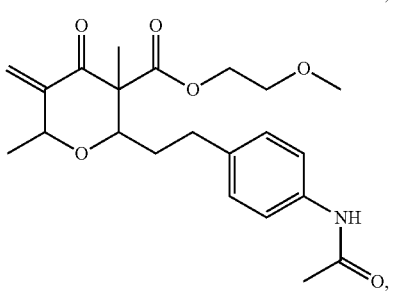
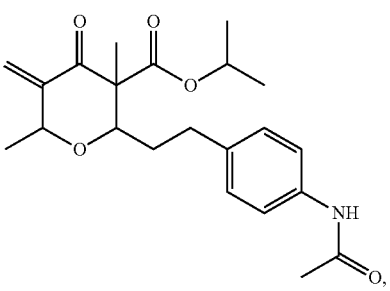
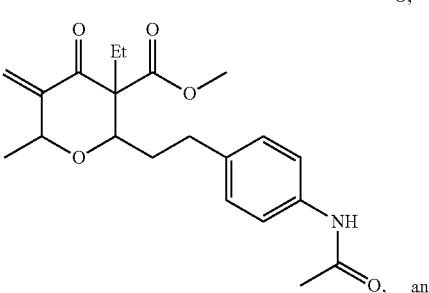
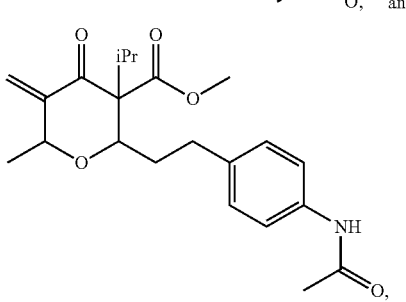, and
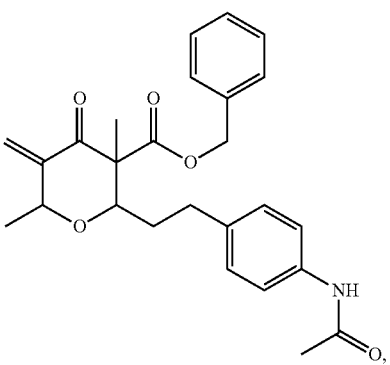
In further embodiments, the compound has a formula selected from:
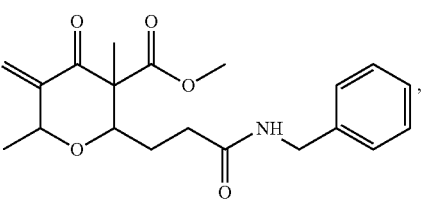
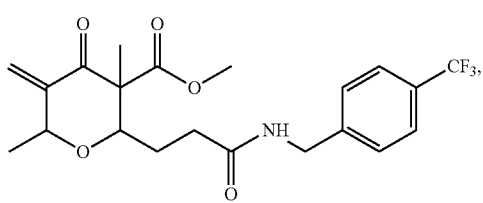

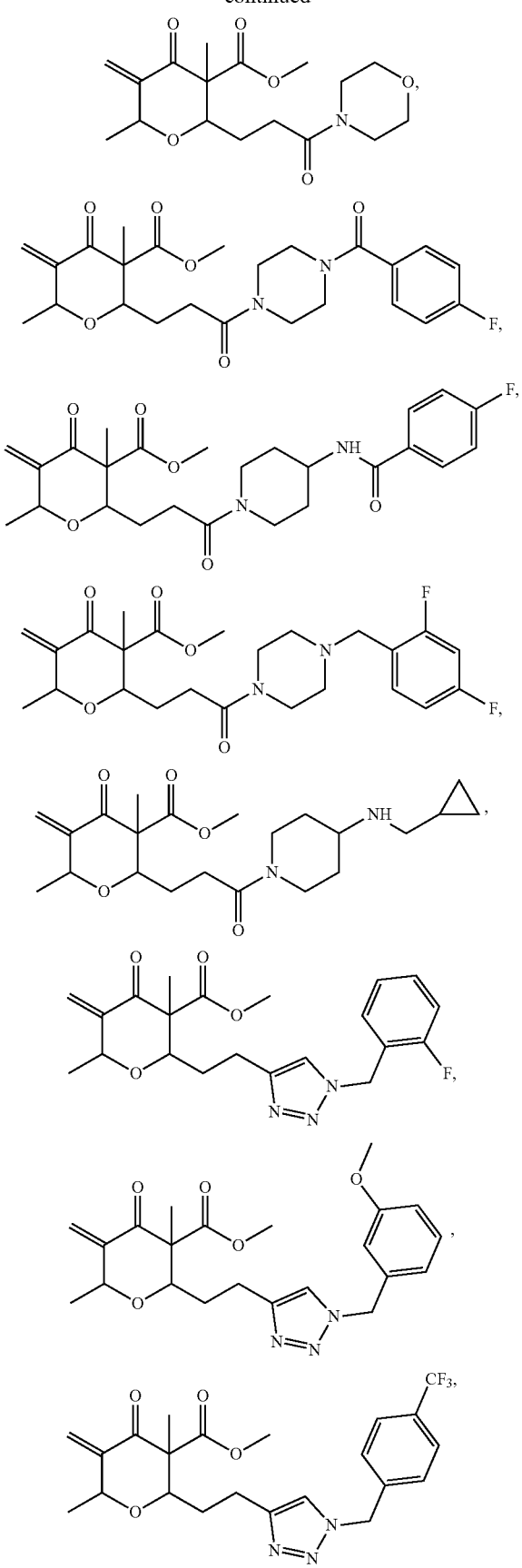
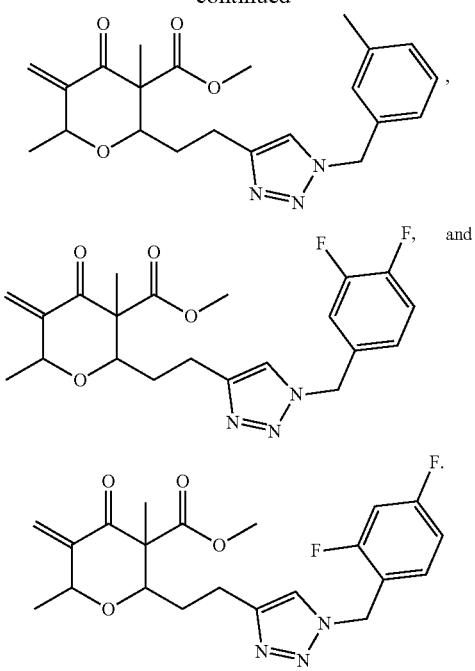
The disclosed compounds may include specific stereoisomers or enantiomers. In some embodiments, the disclosed compounds have a formula selected from:
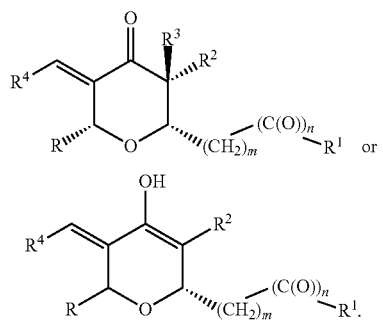
In some embodiments, the disclosed compounds may be selected from:
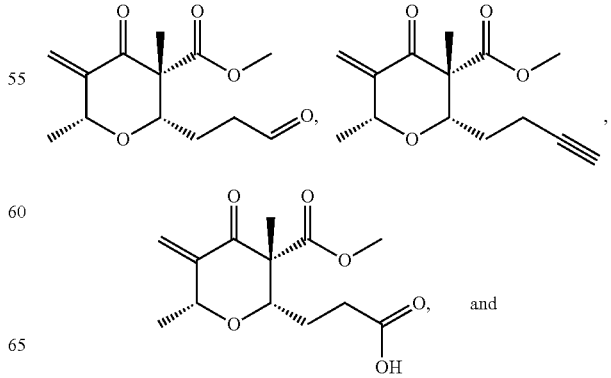

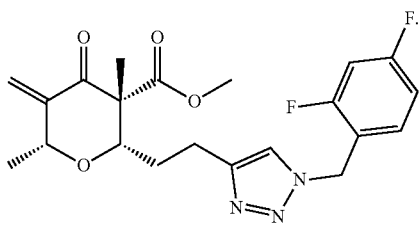
In further embodiments, the disclosed compounds may be selected from
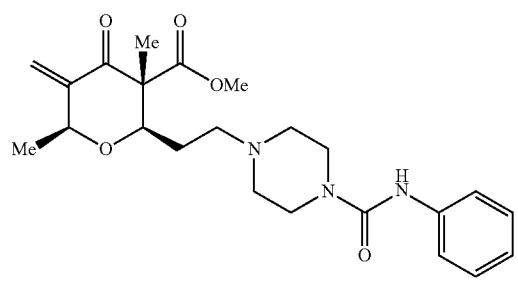
,
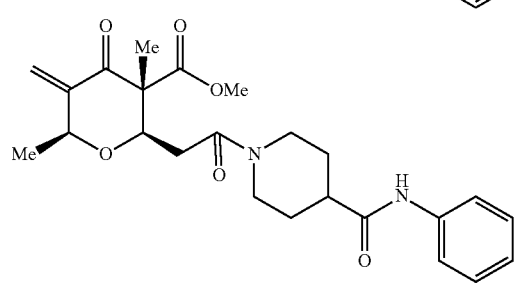
,
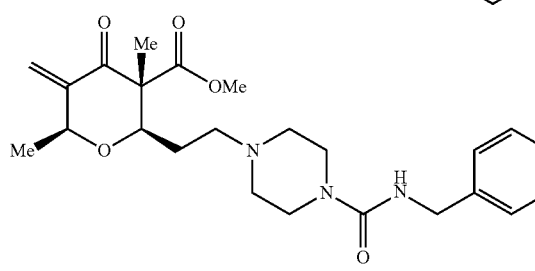
,
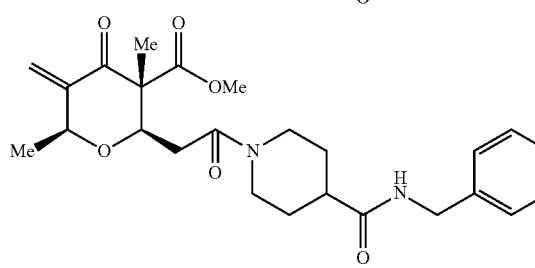
,
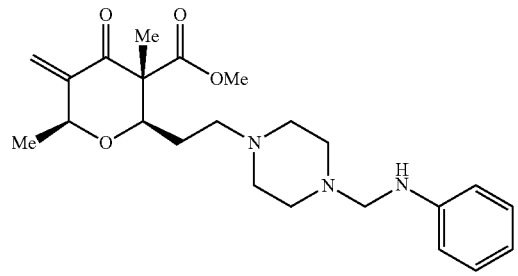
,
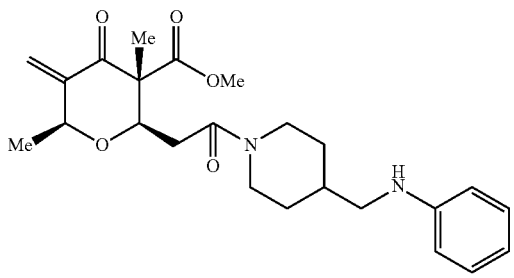
,
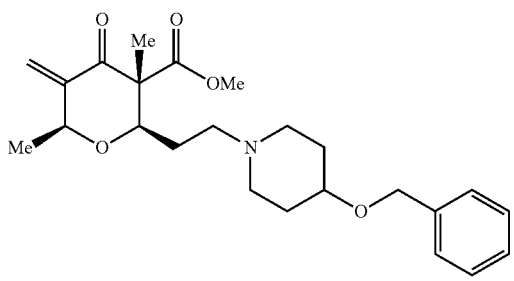
,
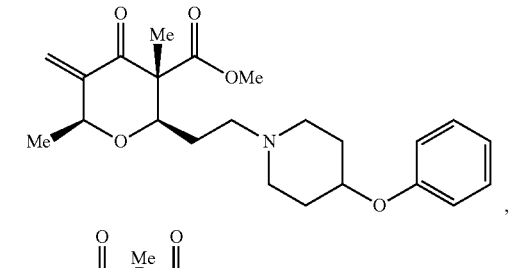
,
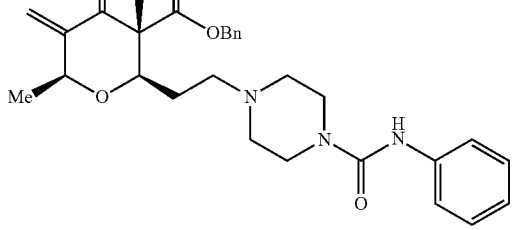
,
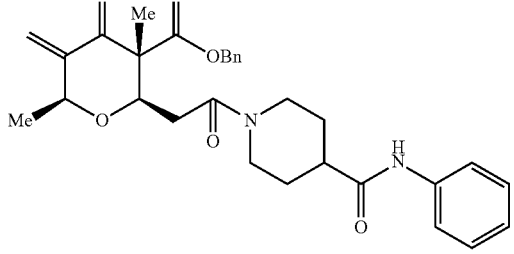
,
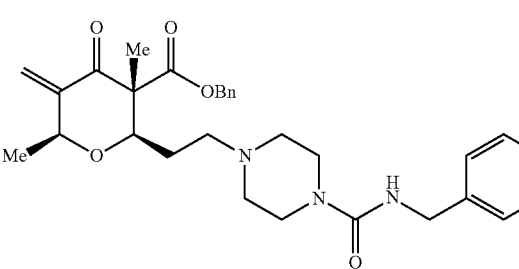
,

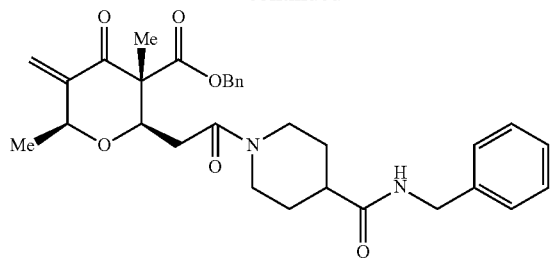
,
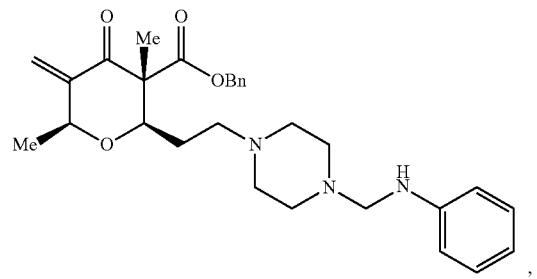
,
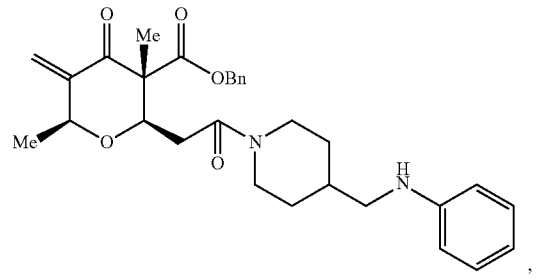
,
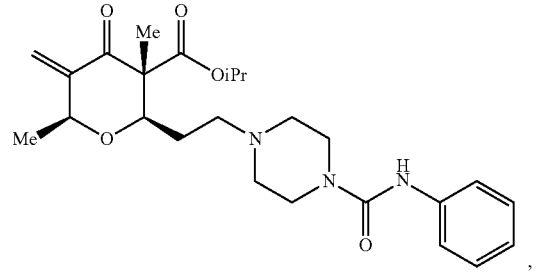
,
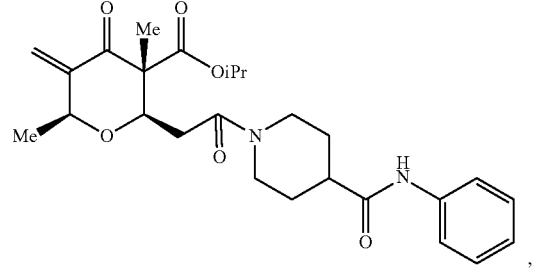
,
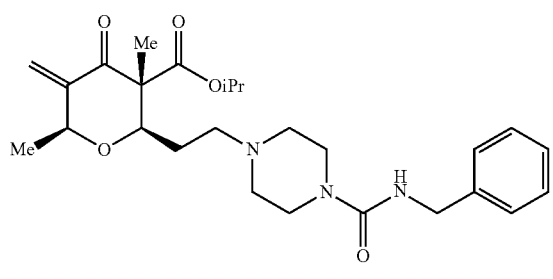
,
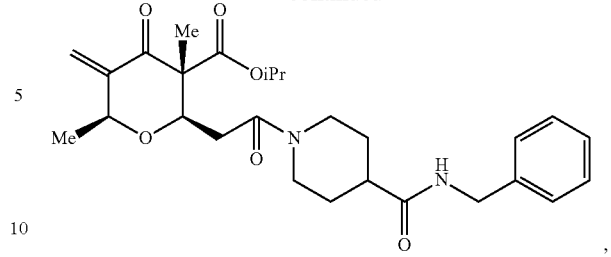
,
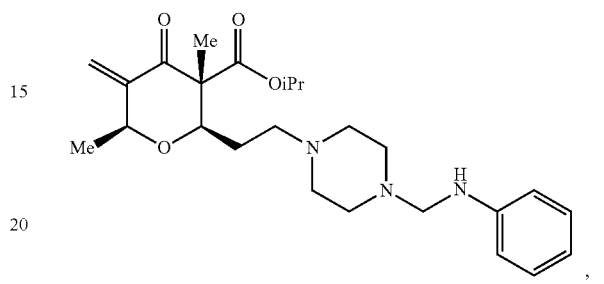
,
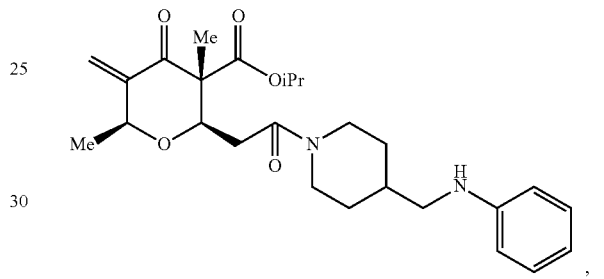
,
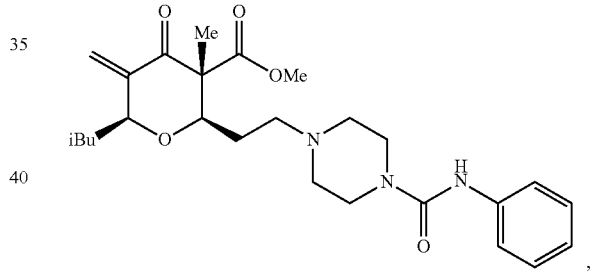
,
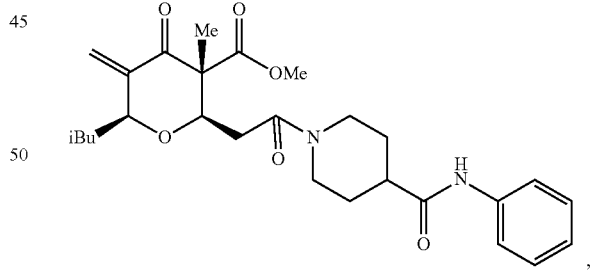
,
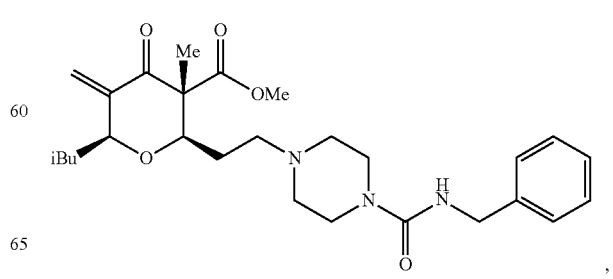
, 23
-continued
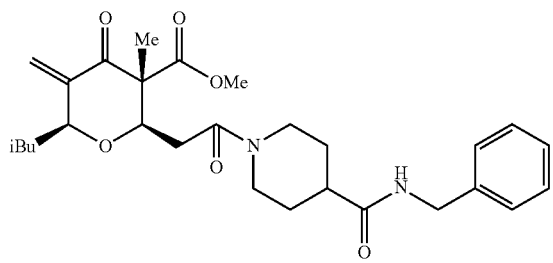
,
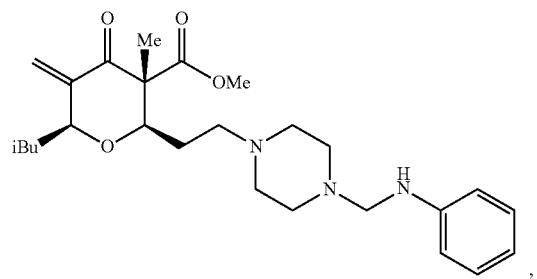
,
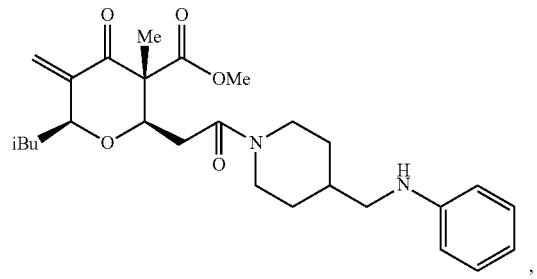
,
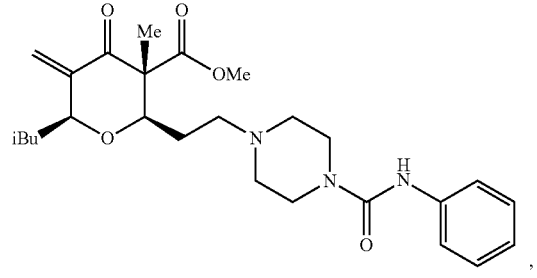
,
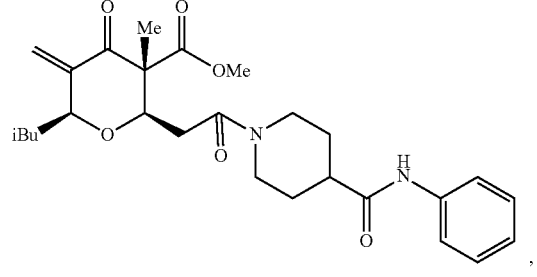
,
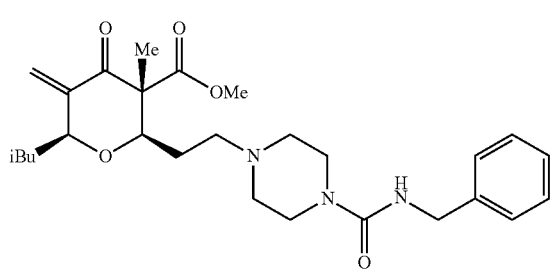
,
24
-continued
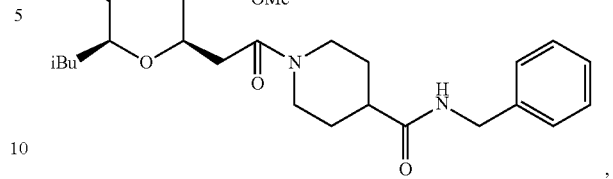
,
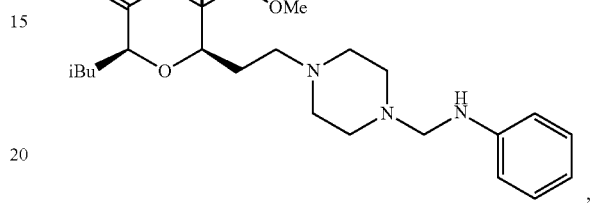
,
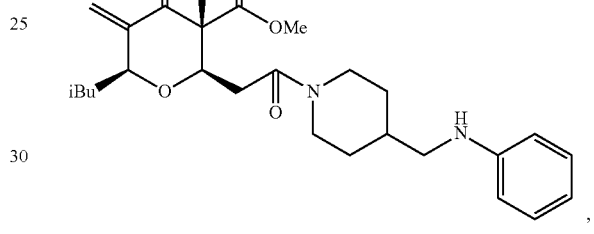
,
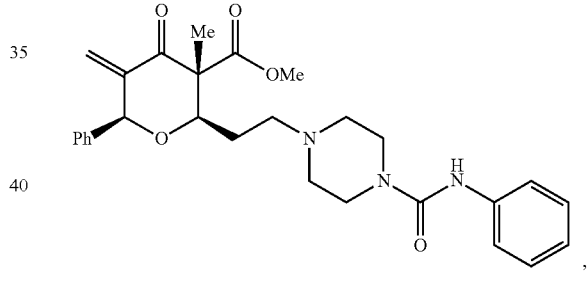
,
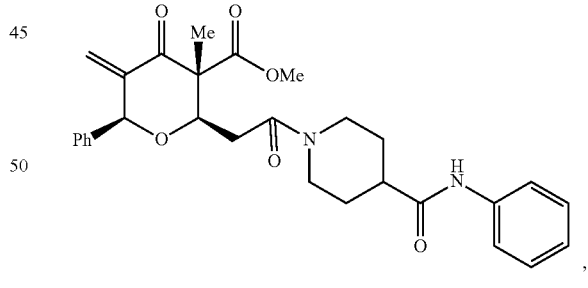
,
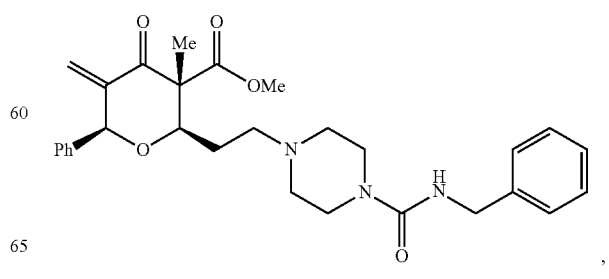
, 25
-continued
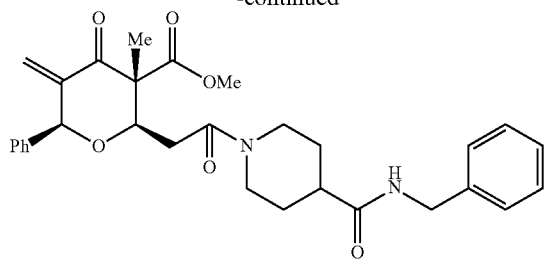
,
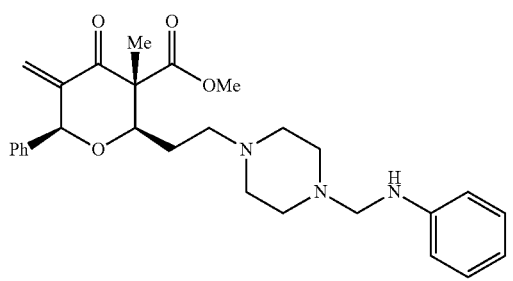
,
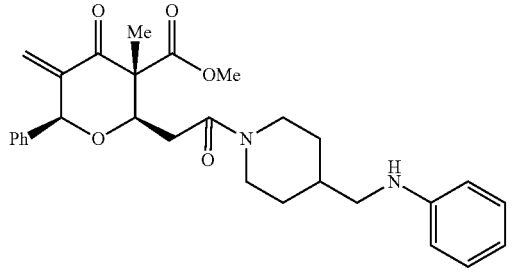
,
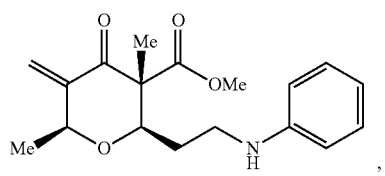
,
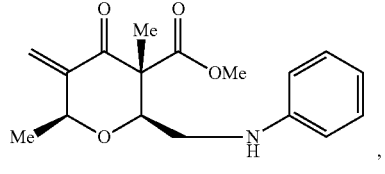
,
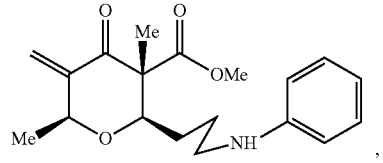
,
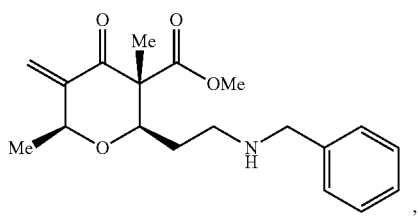
,
26
-continued
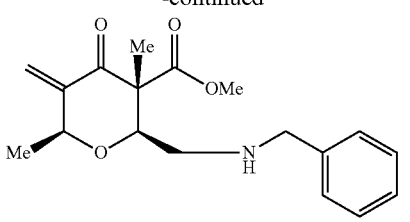
,
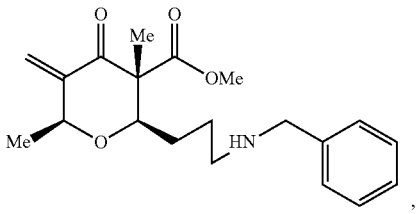
,
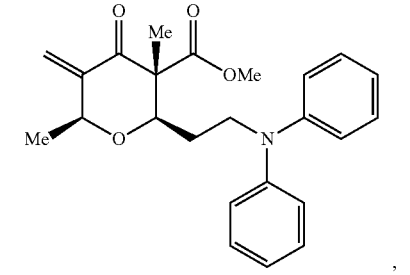
,
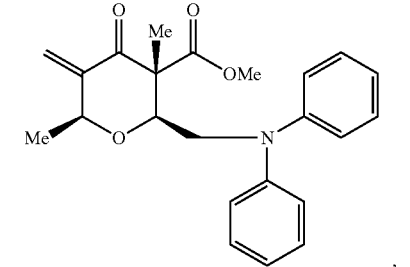
,
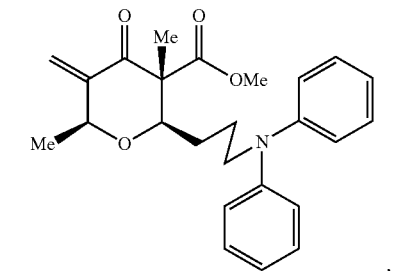
,
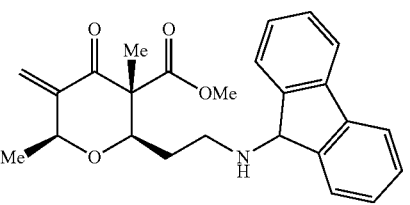
,
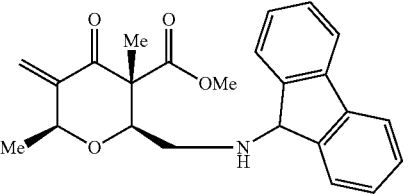
, -continued
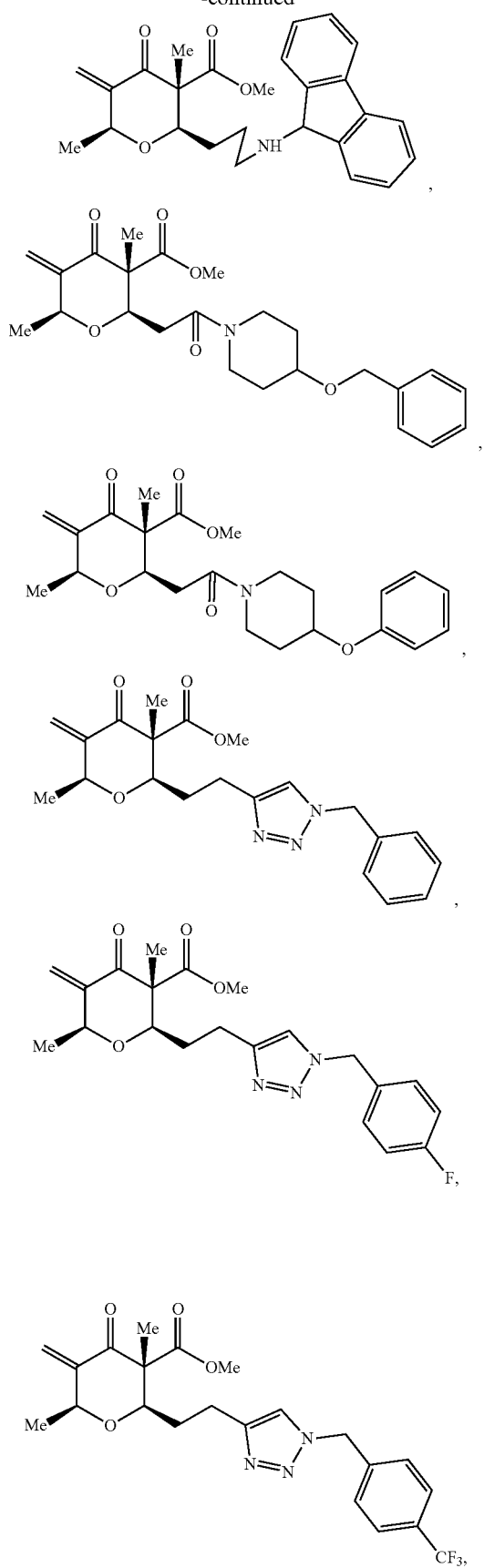
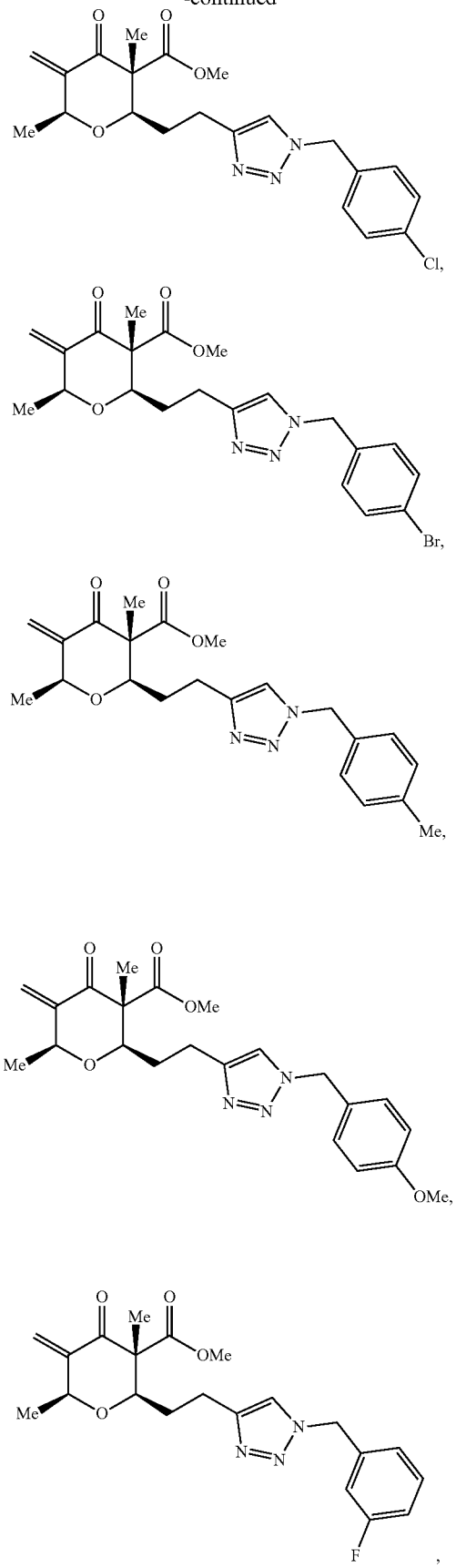

29
-continued
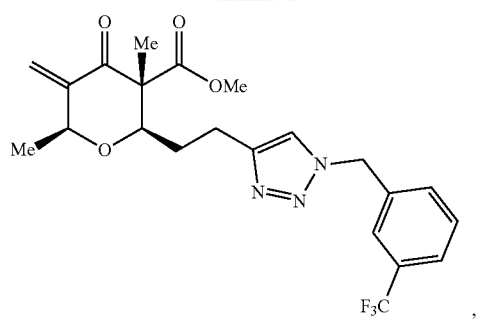
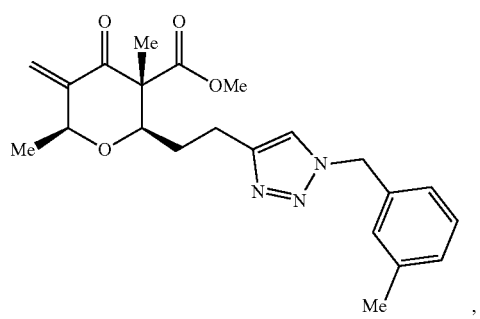
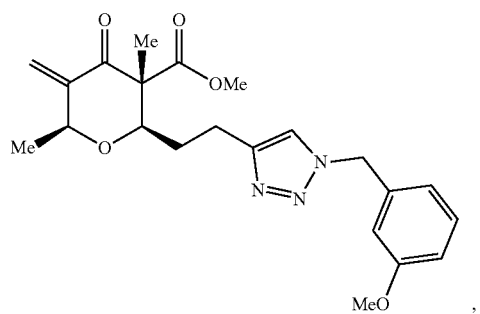
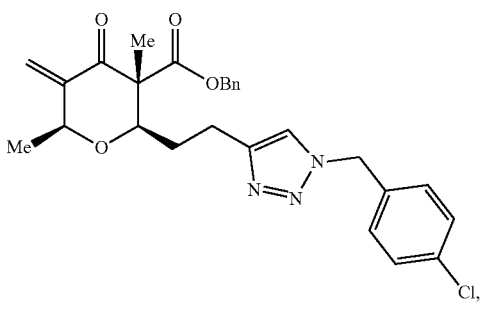
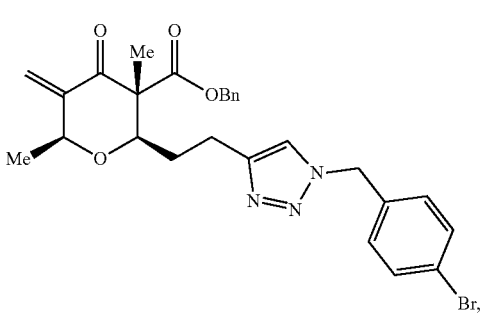
30
-continued
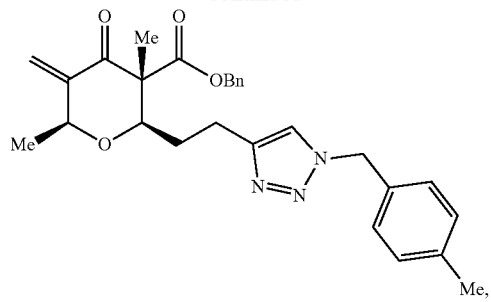
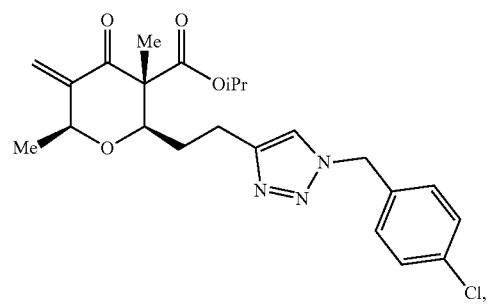
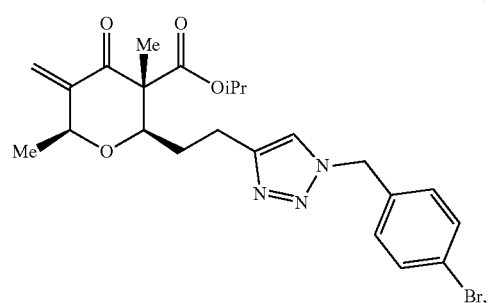
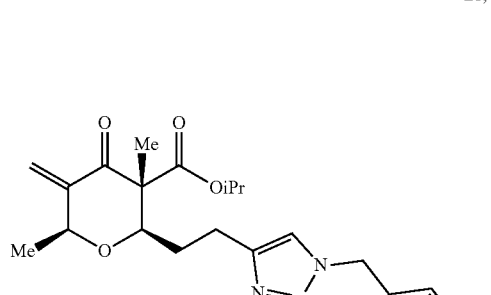
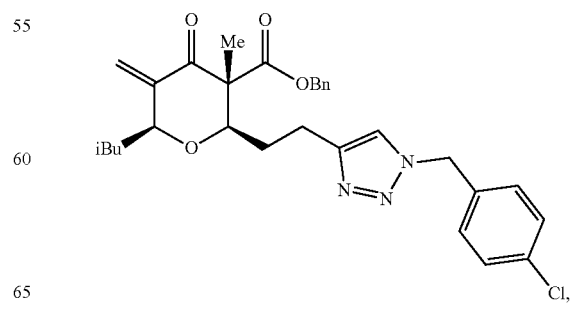

-continued
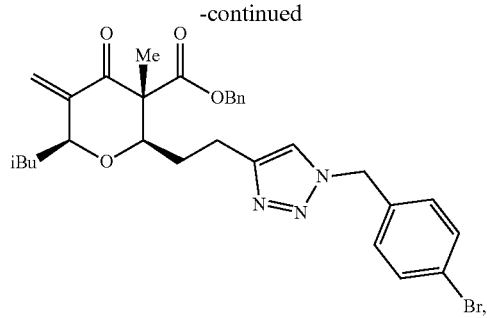
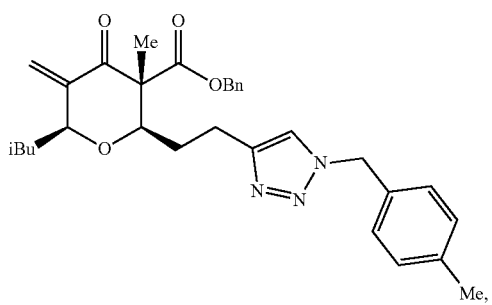
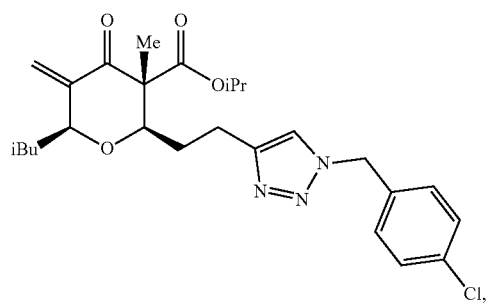
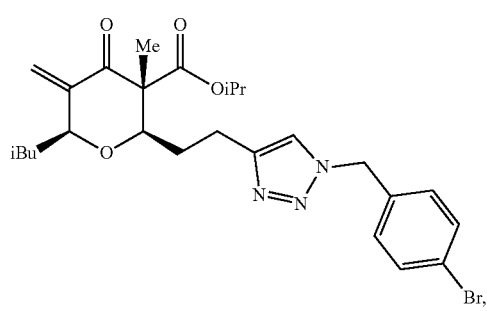
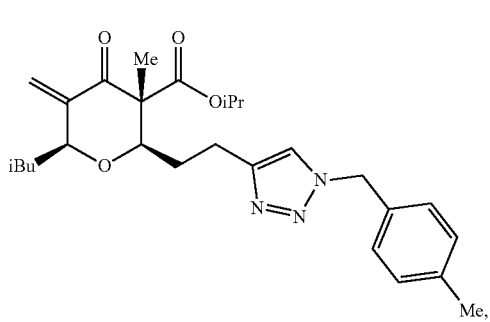
-continued
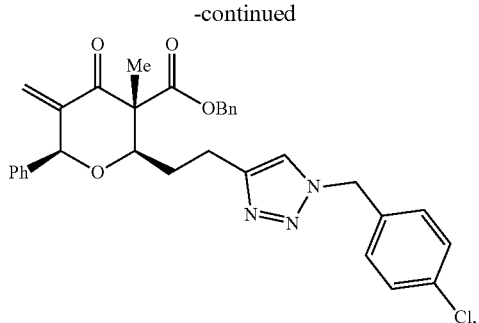
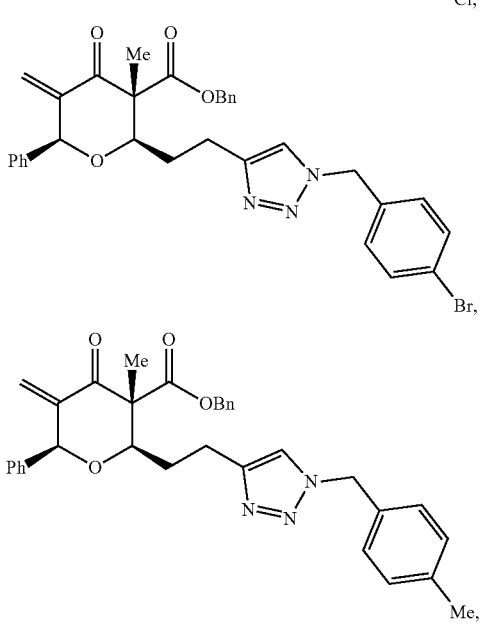
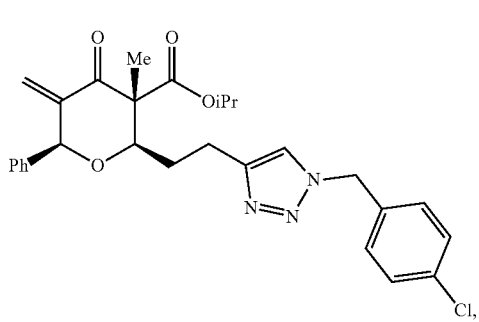

33
-continued
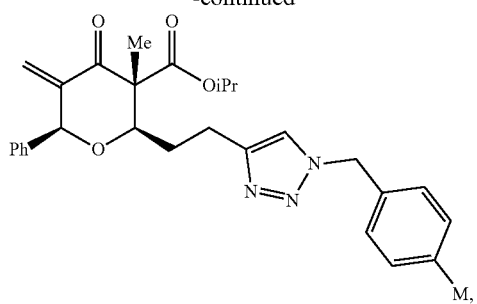
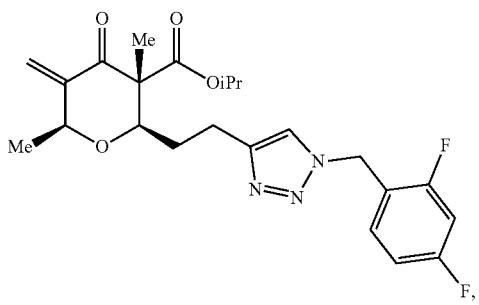
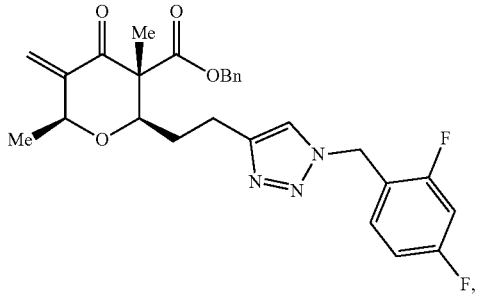
34
-continued
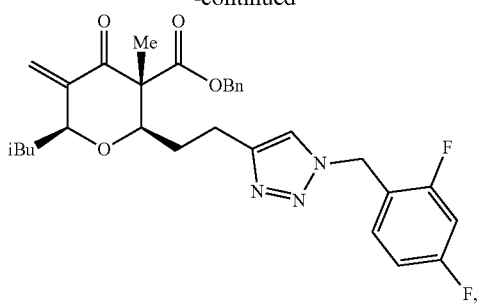
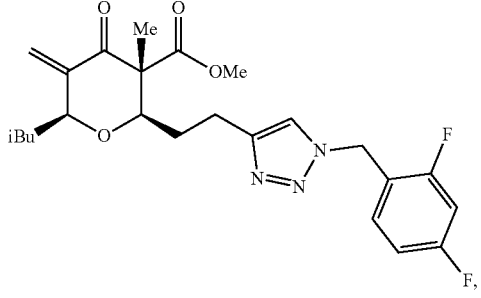
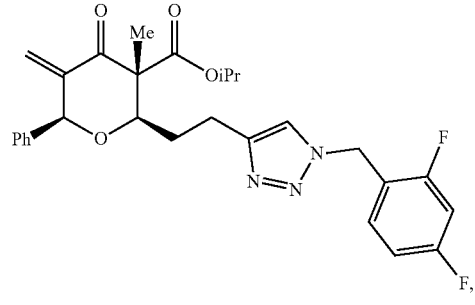
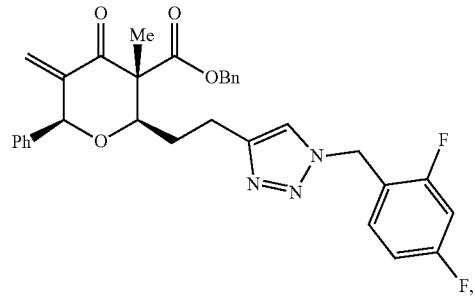
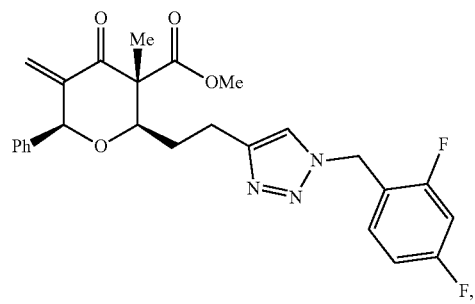

35
-continued

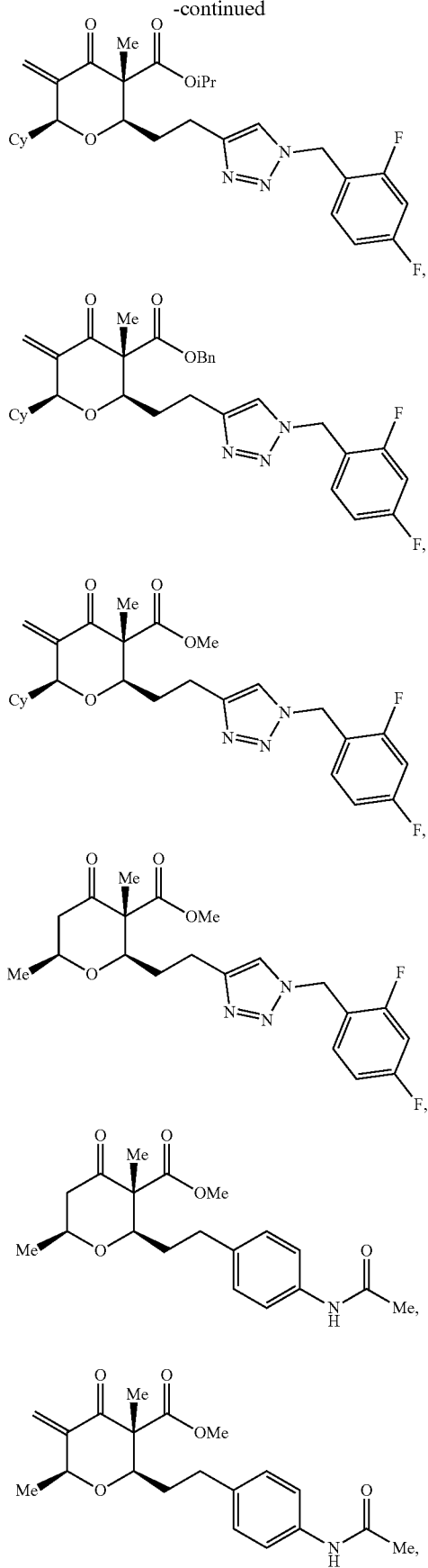

36
-continued

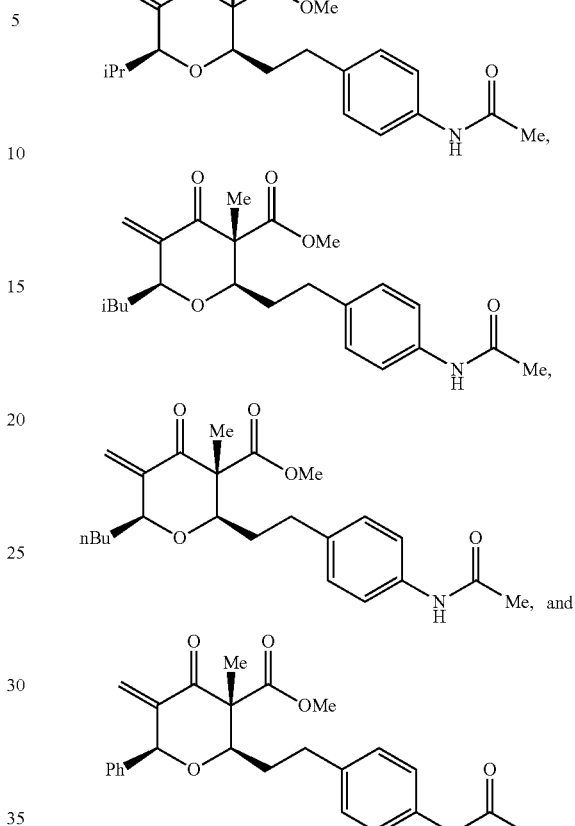

The disclosed compounds may be formulated as pharmaceutical compositions. For example, the disclosed compounds may be formulated as a pharmaceutical composition comprising an effective amount of any of the disclosed compounds together with at least one of a carrier, excipient, or diluent.

The disclosed compounds and pharmaceutical compositions may be administered to a subject in need thereof in order to treat and/or prevent a disease or disorder in the subject. In some embodiments, the disease or disorder is associated with telomerase activity wherein inhibiting telomerase activity treats and/or prevents the disease or disorder. Diseases and disorders treated by the disclosed compounds and pharmaceutical composition may include, but are not limited to, cell proliferative diseases and disorders such as cancer.

The disclosed compounds may be synthesized by modifying methods that are disclosed in the art. First, tetrahydropyran-4-ones precursors of the disclosed compounds may be prepared from dioxinones as disclosed in the art. (See Morris et al., "Stereoselective Synthesis of Tetrahydropyran-4-ones from Dioxinones Catalyzed by Scandium(III) Triflate," Org. Lett. 2005, Vol. 7, No. 6, 1113-1116; the content of which is incorporated herein by reference in its entirety). The tetrahydropyran-4-ones precursors of thus obtained may have a formula selected from:

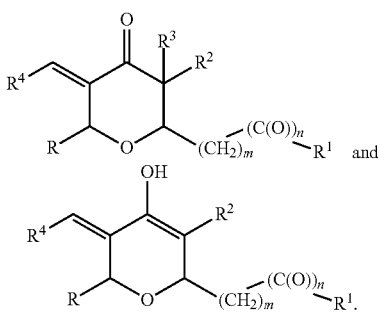

The tetrahydropyran-4-ones precursors may be subjected to α-methylation and then α-methylenation (i.e. at the 3-carbon position) to provide the disclosed 3-methylidene-oxan-4-one compounds and derivatives thereof In some embodiments, the disclosed compounds may lack an α-methylene group (e.g., where the methylene group is replaced with two hydrogen atoms). For example, the disclosed compounds may have a formula selected from:

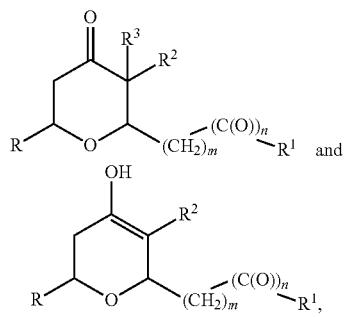

wherein R, $R^1$, $R^2$, and $R^3$ are as defined above for the compounds having an α-methylene group.

The disclosed compounds, salts thereof, and/or hydrates thereof may be formulated as pharmaceutical compositions comprising the compounds, salts thereof, and/or hydrates thereof, in a pharmaceutically acceptable carrier. The pharmaceutical compositions may be formulated for treating one or more of the aforementioned diseases or disorders.

In some embodiments, the disclosed compounds may be used for treating a subject in need of treatment. The methods may include administering to the subject the disclosed compound(s) or compositions comprising the disclosed compounds in an effective amount to treat the disease or disorder. Disease and disorders may include, but are not limited to diseases and disorders associated with telomerase activity. Disease and disorders may include, but are not limited to, cancer and cell proliferative disorders.

EXAMPLES

The following Examples are illustrative and are not intended to limit the scope of the claimed subject matter.
Title—Targeted Covalent Inhibition of Telomerase
Reference is made to Betori et al., "Targeted Covalent Inhibition of Telomerase," ACS Chem. Biol. 2020, 15, 706-717, Feb. 4, 2020, the content of which is incorporated herein by reference in its entirety.
Abstract
Telomerase is a ribonuceloprotein complex responsible for maintaining telomeres and protecting chromosomal integrity. The human telomerase reverse transcriptase (hTERT) is expressed in ~90% of cancer cells where it confers the capacity for limitless proliferation. Along with its established role in telomere lengthening, telomerase also serves non-canonical extra-telomeric roles in oncogenic signaling, resistance to apoptosis, and enhanced DNA damage response. We report a new class of natural product-inspired covalent inhibitors of telomerase that target the catalytic active site.

Results and Discussion

Among the diverse natural products that have been examined as candidate telomerase inhibitors, chrolactomycin (1), a tetrahydropyran macrolide antibiotic isolated from *Streptomyces* sp. 569N-3, was reported to display an $IC_{50}$ of 0.5 μM in in vitro telomerase assays.[52-54] Notably, chrolactomycin's activity was hypothesized to be due to conjugation of the exomethylene group to an undetermined nucleophile. Efforts toward de novo synthesis of the closely related macrolide okilactomycin have been successful, but chrolactomycin has not been accessed by synthesis to date and the length of these routes leaves structure-activity studies essentially unexplored.[55,56] Drawing on our laboratory's previous work on similar tetrahydropyran macrolides,[57-60] we applied rational compound design to chrolactomycin to lead to synthetically tractable, small-molecule analogues. Our goal in these efforts was to preserve the covalent mechanism for hTERT inhibition, providing a novel chemical path toward tool development targeting telomerase.

Figure 2:
FIG. 2: A) Chrolactomycin inhibits telomerase by a covalent mechanism B) Cheminformatics model for binding of chrolactomycin. C) Synthetic sequence for modular access to chrologs.
Figure 2:
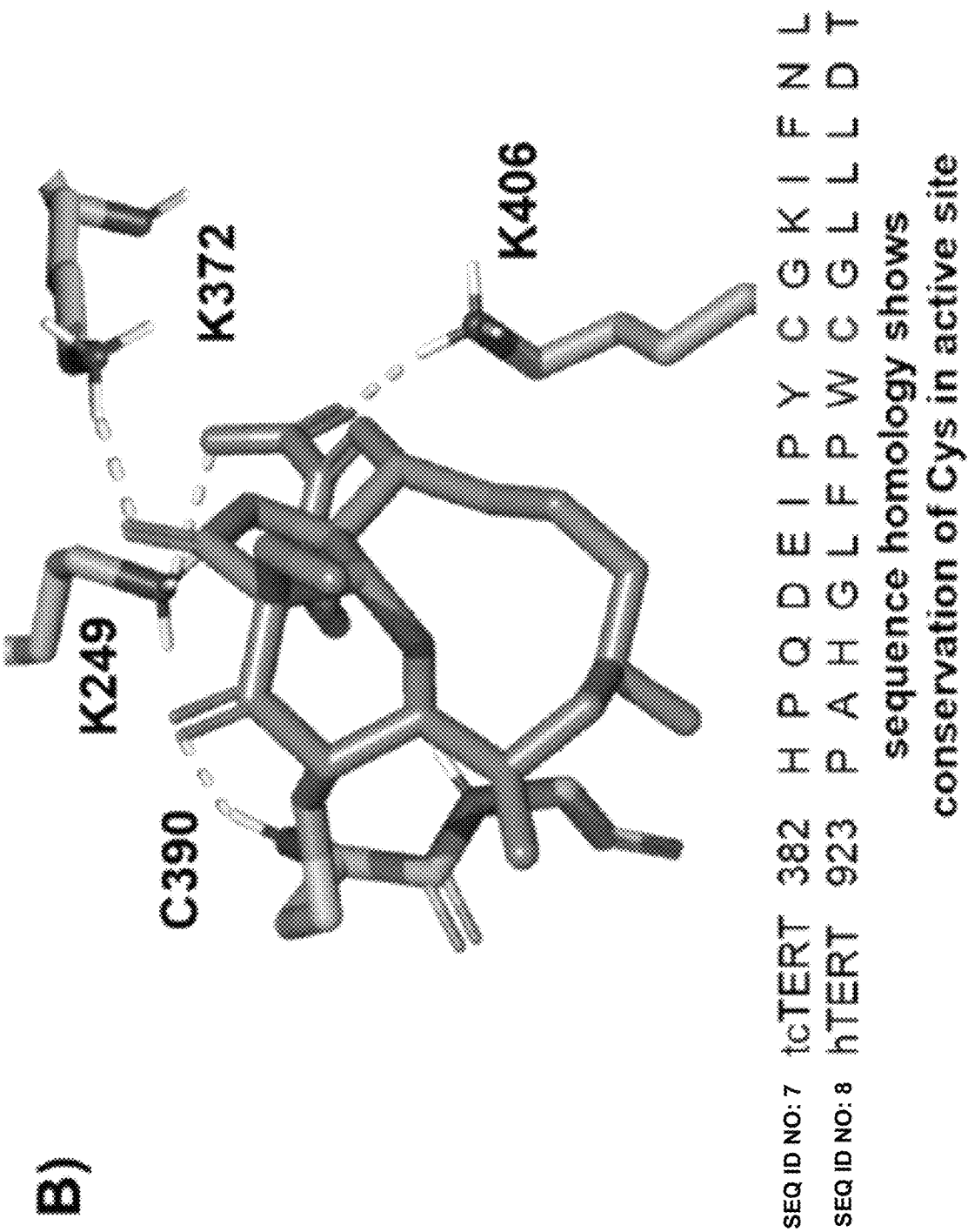
Figure 2:
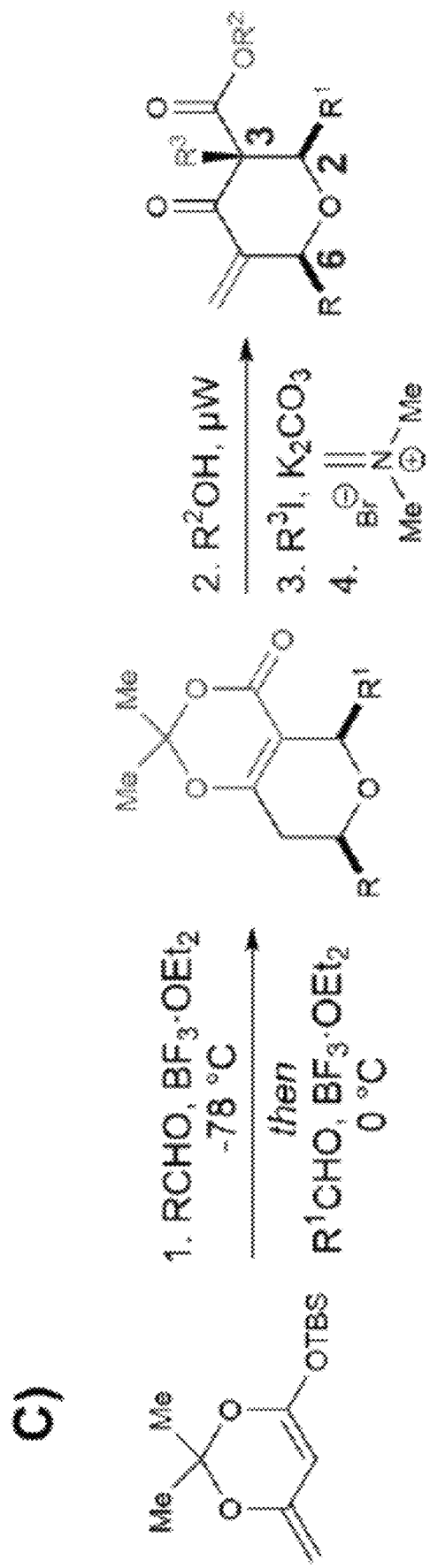

To validate a covalent mechanism for telomerase inhibition by chrolactomycin, we examined effects on the well-studied TERT protein from *Tribolium castaneum*, tcTERT. Proteolysis and tandem mass spectrometry of purified tcTERT treated with 1 μM chrolactomycin in vitro yielded a single modified peptide, HPQDEIPYCGK (SEQ ID NO: 2) (FIG. 2A). Notably, inclusion of costunolide and helenalin, two other natural products postulated to inhibit telomerase activity through a covalent mechanism, showed no adduct formation with any tcTERT peptides, indicating that their telomerase inhibitory mechanism is likely not due to covalent interactions with the reverse transcriptase. Based on the tcTERT crystal structure, the modified residue, C390 (C931 in hTERT), lies within the putative active site.[61,62] Lacking a high resolution structure for hTERT to model chrolactomycin binding,[63] tcTERT was utilized for our in silico studies. Docking of chrolactomycin in the active site of tcTERT was examined using the Schrödinger suite (Glide module). By placing the terminal carbon atom of the α,β-enone of chrolactomycin in close proximity (3.3 Å) to the C390 sulfur atom in the active site, several non-bonding interactions (K249, K406, K372) could be observed with potential to stabilize binding and facilitate delivery of the electrophilic warhead (FIG. 2B). This docking exercise revealed few, if any contacts, between tcTERT and the chrolactomycin macrocycle, which was solvent exposed and played a minimal role in the computed binding energy. Additionally, our computational studies identified that the macrocycle likely serves to rigidify chrolactomycin to orient the exocyclic methylene proximal to C390 for covalent addition.

Drawing on these insights, we designed simplified chrolactomycin analogues (dubbed "chrologs") that might maintain probe-target interactions but could be obtained via an efficient and modular synthetic sequence. Chrologs were designed using the Pipeline Pilot module of the Accelrys software package,[64-66] and compounds were selected based on favorable computed drug-likeness.[67] We scored probes using in silico docking with the Glide module[68-70] and CovDock[71,72] of the Schrödinger suite, where compound prioritization was assigned based on a computed binding energy between C390 and the exocyclic methylene. To commence, bicyclic dioxinones were obtained by a one-pot vinylogous Mukaiyama aldol reaction between aldehydes and silyl dioxinone dienolates using BF3.OEt$_2$ at −78° C., followed by warming up the reaction mixture to 0° C. and charging of a different aldehyde and additional BF3.OEt$_2$.[73] Dioxinone opening and subsequent trapping of the acyl ketene intermediate by an alcohol nucleophile afforded the β-ketoester. Lastly, the target structures were accessed by α-methylation and then a modified Mannich-type methylenation (FIG. 2C). Notably, these simplified analogues could be accessed in 4 steps vs. >25 steps required for the syntheses of okilactomycin.

In developing a preliminary structural activity relationship (SAR) for the chrologs, we divided the structure of the pyran into four main components: (1) C-2 substituents (carboxylic acid of chrolactomycin); (2) C-6 substituents (chrolactomycin macrolide loop); (3) C-3 substituents (fused γ-lactone of chrolactomycin) and (4) inclusion of the exocyclic methylene group. We carried out systematic modifications of each structural unit and evaluated the effects on telomerase activity as measured by a PCR-based telomerase activity assay (TRAP assay).[16]

First, the effects of C-2 substitution were investigated (Table 1).

TABLE 1

Structure-Activity Relationships of C-2 and C-6 Groups

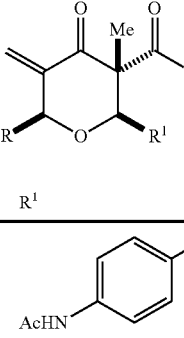

| Compound | R | R$^1$ | IC$_{50}$ (μM) | ΔG Binging (kcal/mol) |
|---|---|---|---|---|
| 4a | Me |  AcHN-C$_6$H$_4$-CH$_2$CH$_2$- | 1.5 | −31.9 |
| 4b | Me | Ph-CH$_2$CH$_2$- | >100 | N/A |
| 4c | Me | (CH$_3$)$_2$CH-CH$_2$- | >100 | N/A |
| 4d | Me |  4-F-C$_6$H$_4$-CH$_2$CH$_2$- | 42 | −27.5 |
| 4e | Me | 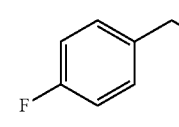 4-CF$_3$-C$_6$H$_4$-CH$_2$CH$_2$- | 55 | −22.8 |
| 4f | Me | 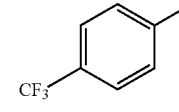 4-MeO-C$_6$H$_4$-CH$_2$CH$_2$- | 62 | −21.1 |
| 4g | Me | 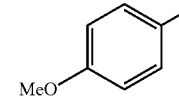 3-AcHN-C$_6$H$_4$-CH$_2$CH$_2$- | 11 | −28.6 |
| 4h | Me | 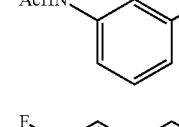 3-F-C$_6$H$_4$-CH$_2$CH$_2$- | >100 | N/A |
| 4i | (CH$_3$)$_2$CH- | 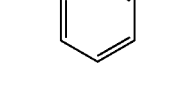 4-AcHN-C$_6$H$_4$-CH$_2$CH$_2$- | 45 | −27.7 |

TABLE 1-continued

Structure-Activity Relationships of C-2 and C-6 Groups

[Structure: pyranone with exocyclic methylene, C-3 quaternary center bearing Me and CO₂Me, with R and R¹ groups at C-6 and C-2]

| Compound | R | R¹ | IC$_{50}$ (μM) | ΔG Binging (kcal/mol) |
|---|---|---|---|---|
| 4j | Ph(CH₂)₂- | 4-(AcHN)C₆H₄(CH₂)₂- | >100 | N/A |

The inclusion of a hydrogen-bonding group was found to be crucial, where a para N-acetylphenethyl group showed loss of telomerase activity (1.5 μM), compared to phenethyl and isobutyl groups (>100 μM). Exchange of the para N-acetylphenethyl group for para-fluorophenethyl, para-trifluoromethylphenethyl, para-methoxyphenethyl and all meta-substituted compounds showed reduced potency. Subsequently, we evaluated the role that C-6 substitution had on telomerase activity (Table 1). Surprisingly there was minimal steric tolerance at this position, where substitution of the C-6 methyl group for more sterically encumbered groups such as isobutyl and phenethyl showed a drop in activity. This loss of activity is likely due to the larger alkyl groups at C-6 providing a greater hydrophobic surface that destabilizes compound binding to TERT prior to covalent modification. The smaller C-6 methyl group provides minimal hydrophobic interactions, allowing for the predisposition of the exocyclic methylene proximal to C390 to facilitate C—S bond formation. Additionally, this trend in biological activity is reinforced by computed binding energies.

Next, we investigated the role of the β-ketoester in telomerase activity (Table 2).

TABLE 2

Structure-Activity Relationships of C-3 Group

[Structure: pyranone core with Me at C-6, CH₂CH₂-C₆H₄-NHAc at C-2, exocyclic methylene, and C-3 bearing R¹ and C(O)R]

| Compound | R | R¹ | IC$_{50}$ (μM) | ΔG Binging (kcal/mol) |
|---|---|---|---|---|
| 4a | -OMe | Me | 1.5 | -31.1 |
| 4k | -OCH(Me)₂ | Me | 45 | -25.9 |
| 4l | -OCH₂-cyclopropyl | Me | 75 | -18.0 |
| 4m | -OCH₂Ph | Me | 35 | -27.9 |
| 4n | -OCH₂CH₂Ph | Me | >100 | N/A |
| 4o | -OCH₂CH₂CH₂Me | Me | 85 | -16.5 |
| 4p | -OCH₂CH₂OMe | Me | 25 | -23.1 |
| 4q | -OMe | Et | 15 | -25.6 |
| 4r | -OMe | iPr | 62 | -22.1 |

More sterically encumbered esters such as isopropyl, methylcyclopropyl, benzyl, and n-butyl proved deleterious to biological activity. Inclusion of H-bonding elements (methoxyethane) pendant on the alcohol nucleophile showed no demonstrable increases in activity. Unfortunately, attempts to access β-ketoamide derivatives were unsuccessful as these substrates were prone to decomposition during installation of the exocyclic methylene group. Introduction of the α-methoxy group either through direct methoxylation or hydroxylation-alkylation strategies was unfruitful, providing only enone structures. To identify if potential H-bonding due to the α-methoxy group in chrolactomycin was beneficial for biological activity, we conducted a direct comparison between chrolactomycin and okilactomycin, where the only structural difference is the exchange of the α-methoxy group for a α-methyl. This change showed that the α-methoxy group minutely impacted telomerase inhibition (0.5 μM to 2.1 μM), leading us to be content with the installation of alkyl groups at the C-3 position. We identified that a α-methyl group at C-3 provided the highest level of activity. Lastly, removal of the exocyclic methylene showed a dramatic loss of activity, indicating a covalent warhead remained critical for telomerase inhibition.

While our synthetic sequence allowed for efficient access to racemic analogues, attempts to access enantioenriched chrologs via the β-hydroxy dioxinones through a variety of vinylogous Mukaiyama aldol approaches were unsuccessful.[74-79] Fortunately, the utilization of a ketoreductase (KRED) mediated asymmetric reduction from the corresponding β-keto dioxinone was able to afford the desired β-hydroxy dioxinone in near quantitative yield and enantioselectivity (see FIG. 3a and Supporting Information in Example 2).[80] Utilizing this enantiopure β-hydroxy dioxinone, the enantiopure para N-acetylphenethyl analogue was accessed in 4 steps and showed an $IC_{50}$ of 0.9 μM, a near 2-fold potency increase relative to the racemic analogue. Notably, the opposite antipode was also evaluated in the TRAP assay, providing an $IC_{50}$ of 4.5 μM. With a first generation of chrologs synthesized and evaluated, we observed a near linear relationship between computed binding energy and $IC_{50}$ values ($R^2=0.81$, see Supporting Information), strongly supporting our computational docking model.

Figure 3:
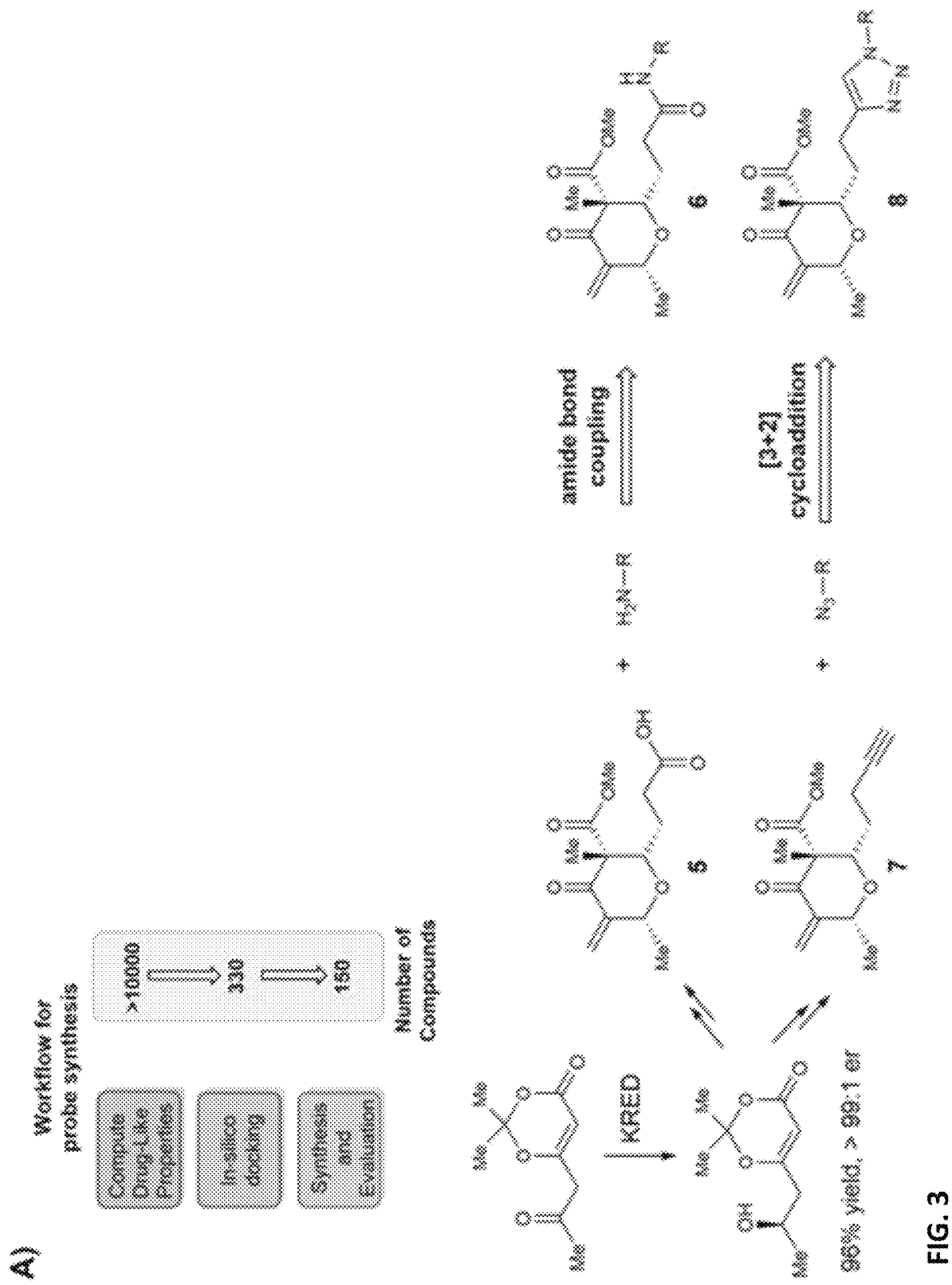
FIG. 3: A) Workflow for probe synthesis. B) Optimized analogue NU-1 and des-exomethylene inactive analogue NU-2. C) Cheminformatics model for binding of NU-1. Telomerase inhibition of NU-1 as measured by TRAP assay in telomerase-positive D) cell lysates and E) cells in culture.
Figure 3:
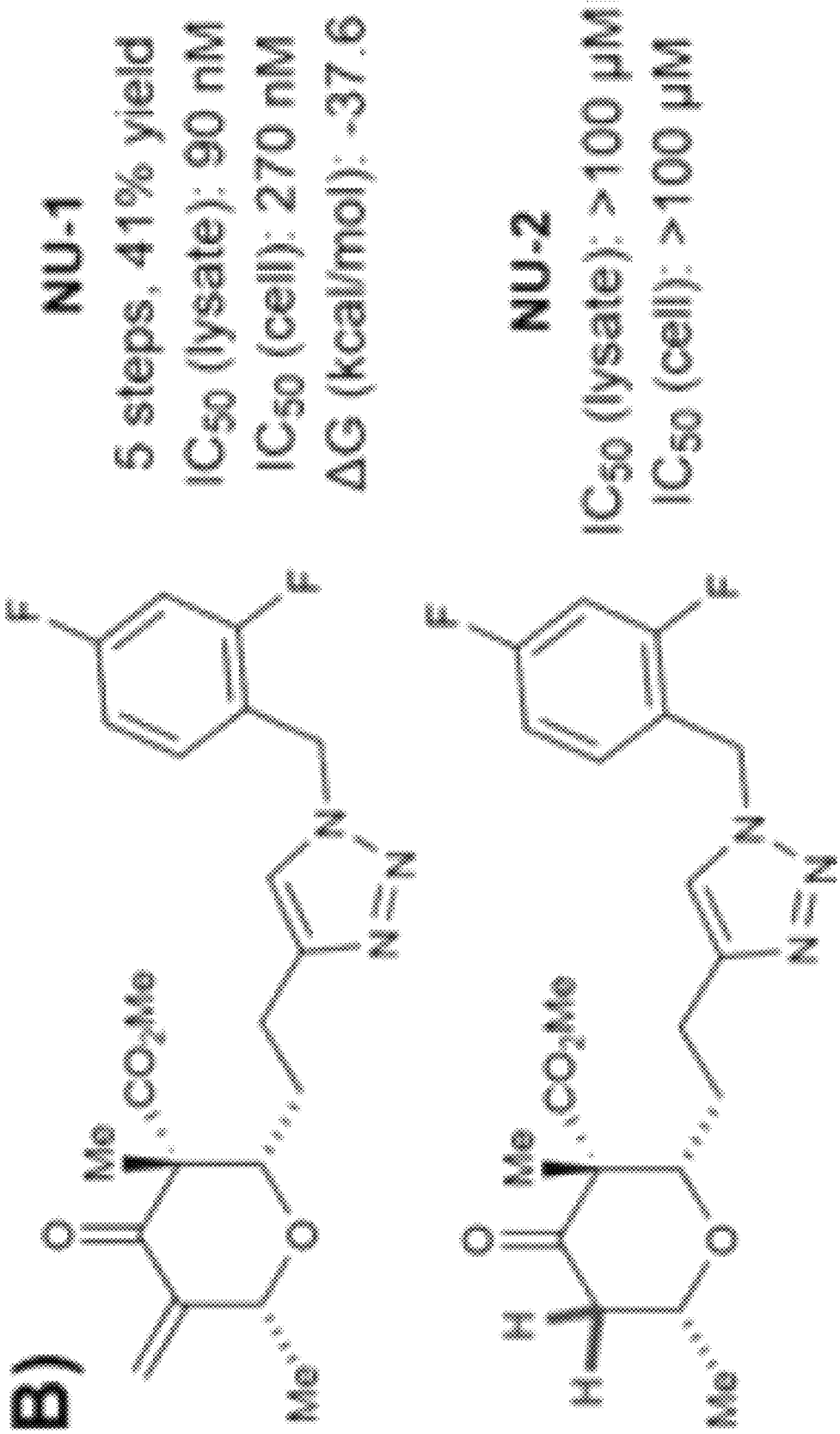
Figure 3:
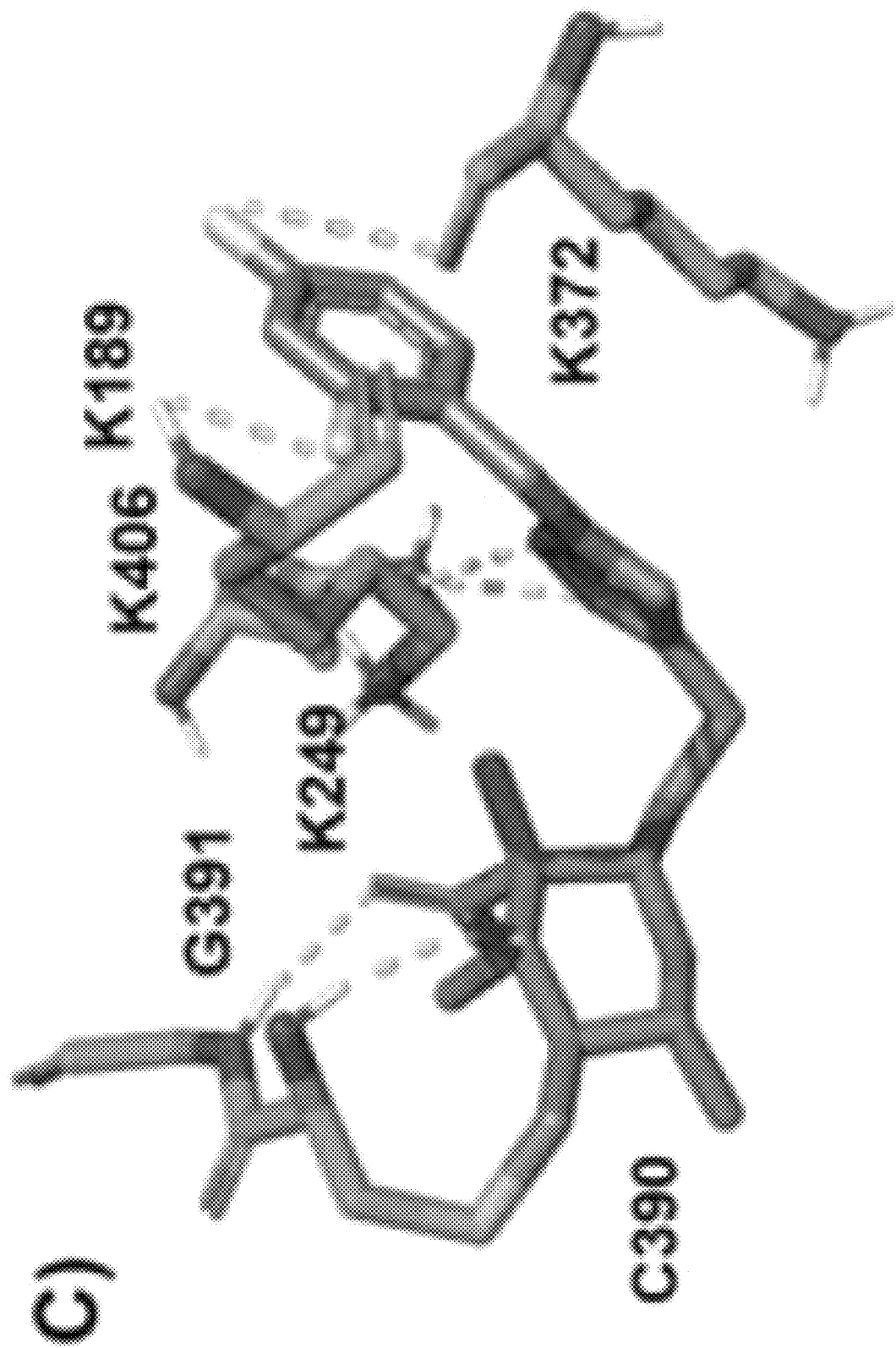

With the necessary enantioenriched β-hydroxy dioxinone in hand, we subsequently re-evaluated our cheminformatics model to accommodate for this stereochemical information. Compounds were designed as previously mentioned using Pipeline Pilot.[64-66] We then selected ~330 compounds that had favorable computed drug-likeness.[67] We scored probes using in silico docking with the Glide module[68-70] and CovDock[71,72] of the Schrödinger suite to select and synthesize ~150 compounds, focusing on C-2 modification. SAR analysis was focused on increasing H-bonding interactions by targeting structure classes poised for late-stage diversification through amide bond formations and [3+2] cycloadditions to facilitate rapid library development (FIG. 3A). The goal in this $2^{nd}$ generation library synthesis was to obtain a chrolactomycin analogue with an $IC_{50}<100$ nM.

Briefly, a series of simple amines were investigated as amide bond coupling partners with carboxylic acid pyranones 5 to obtain amide analogues 6 (see SI). Notably, analogues that had electron withdrawing groups on the aryl ring showed increased activity relative to unsubstituted analogues, indicating that there may be some H-bonding involved at that position. To attempt to take further advantage of H-bonding at the C-2, analogues that contained either a piperazine or 4-aminopiperidine linker were designed. We were pleased to find that this series of compounds showed higher activity in comparison to the simple amide analogues, indicating that the initial presumption that larger groups at this C-2 position that could participate in additional H-bonding was worth pursuing. Subsequently, we utilized alkyne containing pyranone 7 to start evaluating triazole analogues 8, where we were pleased to find that triazole analogues displayed higher activity in comparison to the amide analogues (see SI). Additionally, the same trend regarding analogues that had electron withdrawing groups on the aryl ring showing increased activity was observed (see Supporting Information for all relevant docking experiments). Optimization led to lead compound NU-1 that displayed an $IC_{50}=90$ nM in TRAP assays in MCF7 cell lysate in vitro and an $IC_{50}=270$ nM in MCF7 cells in culture (FIG. 3B). Additionally, we were pleased to find that NU-1 had the highest binding energy of all compounds synthesized and evaluated in the TRAP assay (−36.5 kcal/mol), further reinforcing our computational design approach (FIG. 3C). Notably, the electron withdrawing groups present on the aromatic ring of NU-1 showed the capability to pick up H-bonding interactions with K372 and K189 found in the TERT active site, lending additional evidence to our observation that substituents on the aromatic ring play a noticeable role in binding energy and telomerase inhibition.

These results were confirmed in four other telomerase-positive human cancer cell lysates and whole cells; A549 non-small cell lung cancer, ACHN renal carcinoma, MDA-MB-231 triple negative breast cancer and HeLa cervical cancer (FIG. 3D-E and data not shown). To evaluate the role that the exocyclic methylene warhead plays in biological activity, we also synthesized the des-exocyclic methylene analogue NU-2. Notably, NU-2 displayed no appreciable inhibition of telomerase activity, indicating a covalent mechanism remained critical for telomerase inhibition.

NU-1 displayed satisfactory performance in plasma and microsomal stability assays, and showed favorable lipophilicity and CYP450 inhibition profiles (see the Supporting Information). To assess cysteine reactivity, we utilized the glutathione mimic N-acetyl cysteine (NAC) and measured the rate of chemical reactivity of NU-1 by HPLC.[81-84] Briefly, 1 μM NU-1 was incubated with 5 mM of NAC (where both are at a concentration to best mimic cellular assay conditions) and the half-life was calculated by fitting to a pseudo-first-order kinetic rate equation relative to natural log transformed percent remaining NU-1. We were pleased to find that NU-1 demonstrated moderate thiol reactivity ($t_{1/2}=42$ min) that is comparable to previously established guidelines for suitable reactivity windows for targeted covalent inhibitors.[85-87]

To evaluate if NU-1 was reactive with other potential cellular nucleophiles, NU-1 was incubated with N-acetyl serine and N-acetyl lysine, and the rate of chemical reactivity was measured by HPLC. No amino acid adducts were found, indicating that NU-1 is specific for thiol nucleophiles. Moreover, incubation of NU-1 with glycine showed no ketone-Schiff base formation. When NU-1 was incubated with tcTERT, proteolysis and mass spectrometry yielded a single modified peptide HPQDEIPYCGK (SEQ ID NO: 2), localizing the site of modification to the active site C390 and confirming a shared mechanism of action with chrolactomycin (see the Supporting Information).

Figure 4:
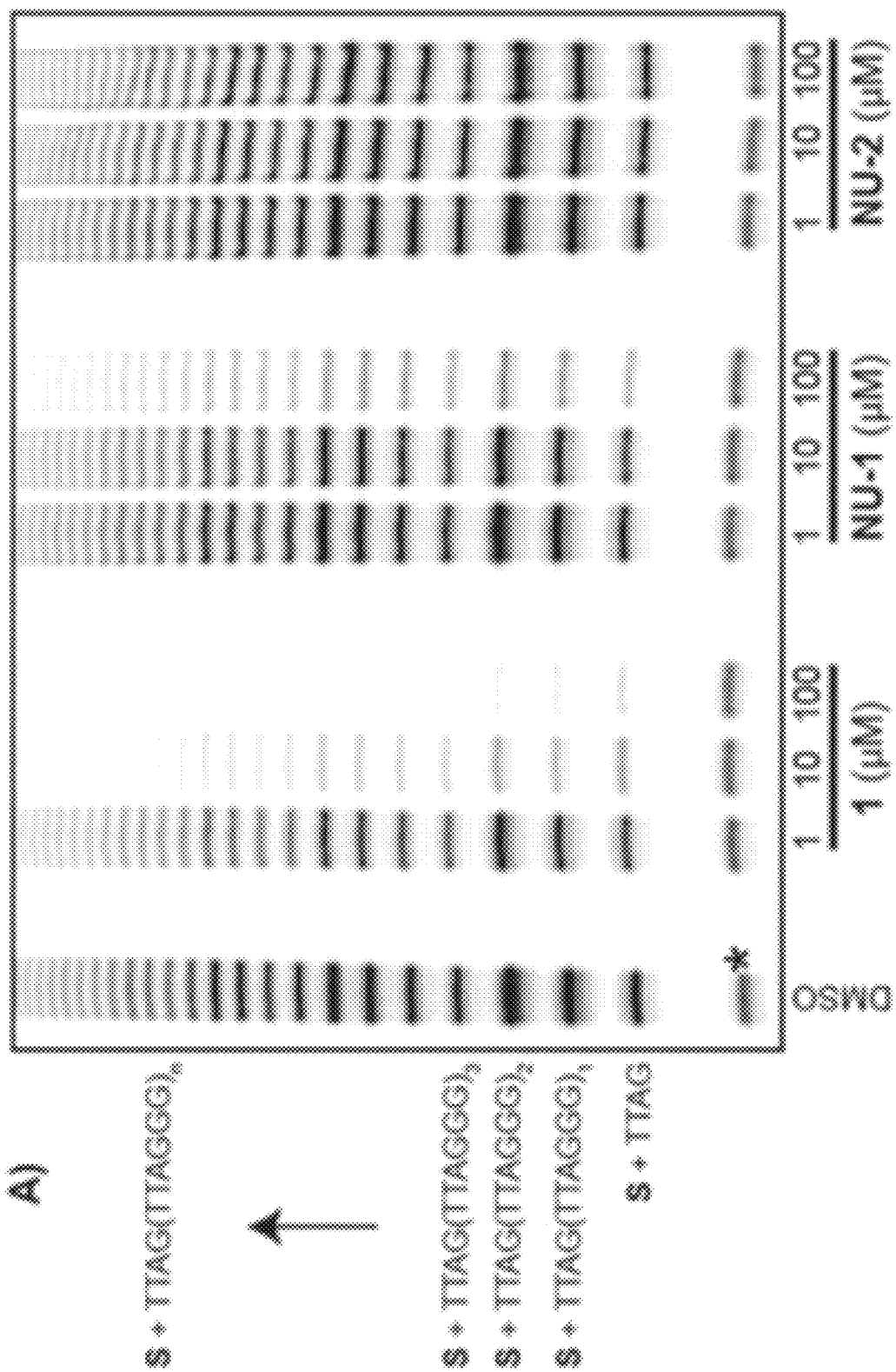
FIG. 4: Direct telomerase activity assays: reaction of 5'-biotin-CTAGACCTGTCATCA(TTAGGG)$_3$ (SEQ ID NO: 1) (S) with human telomerase and dTTP, dATP, and α-$^{32}$P-dGTP. (A) Incubation of purified telomerase with varying concentrations of chrolactomycin 1, NU-1, or control compound NU-2; DMSO is the vehicle control. Asterisk indicates a $^{32}$P-labelled recovery/loading control DNA. (B) Time course of irreversible inhibition of purified telomerase by NU-1. (C) Endogenous telomerase activity from A549 or MCF7 cells after 24 h treatment with DMSO (vehicle control), NU-1, or NU-2.
Figure 4:
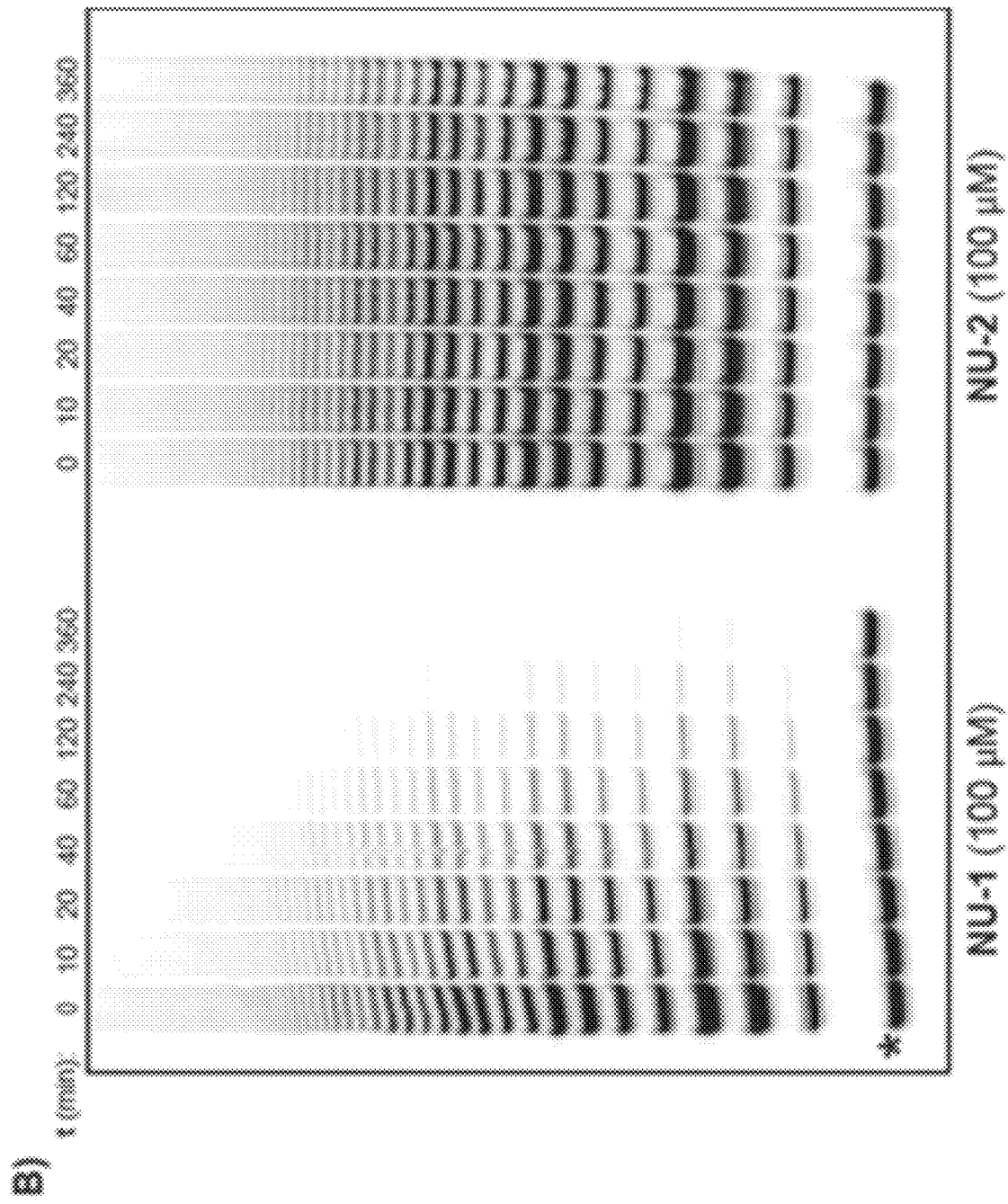
Figure 4:
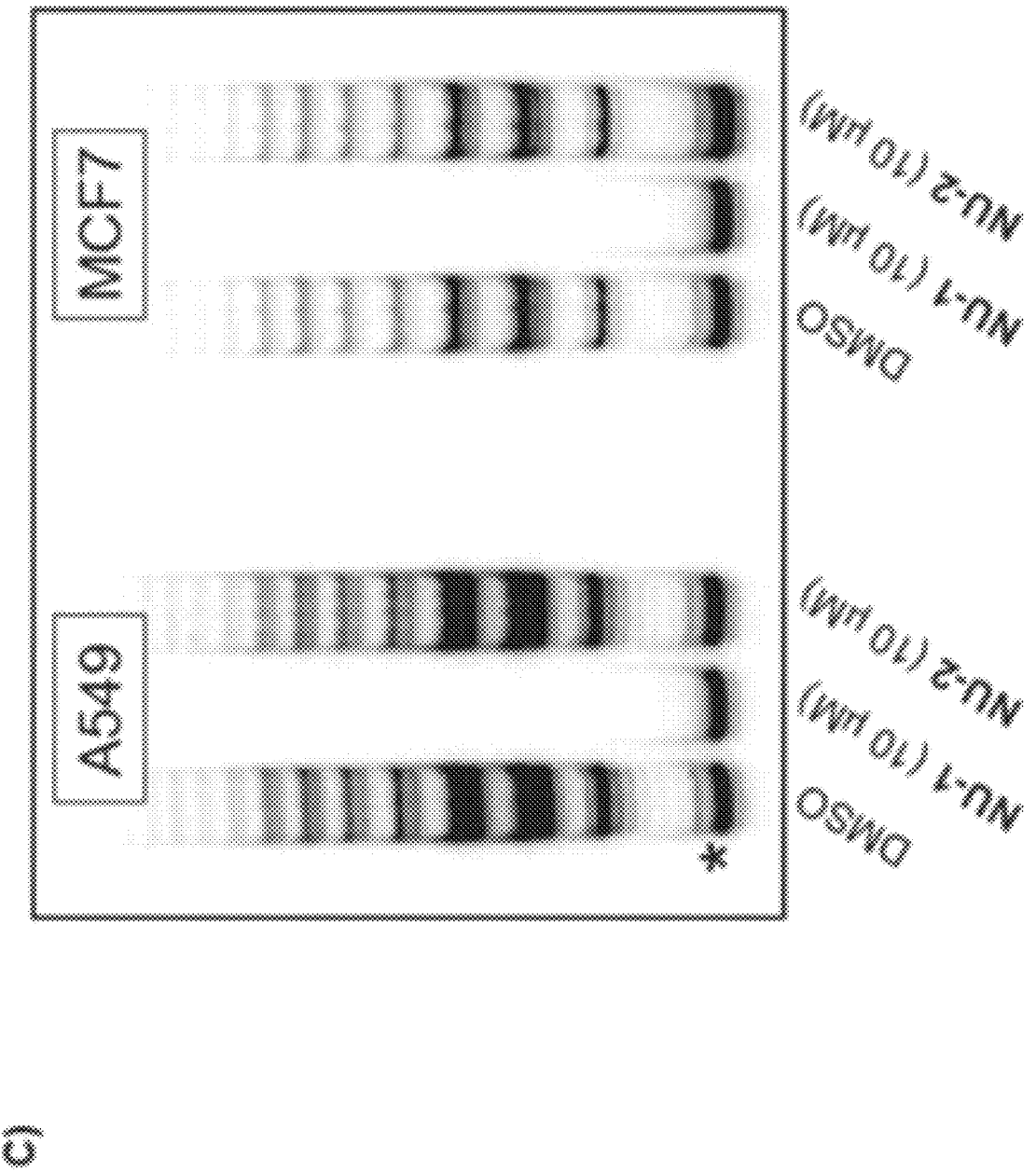

To further evaluate NU-1, inhibition of telomerase activity was assessed by direct (non-PCR) primer extension assay. Human telomerase purified from telomerase-overexpressing HEK293T cells[88,89] was treated with 1, NU-1 or NU-2. NU-1 and 1 inhibited telomere repeat synthesis in the low-micromolar range, while NU-2 displayed no inhibition (FIG. 4A), verifying the critical role of the enone warhead. Incubation of purified telomerase with 100 μM NU-1 displayed irreversible inhibition kinetics with a $t_{1/2}$ of ~15 min at 23° C., with complete inhibition observed after ~6 h (FIG. 4B). We then assessed inhibition of endogenous telomerase in MCF-7 and A549 cells after culture in the presence of 10 μM NU-1 or NU-2 control for 24 h. NU-1 completely eliminated endogenous telomerase activity, whereas NU-2 was indistinguishable from the DMSO (vehicle) control (FIG. 4C). The difference between the telomerase inhibition observed for the TRAP assay ($IC_{50}=500$ nM for 1 and $IC_{50}=90$ nM for NU-1) and the primer extension assay (1~10× more active than NU-1) could potentially be due to artifacts that are impacting the PCR amplification step of the TRAP assay such as impurities in the cell lysate[90,91] or that either NU-1 or 1 inhibit Taq polymerase at differing levels.

Notably, even a modest impact on Taq polymerase activity would have greatly augmented effects on the assay due to PCR amplification. This contrasts with direct primer extension assay, which is carried out with purified telomerase enzyme and the specific reason we employed this method. In addition, the determination of true "potency" as traditionally defined is difficult using the primer extension assay because the system is not at equilibrium; only when all activity is killed is the system at equilibrium (i.e., every molecule of hTERT is covalently inhibited).

To evaluate the impacts of telomerase inhibition on cell proliferation, MCF7 cells were cultured in media containing 1, NU-1 or NU-2. Both exomethylene-bearing compounds conferred similar dose-responsive loss of viability ($IC_{50}$ of 21 µM and 27 µM respectively), while NU-2 had no effect. A similar pattern was observed in A549, ACHN, MDA-MB-231, and HeLa telomerase-positive cells. By contrast, like DMSO control or 2, treating the telomerase-negative cancer cell lines Saos-2 or VA-13[92] with up to 100 µM 1 or NU-1 did not affect viability (FIG. 5A and data not shown). These results are in-line with previous observations demonstrating that acute hTERT or hTR knockdown and telomerase inhibition results in a decrease in cell proliferation and viability independent of telomere length and integrity.[93-96]

Consistent with a covalent mechanism, washing the treated cells to remove free NU-1 and then incubation in fresh culture media did not restore viability or telomerase activity even after 24 h (FIG. 5B-C and data not shown). Comparing NU-1 to the reversible telomerase inhibitors BIBR1532 ($IC_{50}$~1 µM) or MST-312 ($IC_{50}$~1 µM) in MCF7 cells revealed qualitatively similar effects on viability, though NU-1 displayed the lowest apparent $IC_{50}$. However, when treated MCF7 cells were washed and allowed to recover for 4 h, telomerase activity was restored in cells treated with BIBR1532 or MST-312 (FIG. 5D and data not shown) but remained blocked in cells treated with NU-1.

To assess the full extent of protein labeling in telomerase positive cells (and thereby potential off-target reactivity that may complicate biological analysis), we utilized a competitive gel imaging technique employed in competitive activity-based protein profiling (ABPP)[97-106], where compounds are assayed for their ability to block fluorescent probe labeling. A key advantage of competitive ABPP is that it allows for the evaluation of potency and selectivity of inhibitors without modulating the core structure of the parent compound.

Figure 6:
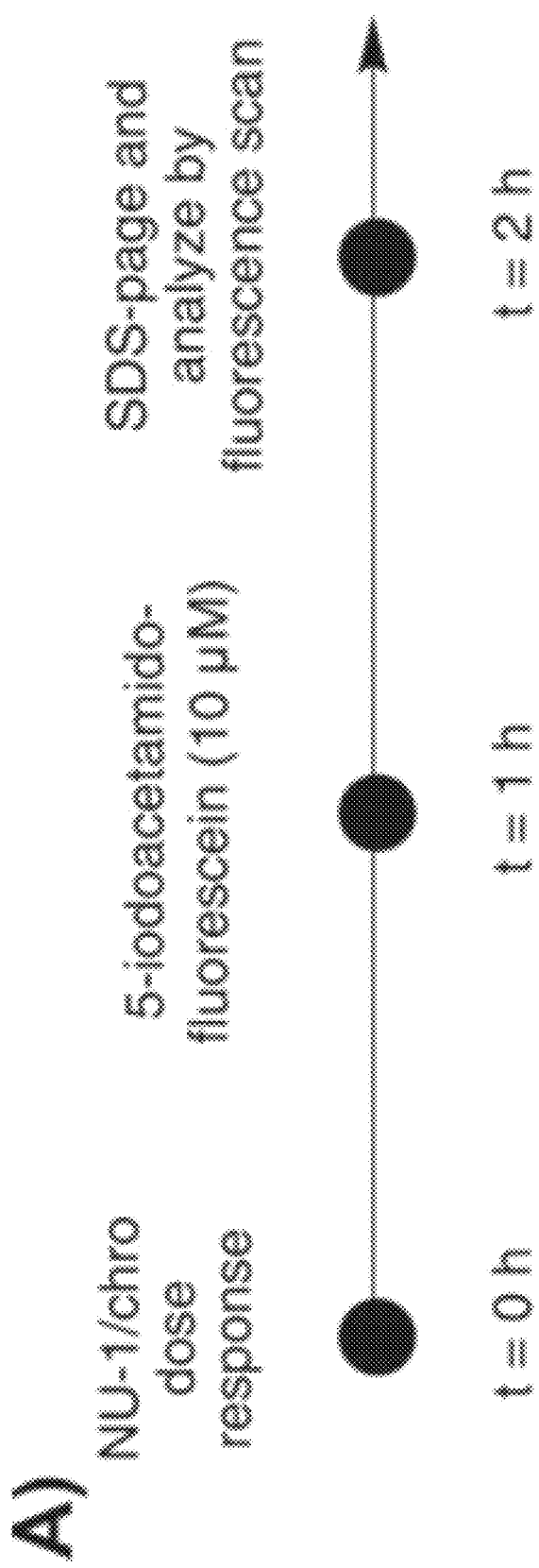
FIG. 6: A) Workflow for competitive gel analysis of NU-1/chrolactomycin with 5-iodoacetamido-fluorescein. Gel image of B) NU-1 and C) chrolactomycin.
Figure 6:
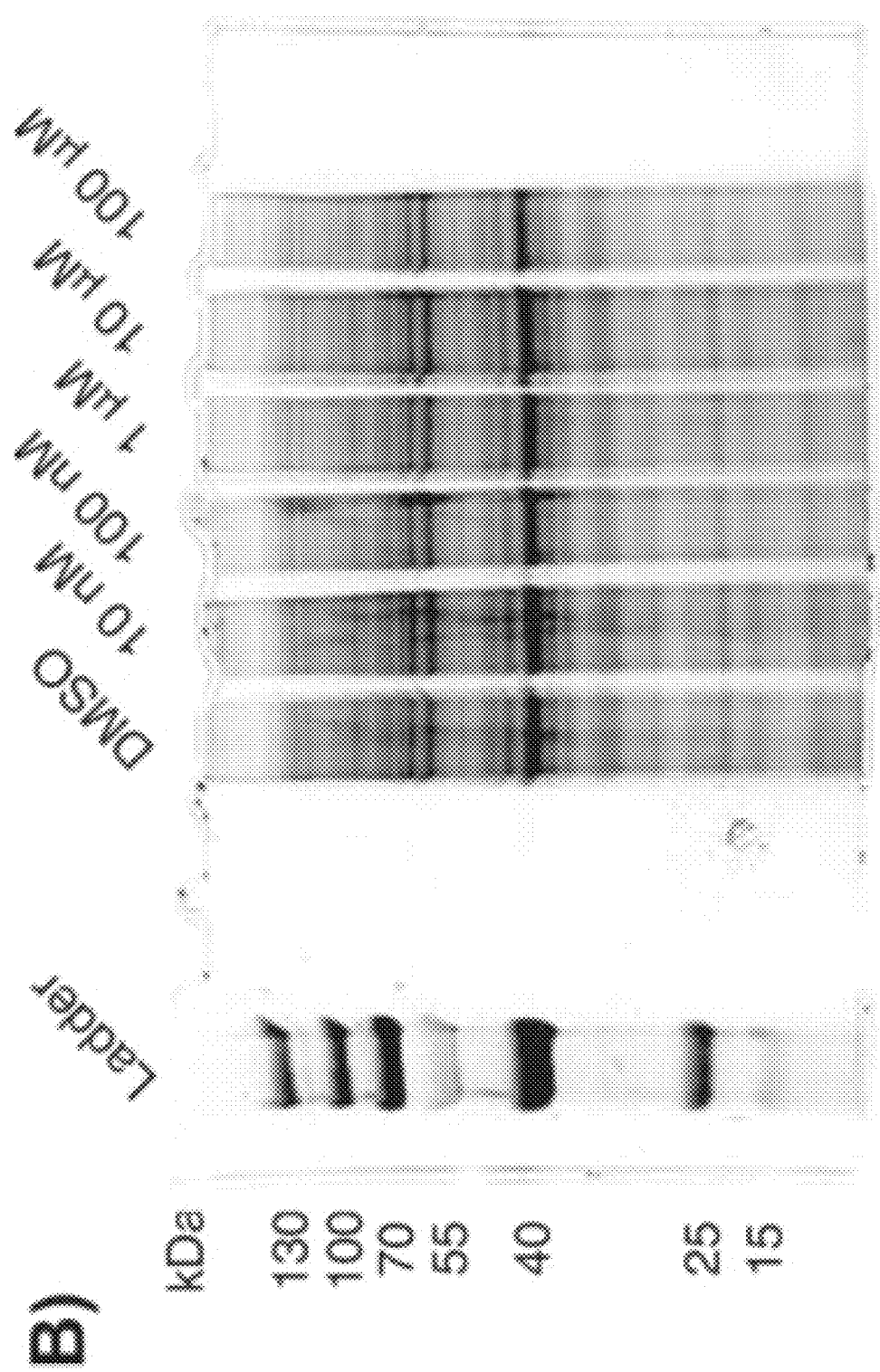
Figure 6:
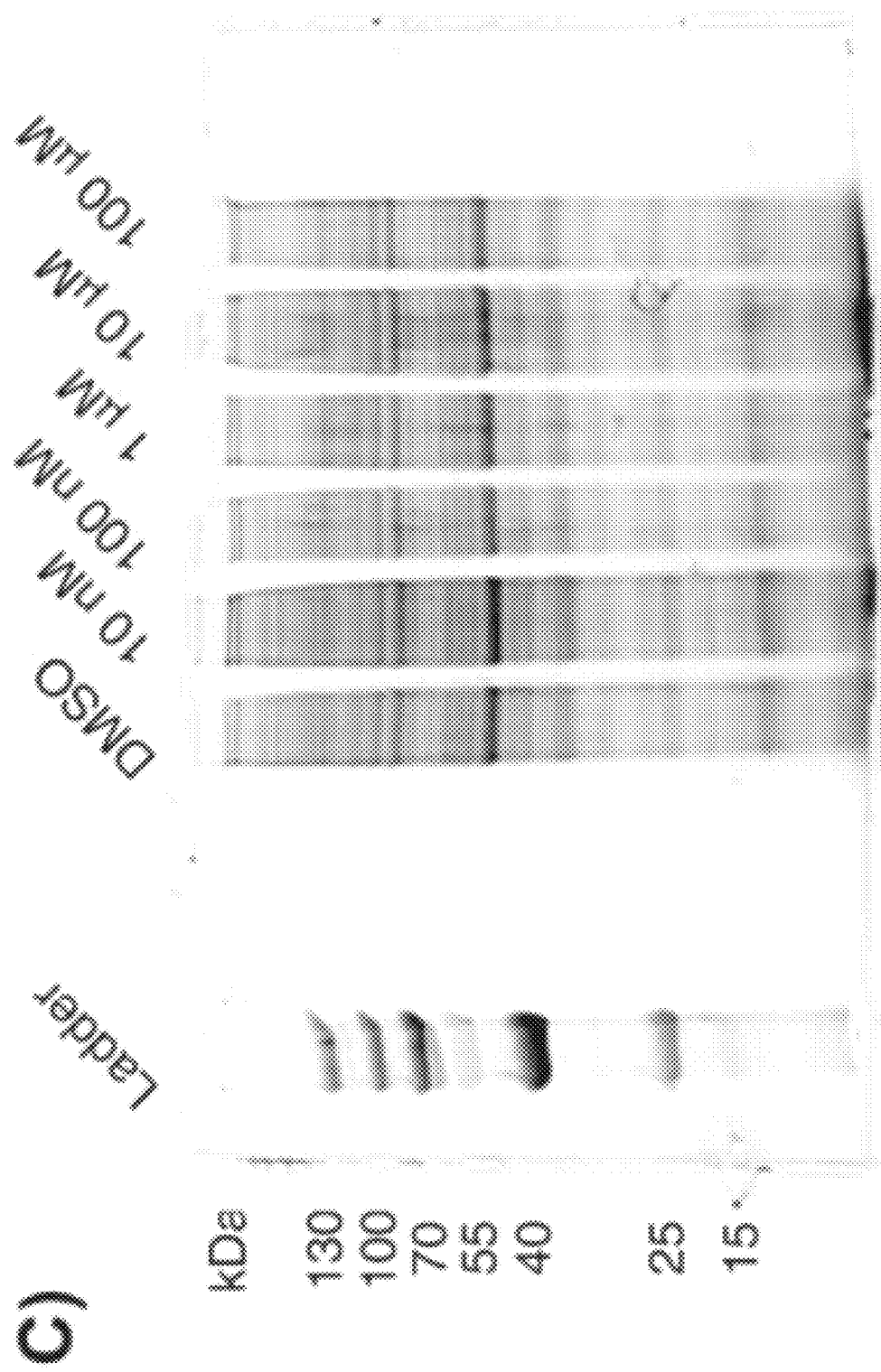
Figure 7:
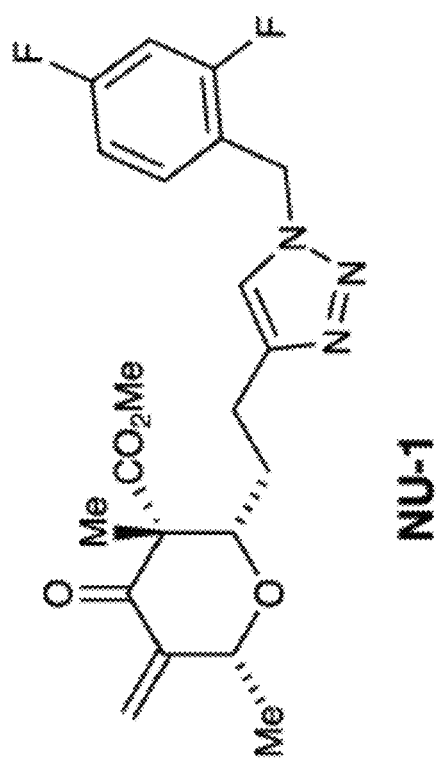
FIG. 7: Experimental in vitro drug properties of NU-1
Figure 8:
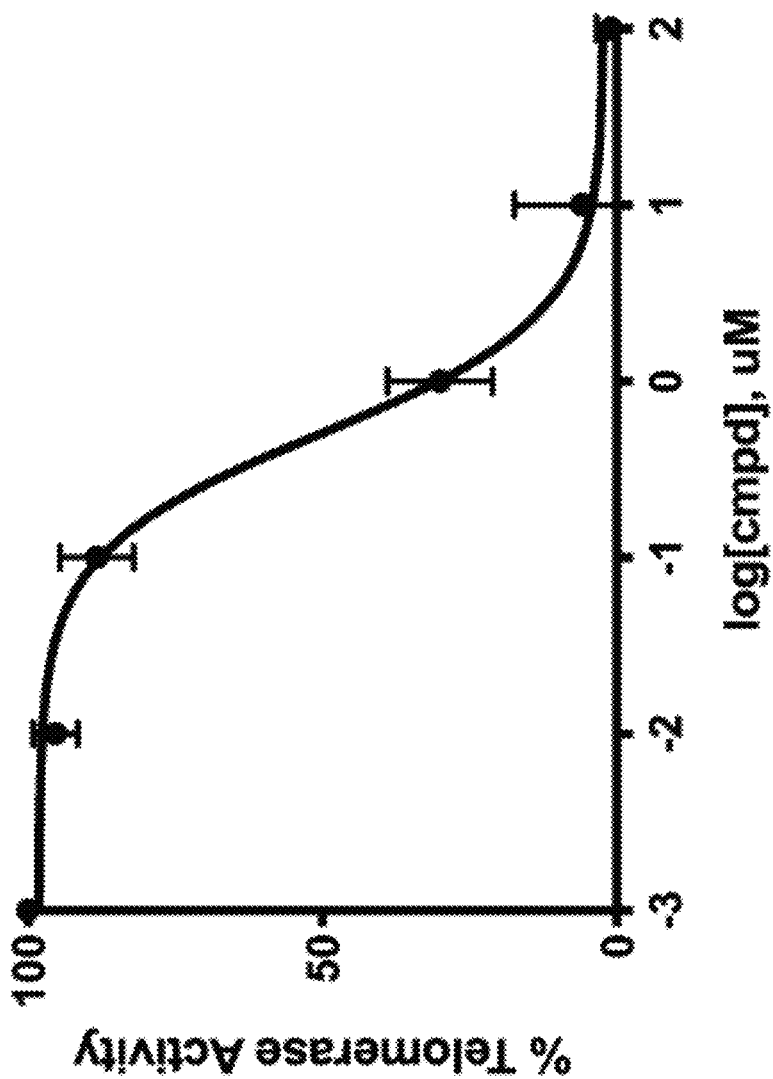
FIG. 8: IC$_{50}$ curve of chrolactomycin measured in MCF-7 cell lysates. IC$_{50}$=0.5 μM.
Figure 8:
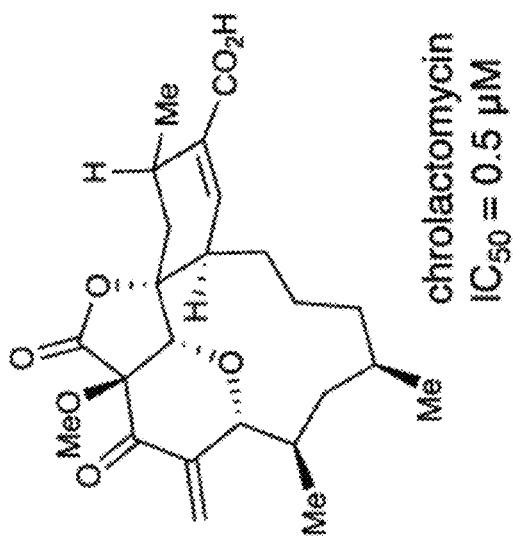
Figure 9:
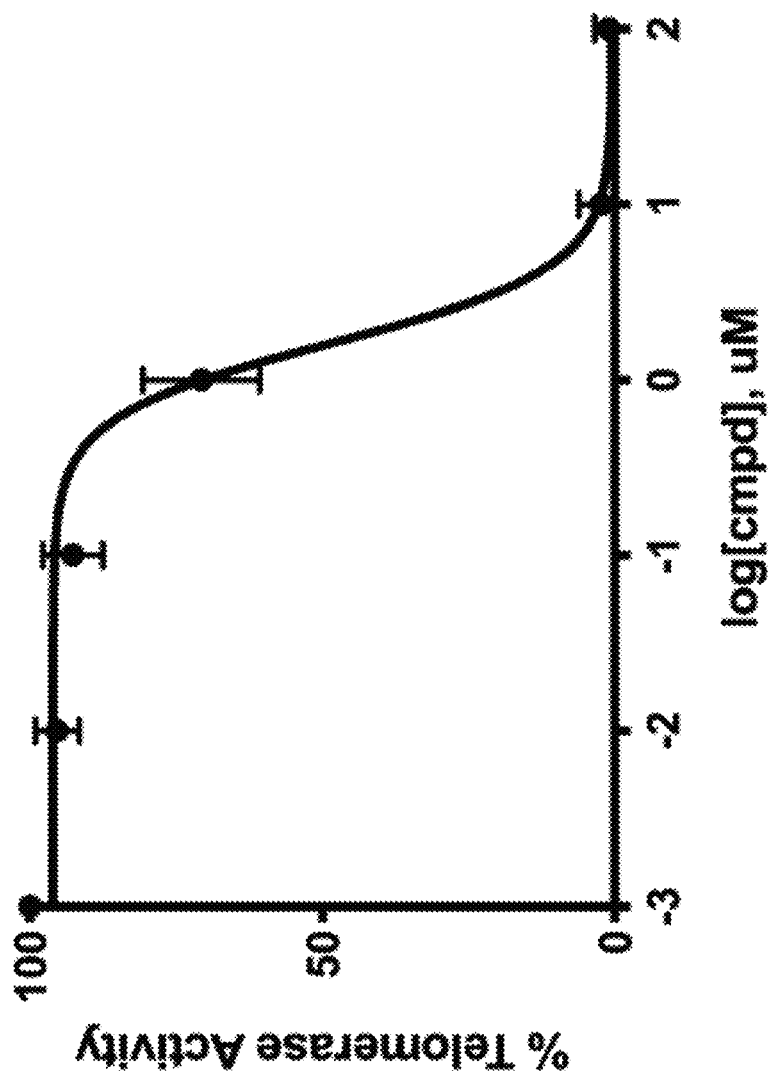
FIG. 9: IC$_{50}$ curve of okilactomycin measured in MCF-7 cell lysates. IC$_{50}$=2.1 μM.
Figure 9:
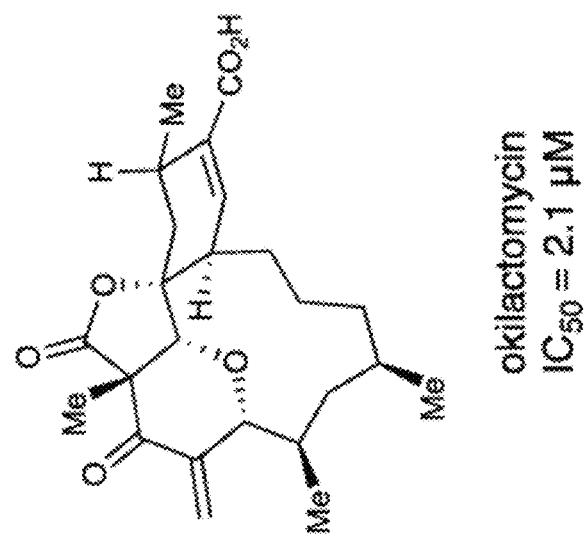
Figure 10:
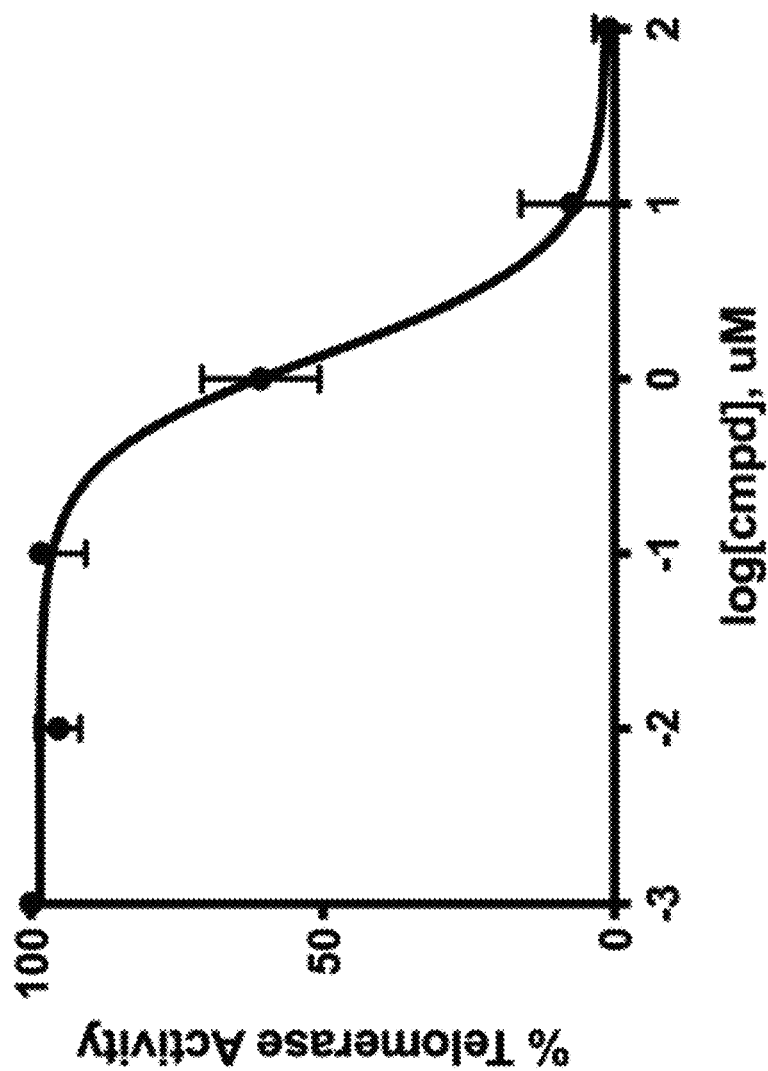
FIG. 10: IC$_{50}$ curve of racemic 4a measured in MCF-7 cell lysates. IC$_{50}$=1.5 μM.
Figure 10:
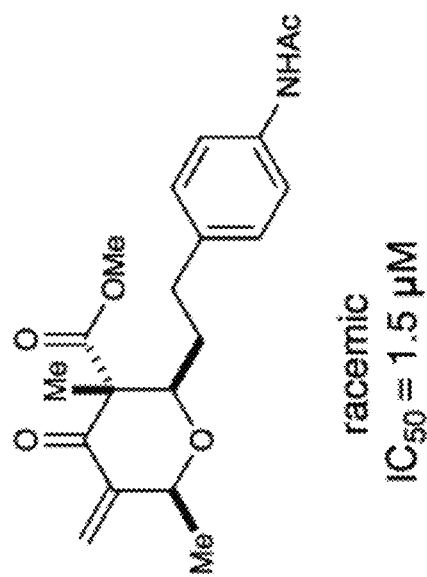
Figure 11:
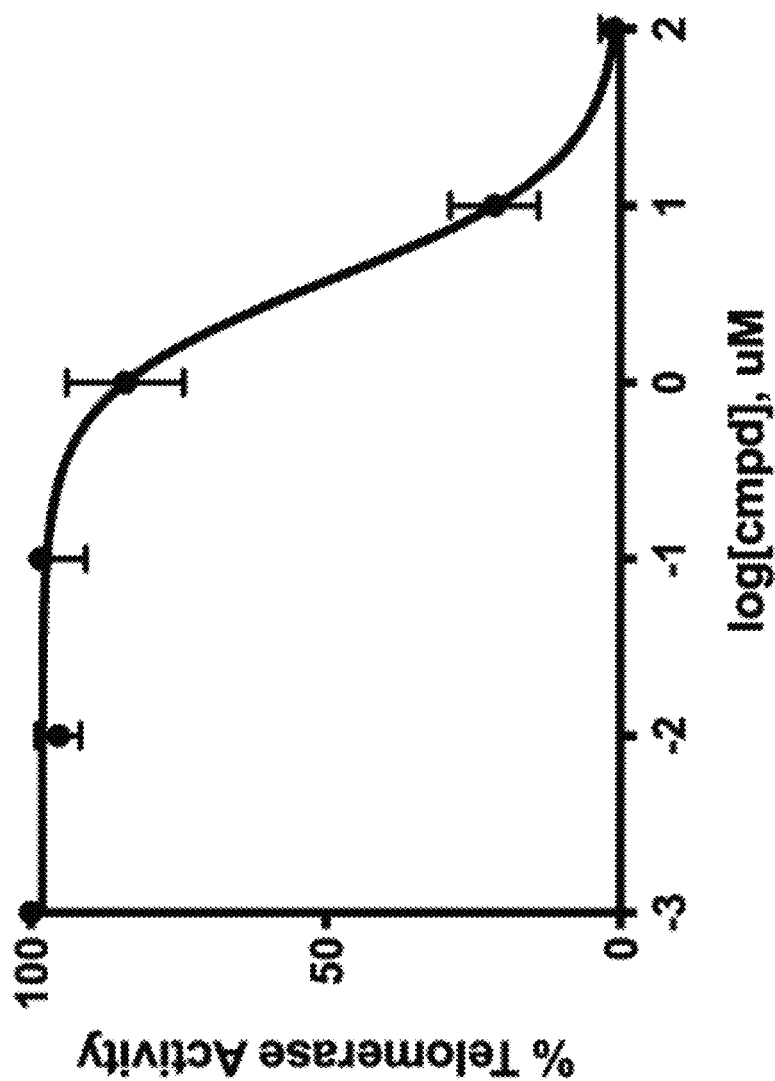
FIG. 11: IC$_{50}$ curve of enantiopure 4a measured in MCF-7 cell lysates. IC$_{50}$=4.5 μM.
Figure 11:
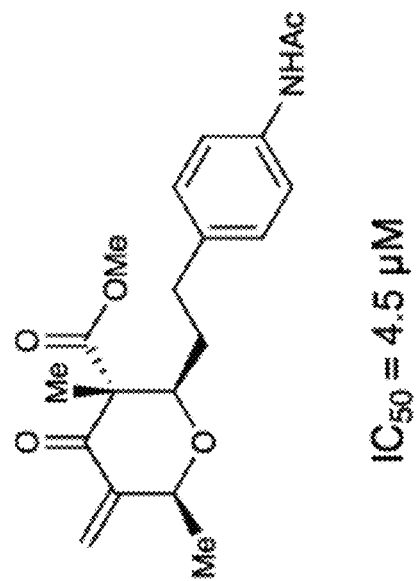
Figure 12:
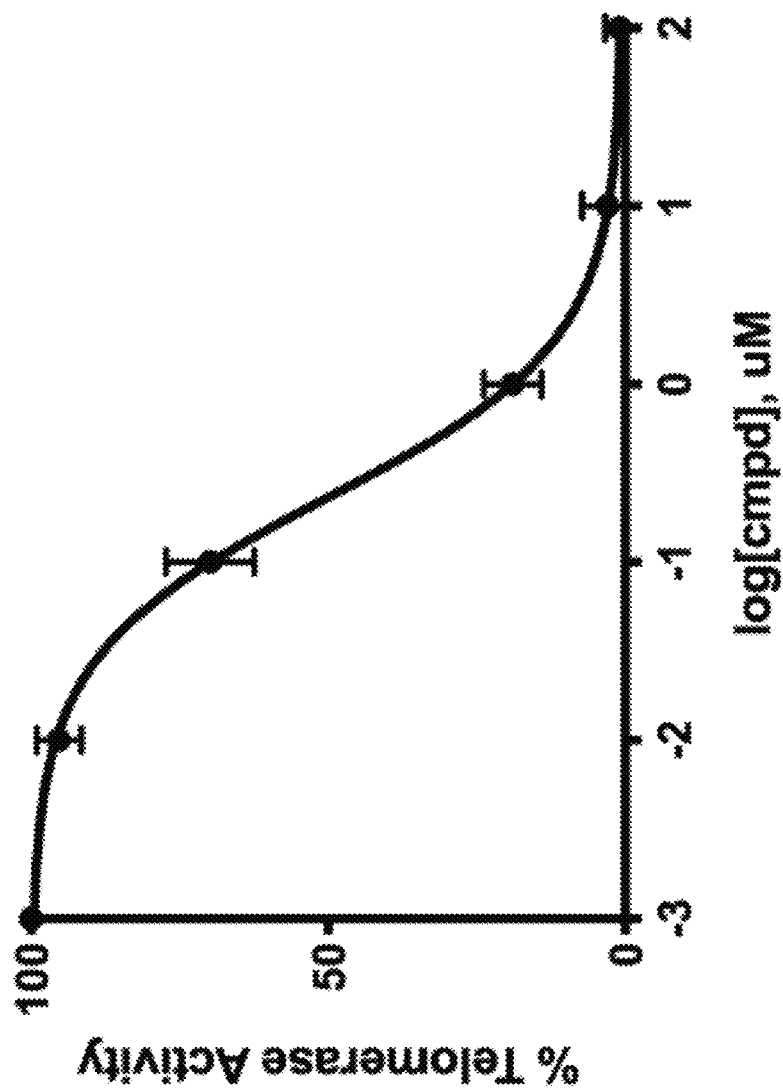
FIG. 12: IC$_{50}$ curve of enantiopure 4a measured in MCF-7 cell lysates. IC$_{50}$=0.9 μM.
Figure 12:
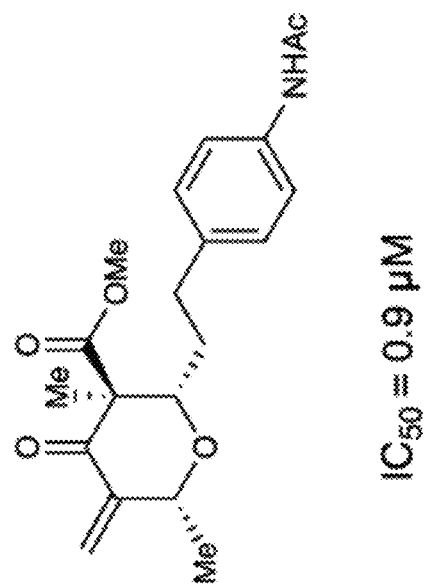

Briefly, the MCF-7 proteome was dose-response treated with NU-1 or chrolactomycin (10 nM to 100 µM) for 1 hr, followed by treatment with a thiol reactive fluorescein-iodoacetamide (10 µM, 1 hr). The reactions were then quenched, separated by SDS-PAGE, and fluorescein-labeled proteins were detected by in-gel fluorescence scanning. Notably, we observed minimal loss of protein banding and streaking, where loss of protein banding is indicative of NU-1 and chrolactomycin having off-target reactivity and labeling proteins prior to fluoescein-iodoacetamide labeling (FIG. 6A-C).

CONCLUSIONS

A new and effective class of telomerase inhibitors has been developed inspired by the natural product chrolactomycin, a covalent inhibitor of human telomerase reverse transcriptase (hTERT) catalytic activity. Rational compound design resulted in the lead compound NU-1, a simplified analogue accessible in four synthetic steps that binds to hTERT and directs an exomethylene group to react with an active-site cysteine, leading to irreversible enzyme inhibition. Despite concerns about potential reactivity with cellular nucleophiles, NU-1 had negligible effects on telomerase-negative cancer cells, and has shown to have comparable thiol reactivity to known targeted covalent inhibitors. This study provides proof-of-principle for sensitive, covalent chemical probes to dissect telomerase functions in cells and lead compounds to validate hTERT as a target to enhance conventional genotoxic cancer therapies.

Methods

General Information. Chrolactomycin was isolated from Actinomycete Actinospica (NAICONS Laboratory, Milan Italy). The telomerase inhibitors BIBR1532, MST-312, costunolide and helenalin were purchased from Sigma Aldrich and used without further purification. All cell lines used were purchased from ATCC (MCF-7, MDA-MB-231, A549, HeLa, ACHN, Saos-2, VA-13) and tested for mycoplasma every six months. All cell lines were cultured according to the manufacturer's instructions at 37° C. in 5% CO2.

In-silico studies. Utilizing the ligand based enumeration techniques implemented in Pipeline pilot platform[107] for library generation and considering a truncated version of chrolactomycin as the reference ligand 10,000 drug-like structures had been generated. These structures had been filtered out using the PAINS filiters[108] and 330 structures were selected for covalent docking studies. The CovDock[109] (covalent docking) module available in Schrodinger suite has five distinct steps involved in the docking process of the ligand and the protein of interest. The steps involved are i) non-covalent docking; ii) receptor sampling; iii) covalent bond formation; iv) refinement; and v) apparent affinity scoring. Furthermore, CovDock also has two sub-modules such as CovDock-Screen and CovDock-Thorough which is coupled with the binding energy computation using MM-GBSA[110] (Molecular Mechanical Generalized Born Surface Area Continuum Solvent Approach).

Ligand preparation: All the 330 filtered structures were subjected to ligand preparation panel available in Schrodinger at pH=7.4±1 to obtain best initial geometry for all the structures. The ligands van der Waals radii were scaled to 0.8 Å with partial atomic charges <0.15 esu.

Grid generation: The docking engine Glide available in Schrodinger has been built upon grid based techniques. In order to generate a grid box, we considered the apo TERT structure available in protein database with the accession code 3DU5. Before generating the grid box, the protein structure was processed through the protein preparation module in order to correct irrelevant side chains, added missing atoms, eliminated partial occupant rotamers, fixed the undesired orientation of Asn, Gln and His residues, and finally replaced the "b" values by the optimized potential for liquid simulations (OPLS3) charges.[111] Since this was an apo structure, we applied the SiteMap algorithm[112] to identify putative small molecule ligand binding pocket. After identifying the ligand binding site a grid box of 10×10×10 Å was constructed which contained the reactive C390 residue along with few critical residues such as K189, K249, K372, and K406.

CovDock: The very first step in CovDock was to define the type of chemical reaction that would occur in between the reactive residue and the ligand. We selected Michael Addition as the chemical reaction and the engine identified the atom in the electrophile of the ligand set where the reaction had to occur. Then the reactive residue C390 was selected and CovDock-Screen engine was used to screen the ligand set. This screening resulted in 200 hits and we then carried out CovDock-Thorough to these hits in order to compute the binding energy using MMGBSA. Based on the binding energy and the docked poses 150 structures were selected for synthetic effort.

Protease Digestion and Mass Spectrometry Analysis. tcTERT (50 µg, ~600 pmol) was treated with chrolactomycin, NU-1, helenalin, costunolide or DMSO for 1 hr at 37° C. The reaction was diluted with ammonium bicarbonate buffer (pH 8.0), then reduced for 30 min at 56° C. with 10 mM DTT. After cooling to 23° C., the protein was alkylated with 25 mM iodoacetamide for 30 min at 23° C. in the dark, followed by trypsin digestion (2.5 µg, Promega) overnight at 37° C. Digested peptides (~2 pmol) were injected onto a self-packed precolumn (4 cm POROS10R2) and eluted into the mass spectrometer (LTQ Orbitrap Velos, Thermo Fisher). Peptides were subjected to $MS^2$ by CAD (electron multiplier detection, relative collision energy 35%, q=0.25).

Telomeric Repeat Amplification Protocol Assay. The telomeric repeat amplification protocol (TRAP) assay was performed using the TRAPeze RT Telomerase Detection Kit (EMD Millipore) and iTaq DNA polymerase (Bio-Rad) according to the manufacturer's protocol.

Cell Lysate TRAP Analysis. MCF-7, HeLa, ACHN, MDA-MB231 and A549 cells were cultured in DMEM media supplemented with 10% Fetal Bovine Serum (FBS), 1% pen/strep and with 5% CO2 and 37° C. Cells were plated in 2×T75 flasks and cultured for 3 days. Flasks were rinsed twice with PBS and treated with 0.05% trypsin-EDTA (Thermo Fisher) to detach cells. The cell suspension was washed twice in PBS and the cell pellet was resuspended in 200 µl of 1×CHAPS Lysis Buffer (10 mM Tris-HCl, pH 7.5; 1 mM $MgCl_2$; 1 mM EGTA; 0.1 mM benzamidine; 5 mM β-mercaptoethanol; 0.5% CHAPS; 10% glycerol)/$10^6$ cells, and incubated on ice for 30 min. Cell extracts were transferred to microcentrifuge tubes, 200 µl/tube, and centrifuged at 12,000×g for 20 min at 4° C. to remove cell debris. Stock solutions of compounds were made in DMSO with a concentration of 100 mM and a 6-fold dilution was performed in DMSO in a 96-well plate to produce compound solutions of 100, 10, 1, 0.1, 0.01, and 0.001 mM (1000× of the final concentration). The 1000× stock solutions of the compound samples were transferred to a 96-well plate using the Echo 550 (Labcyte) and then diluted with the cell extracts to yield final compound concentrations of 100, 10, 1, 0.1, 0.01, and 0.001 µM. The plate was covered and shaken at room temperature for 30 min. For TRAPeze reactions, a "master mix" was prepared according to the TRAPeze protocol, containing 5 µl of the TRAPeze reaction mix; 0.4 µl Taq polymerase; 17.6 µl PCR grade, nuclease-free water. The master mix and treated cell extracts were transferred using the Mosquito Crystal Liquid Handling System (TTP Labtech) into separate wells in a white, 384-well RT-PCR plate. Each well contained 1.2 µl of the master mix and 1.2 µl of the treated cell extract to give a final volume of 2.4 µl, with two duplicates for each sample. The RT-PCR plate was then sealed and centrifuged for 5 min. A sample containing only CHAPS Lysis Buffer was included as negative control. The TSR8 standards were included to generate a standard curve. Samples were amplified in a CFW384 RT-PCR (BioRad) detection system with PCR parameters of 30 min at 30° C. for 1 cycle, 2 min at 95° C. for 1 cycle, and then 45 cycles of 15 s at 94° C., 60 s at 59° C., and 10 s at 45° C. Real-time fluorescent data was obtained during the 10 s at 45° C. step. The number of cycles at which the fluorescence level reached a threshold (Ct) was averaged between the duplicates for each sample. Using a calibration curve obtained from the TSR8 standards, a linear equation was obtained to convert the Ct values into arbitrary telomerase activity units, which were plotted as a function of compound concentration to construct dose-response curves and calculate IC50.

Cultured Cells TRAP Analysis. MCF-7, HeLa, ACHN, MDA-MB231 and A549 cells were cultured in DMEM media supplemented with 10% Fetal Bovine Serum (FBS), 1% pen/strep and with 5% CO2 and 37° C. Cells were plated in 96 well plates and allowed to attach for 24 h. Media was removed, and fresh media containing various concentrations of compound was added, and the plate was incubated for 24 h. Media was removed, the cells were washed 2 times with PBS, and the cells were lysed in 20 µl of 1× CHAPS Lysis Buffer (10 mM Tris-HCl, pH 7.5; 1 mM MgCl2; 1 mM EGTA; 0.1 mM benzamidine; 5 mM β-mercaptoethanol; 0.5% CHAPS; 10% glycerol). The cell extract was then centrifuged at 12,000×g for 20 min at 4° C. to remove cell debris. Note: "fresh" media constitutes media supplemented with 10% Fetal Bovine Serum (FBS) and 1% pen/strep that has not been previously used for cell culture (e.g., not conditioned media). TRAP analysis was conducted as above.

Compound Washout TRAP analysis. MCF-7 cells were plated in 96 well plates and allowed to attach for 24 h. Media was removed, and fresh media containing various concentrations of compound was added, and the plate was incubated for 24 h. Media was removed, cells were washed 2 times with PBS, and fresh media without compound was added. Cells were incubated at 37° C. for an additional "X" hours. Media was removed, the cells were washed 2× with PBS, and the cells were lysed in 20 µl of 1× CHAPS Lysis Buffer (10 mM Tris-HCl, pH 7.5; 1 mM MgCl2; 1 mM EGTA; 0.1 mM benzamidine; 5 mM β-mercaptoethanol; 0.5% CHAPS; 10% glycerol). The cell extract was then centrifuged at 12,000 g for 20 min at 4° C. to remove cell debris. Note: "fresh" media constitutes media supplemented with 10% Fetal Bovine Serum (FBS) and 1% pen/strep that has not been previously used for cell culture (e.g., not conditioned media"). TRAP analysis was conducted as above.

Cell Viability Measurements. MCF-7, HeLa, MDA-MB231 and A549 cells were cultured in DMEM media supplemented with 10% Fetal Bovine Serum (FBS), 1% pen/strep and with 5% CO2 and 37° C. Cells were plated in 96 well plates and allowed to attach for 24 h. Media was removed, and fresh media containing various concentrations of compound was added, and the plate was incubated for 24 h. The plate was removed from the incubator and allowed to equilibrate to room temperature for 30 min. 50 µl of freshly prepared CellTiter-Glo (Promega) reagent was added, and the plate was mixed on an orbital shaker for 10 min to induce cell lysis and stabilize luminescent signal. The luminescence was recorded on a PerkinElmer Enspire multimode plate reader.

Compound Washout Cell Viability Measurements. MCF-7 cells were plated in 96 well plates and allowed to attach for 24 h. Media was removed, and fresh media containing various concentrations of compound was added, and the plate was incubated for 24 h. Media was removed, cells were washed 2 times with PBS, and fresh media without compound was added. Cells were incubated at 37° C. for an additional "X" h and analyzed as above. Note: "fresh" media constitutes media supplemented with 10% Fetal Bovine Serum (FBS) and 1% pen/strep that has not been previously used for cell culture (e.g., not conditioned media).

Primer-Extension Telomerase Activity Assays. Telomerase activity assays were performed as previously described." Experiments in FIGS. 4A and 4B utilized telomerase immunopurified with the hTERT antibody as described in the reference above; telomerase stock solution was at ~10 nM in "telomerase buffer": 50 mM HEPES-KOH (pH 8); 300 mM KCl; 2 mM MgCl$_2$; 10% v/v glycerol; 0.1% v/v Triton X-100; 1 mM DTT.

For FIG. 4A, extension reactions were performed in a total volume of 100 µL. NU-1 or NU-2 were prepared in DMSO at 20× final concentration (2000 µM, 200 µM, or 20 µM). 5 µL of DMSO or the respective compound/DMSO dilution was placed in a tube, followed by 45 µL of a solution containing: 2.2 mM MgCl$_2$; 1.1 mM DTT; 2.2 mM dTTP, 2.2 mM dATP, 22 µM dGTP, ~5 µCi α-$^{32}$P-dGTP (Perkin Elmer), and the DNA substrate 5'-biotin-CTAGACCTGT-CATCA(TTAGGG)$_3$-3' (SEQ ID NO: 1) (2.2 µM). Reactions were initiated by addition of 50 µL telomerase solution, providing final concentrations of: ~5 nM telomerase; 25 mM HEPES-KOH; 150 mM KCl; 2 mM MgCl$_2$; 0.05% v/v Triton X-100; 5% v/v glycerol; 1 mM DTT; 5% v/v DMSO; 1 mM dATP/dTTP; 10 µM dGTP. Reactions were incubated at 37° C. for 8 h, then quenched with addition of 400 µL STOP solution: 10 mM Tris-HCl (pH 7.5); 2 M NaCl; 1 mM EDTA; ~5,000 cpm 5'-α-$^{32}$P-(CTAGACCTGTCATCA)$_2$-biotin-3' (SEQ ID NO: 3) (recovery/loading control). Solutions were incubated with 30 µL Dynabeads M-280 Streptavidin suspension (Thermo-Fisher, suspension used as is) with rotation overnight. Beads were recovered by Dynamagnet and washed twice with 500 µL [10 mM Tris-HCl (pH 7.5); 2 M NaCl; 1 mM EDTA]; followed by 300 µL [10 mM Tris-HCl (pH 7.5); 1 mM EDTA]. Beads were suspended in 30 µL [9:1 v/v Formamide/TBE:D-biotin solution (5 mM in TE)]. Samples were denatured at 80° C. for 10 min, and the product solutions recovered on the Dynamagnet. Products (6 µL) were electrophoresed over a 10% denaturing acrylamide/8 M urea gel at 75 Watts until bromophenol blue was ~¾ down the gel (~50 min).

For FIG. 4B, two 500 µL binding reactions were prepared, each containing a 25 µL aliquot of either NU-1 or NU-2 (2 mM stock in DMSO=100 µM final concentration) and ~10 nM telomerase in telomerase buffer. Immediately upon mixing (t=0), and at t=10, 20, 40, 60, 120, 240, and 360 min, 50 µL of each reaction was combined with 50 µL extension mix [2 mM MgCl$_2$, 1 mM DTT, 2 mM dTTP, 2 mM dATP, 20 µM dGTP, ~5 µCi α-$^{32}$P-dGTP (Perkin Elmer), and the DNA substrate 5'-biotin-CTAGACCTGTCATCA (TTAGGG)$_3$-3' (SEQ ID NO: 1) (2 µM)]. All reactions were incubated at 37° C. overnight, and then processed as described above.

For FIG. 4C, the control or treated cells were prepared and collected as pellets of 5×10$^6$ cells each at NW and pellets were shipped to CMRI on dry ice. Frozen cell pellets were thawed on wet ice and suspended in 1 mL telomerase buffer supplemented with 1 mM PMSF. Endogenous telomerase was immunopurified and assayed as described.

CYP450 Inhibition Assay. Assay was conducted using the commercially available Vivid CYP1A2 Screening Kit (Thermo Fisher) according to the manufacturer's protocol. α-napthoflavone and DMSO were used as a positive and negative control respectively based on the manufacturer's protocol.

Non-Cell-Based Assay for Drug Transport (PAMPA assay). Assay was conducted using the commercially available parallel artificial membrane permeation assay (PAMPA, Millipore Sigma) according to the manufacturer's protocol.

Liver Microsomal Stability Assay. Assay was conducted using the Corning UltraPool HLM 150 Mixed Gender microsomal kit (Corning Life Sciences) according to the manufacturer's protocol.

N-Acetyl Cysteine, N-Acetyl Lysine and N-Acetyl Serine Kinetic Studies. Assay was conducted as described with minor modifications.[81-84] Briefly, a 1 mM stock solution of NU-1 with internal standard (phenacetin) in DMSO was added to a 50 mM solution of either N-acetyl cysteine, N-acetyl lysine or N-acetyl serine in 67 mM phosphate buffer (pH 7.4), as well as added to a solution of 67 mM phosphate buffer (pH 7.4) control. Samples were taken every 2 min for 2 h and quenched immediately with MeOH and centrifuged upon sampling. Samples were placed on a Waters Acquity UPLC-MS system and measured for the ratio of NU-1 to internal standard intensity to calculate the amount of NU-1 present at each time point relative to the amount of NU-1 at the first injection of the compound in buffer. Assay was conducted in triplicate.

Schiff-Base Measurement. A 1 mM stock solution of NU-1 in DMSO-d$_6$ was added to a solution of 5 mM solution of glycine in D$_2$O in an NMR tube. The mixture was analyzed by $^1$H NMR over 48 hours to analyze formation of Schiff-bases with the ketone of NU-1.

Kinetic Solubility Measurements of NU-1. Solubility readings were taken on a Synergy HTX plate reader using a 384 well plate format. Total volume of solution 50 µl with a final DMSO concentration at 1% v/v in PBS. Solubility curve was established using concentration ranges from 1-500 µM that were prepared by serial dilution of NU-1 (50 mM in DMSO). Measurements were made in triplicate.

Competitive Gel Image Analysis. MCF-7 cells were cultured in DMEM media supplemented with 10% Fetal Bovine Serum (FBS), 1% pen/strep and with 5% CO2 and 37° C. Cells were plated cultured for 3 days. Flasks were rinsed twice with PBS and treated with 0.05% trypsin-EDTA (Thermo Fisher) to detach cells. The cell suspension was washed twice in PBS and the cell pellet was resuspended in 200 µl of M-PER extraction reagent (Thermo Fisher)/10$^6$ cells, and incubated for 30 min. Cell extracts were transferred to microcentrifuge tubes, 200 µl/tube, and centrifuged at 12,000×g for 20 min to remove cell debris. The corresponding lysate was then further diluted to a total protein concentration of 2 mg/mL as measured by Nanodrop (Thermo Fisher). 48 µL of MCF-7 lysate was added to twelve microcentrifuge tubes (six per compound), followed by treatment of cell lysate with 1 µL solution of NU-1/chrolactomycin (equating to doses ranging from 10 nM to 100 µM). The samples were incubated for 1 hr, followed by addition of 1 µl of 5-iodoacetamido-fluorescein to a final concentration of 10 µM. The samples were again incubated for 1 hr, followed by quenching the reaction with 15 µL NuPAGE LDS Sample Buffer (4×). The samples were heated in a water bath at 70° C. for 10 minutes, followed by loading 30 µL of the samples onto a 10% NuPAGE Bis-Tris gel with 20 µl of a 2:1 mixture of PageRuler Prestained protein ladder (Thermo Fisher). SDS-page was ran for 30 min at constant voltage (250 V) using a Mini Gel Tank (Thermo Fisher) and a PowerEase 300W (Thermo Fisher) power supply. Upon completion, the gels were removed from their cases, rinsed in DI water for 5 minutes, and imaged using a IBright FL1000 imager (Thermo Fisher).

REFERENCES (1). Moyzis, R. K., Buckingham, J. M., Cram, L. S., Dani, M., Deaven, L. L., Jones, M. D., Meyne, J., Ratliff, R. L., and Wu, J. R. (1988) A highly conserved repetitive DNA sequence, (TTAGGG)n, present at the telomeres of human chromosomes, Proc Natl Acad Sci USA 85, 6622-6626.

(2). de Lange, T. (2005) Shelterin: the protein complex that shapes and safeguards human telomeres, Genes Dev 19, 2100-2110.

(3). de Lange, T. (2018) Shelterin-Mediated Telomere Protection, Annu. Rev. Genet. 52, 223-247.

(4). Hayflick, L., and Moorhead, P. S. (1961) The serial cultivation of human diploid cell strains, Exp. Cell. Res. 25, 585-621.

(5). Hayflick, L. (1965) The limited in vitro lifetime of human diploid cell strains, Exp. Cell. Res. 37, 614-636.

(6). Harley, C. B., Futcher, A. B., and Greider, C. W. (1990) Telomeres Shorten during Aging of Human Fibroblasts, Nature 345, 458-460.

(7). Greider, C. W., and Blackburn, E. H. (1985) Identification of a specific telomere terminal transferase activity in tetrahymena extracts, Cell 43, 405-413.

(8). Greider, C. W., and Blackburn, E. H. (1987) The telomere terminal transferase of tetrahymena is a ribonucleoprotein enzyme with two kinds of primer specificity, Cell 51, 887-898.

(9). Greider, C. W., and Blackburn, E. H. (1989) A Telomeric Sequence in the Rna of Tetrahymena Telomerase Required for Telomere Repeat Synthesis, Nature 337, 331-337.

(10). Lingner, J., Hughes, T. R., Shevchenko, A., Mann, M., Lundblad, V., and Cech, T. R. (1997) Reverse Transcriptase Motifs in the Catalytic Subunit of Telomerase, Science 276, 561-567.

(11). Nakamura, T. M., Morin, G. B., Chapman, K. B., Weinrich, S. L., Andrews, W. H., Lingner, J., Harley, C. B., and Cech, T. R. (1997) Telomerase catalytic subunit homologs from fission yeast and human, Science 277, 955-959.

(12). Feng, J., Funk, W. D., Wang, S. S., Weinrich, S. L., Avilion, A. A., Chiu, C. P., Adams, R. R., Chang, E., Allsopp, R. C., Yu, J., and al, e. (1995) The RNA component of human telomerase, Science 269, 1236-1241.

(13). Weinrich, S. L., Pruzan, R., Ma, L. B., Ouellette, M., Tesmer, V. M., Holt, S. E., Bodnar, A. G., Lichtsteiner, S., Kim, N. W., Trager, J. B., Taylor, R. D., Carlos, R., Andrews, W. H., Wright, W. E., Shay, J. W., Harley, C. B., and Morin, G. B. (1997) Reconstitution of human telomerase with the template RNA component hTR and the catalytic protein subunit hTRT, Nat. Genet. 17, 498-502.

(14). Beattie, T. L., Zhou, W., Robinson, M. O., and Harrington, L. (1998) Reconstitution of human telomerase activity in vitro, Curr. Biol. 8, 177-180.

(15). Wright, W. E., Piatyszek, M. A., Rainey, W. E., Byrd, W., and Shay, J. W. (1996) Telomerase activity in human germline and embryonic tissues and cells, Dev Genet 18, 173-179.

(16). Kim, N. W., Piatyszek, M. A., Prowse, K. R., Harley, C. B., West, M. D., Ho, P. L. C., Coviello, G. M., Wright, W. E., Weinrich, S. L., and Shay, J. W. (1994) Specific Association of Human Telomerase Activity with Immortal Cells and Cancer, Science 266, 2011-2015.

(17). Park, J.-I., Venteicher, A. S., Hong, J. Y., Choi, J., Jim, S., Shkreli, M., Chang, W., Meng, Z., Cheung, P., Ji, H., McLaughlin, M., Veenstra, T. D., Nusse, R., McCrea, P. D., and Artandi, S. E. (2009) Telomerase modulates Wnt signalling by association with target gene chromatin, Nature 460, 66-72.

(18). Ghosh, A., Saginc, G., Leow, S. C., Khattar, E., Shin, E. M., Yan, T. D., Wong, M., Zhang, Z., Li, G., Sung, W.-K., Zhou, J., Chng, W. J., Li, S., Liu, E., and Tergaonkar, V. (2012) Telomerase directly regulates NF-κB-dependent transcription, Nat. Cell Biol. 14, 1270.

(19). Holt, S. E., Glinsky, V. V., Ivanova, A. B., and Glinsky, G. V. (1999) Resistance to apoptosis in human cells conferred by telomerase function and telomere stability, Mol. Carcinog. 25, 241-248.

(20). Bermudez, Y., Erasso, D., Johnson, N. C., Alfonso, M. Y., Lowell, N. E., and Kruk, P. A. (2006) Telomerase confers resistance to caspase-mediated apoptosis, Clin Intery Aging 1, 155-167.

(21). Sharma, G. G., Gupta, A., Wang, H., Scherthan, H., Dhar, S., Gandhi, V., Iliakis, G., Shay, J. W., Young, C. S. H., and Pandita, T. K. (2003) hTERT associates with human telomeres and enhances genomic stability and DNA repair, Oncogene 22, 131-146.

(22). Masutomi, K., Possemato, R., Wong, J. M. Y., Currier, J. L., Tothova, Z., Manola, J. B., Ganesan, S., Lansdorp, P. M., Collins, K., and Hahn, W. C. (2005) The telomerase reverse transcriptase regulates chromatin state and DNA damage responses, Proc. Natl. Acad. Sci. U.S.A. 102, 8222-8227.

(23). Doksani, Y., and de Lange, T. (2014) The role of double-strand break repair pathways at functional and dysfunctional telomeres, Cold Spring Harb Perspect Biol 6, a016576-a016576.

(24). Perera, 0. N., Sobinoff, A. P., Teber, E. T., Harman, A., Maritz, M. F., Yang, S. F., Pickett, H. A., Cesare, A. J., Arthur, J. W., MacKenzie, K. L., and Bryan, T. M. (2019) Telomerase promotes formation of a telomere protective complex in cancer cells, Sci. Adv. 5, DOI: 10.1126/sciadv.aav409

(25). Rezler, E. M., Bearss, D. J., and Hurley, L. H. (2002) Telomeres and telomerases as drug targets, Curr. Opin. Pharmacol. 2, 415-423.

(26). Neidle, S., and Parkinson, G. (2002) Telomere maintenance as a target for anticancer drug discovery, Nat. Rev. Drug Discov. 1, 383-393.

(27). Ouellette, M. M., Wright, W. E., and Shay, J. W. (2011) Targeting telomerase-expressing cancer cells, J. Cell. Mol. Med. 15, 1433-1442.

(28). Sekaran, V., Soares, J., and Jarstfer, M. B. (2014) Telomere maintenance as a target for drug discovery, J. Med. Chem. 57, 521-538.

(29). Arndt, G. M., and MacKenzie, K. L. (2016) New prospects for targeting telomerase beyond the telomere, Nat. Rev. Canc. 16, 508.

(30). Damm, K., Hemmann, U., Garin-Chesa, P., Hauel, N., Kauffmann, I., Priepke, H., Niestroj, C., Daiber, C., Enenkel, B., Guilliard, B., Lauritsch, I., Müller, E., Pascolo, E., Sauter, G., Pantic, M., Martens, U. M., Wenz, C., Lingner, J., Kraut, N., Rettig, W. J., and Schnapp, A. (2001) A highly selective telomerase inhibitor limiting human cancer cell proliferation, The EMBO Journal 20, 6958-6968.

(31). Pascolo, E., Wenz, C., Lingner, J., Hauel, N., Priepke, H., Kauffmann, I., Garin-Chesa, P., Rettig, W. J., Damm, K., and Schnapp, A. (2002) Mechanism of Human Telomerase Inhibition by BIBR1532, a Synthetic, Non-nucleosidic Drug Candidate, J. Biol. Chem. 277, 15566-15572.

(32). El-Daly, H., Kull, M., Zimmermann, S., Pantic, M., Waller, C. F., and Martens, U. M. (2005) Selective cytotoxicity and telomere damage in leukemia cells using the telomerase inhibitor BIBR1532, Blood 105, 1742-1749.

(33). Mueller, S., Hartmann, U., Mayer, F., Balabanov, S., Hartmann, J. T., Brummendorf, T. H., and Bokemeyer, C.

(2007) Targeting telomerase activity by BIBR1532 as a therapeutic approach in germ cell tumors, Invest New Drug 25, 519-524.

(34). Roth, A., Harley, C. B., and Baerlocher, G. M. (2010) Imetelstat (GRN163L)—Telomerase-Based Cancer Therapy, Recent Results Canc 184, 221-234.

(35). Kim, M.-Y., Vankayalapati, H., Shin-ya, K., Wierzba, K., and Hurley, L. H. (2002) Telomestatin, a Potent Telomerase Inhibitor That Interacts Quite Specifically with the Human Telomeric Intramolecular G-Quadruplex, J. Am. Chem. Soc. 124, 2098-2099.

(36). Burger, A. M., Dai, F., Schultes, C. M., Reszka, A. P., Moore, M. J., Double, J. A., and Neidle, S. (2005) The G-Quadruplex-Interactive Molecule BRACO-19 Inhibits Tumor Growth, Consistent with Telomere Targeting and Interference with Telomerase Function, Cancer Res. 65, 1489.

(37). De Cian, A., Cristofari, G., Reichenbach, P., De Lemos, E., Monchaud, D., Teulade-Fichou, M. P., Shin-Ya, K., Lacroix, L., Lingner, J., and Mergny, J. L. (2007) Reevaluation of telomerase inhibition by quadruplex ligands and their mechanisms of action, Proc. Natl. Acad. Sci. USA 104, 17347-17352.

(38). Neidle, S. (2010) Human telomeric G-quadruplex: The current status of telomeric G-quadruplexes as therapeutic targets in human cancer, FEBS Journal 277, 1118-1125.

(39). Li, Q., Xiang, J. F., Zhang, H., and Tang, Y. L. (2012) Searching Drug-Like Anti-cancer Compound(s) Based on G-Quadruplex Ligands, Curr. Pharm. Desig. 18, 1973-1983.

(40). Ganesan, K., and Xu, B. (2018) Telomerase Inhibitors from Natural Products and Their Anticancer Potential, Int. J. Mol. Sci. 19, 1-26.

(41). Naasani, I., Seimiya, H., and Tsuruo, T. (1998) Telomerase inhibition, telomere shortening, and senescence of cancer cells by tea catechins, Biochem. Biophys. Res. Commun. 249, 391-396.

(42). Seimiya, H., Oh-hara, T., Suzuki, T., Naasani, I., Shimazaki, T., Tsuchiya, K., and Tsuruo, T. (2002) Telomere shortening and growth inhibition of human cancer cells by novel synthetic telomerase inhibitors MST-312, MST-295, and MST-1991, Mol Cancer Ther 1, 657-665.

(43). Huang, P.-R., Yeh, Y.-M., and Wang, T.-C. V. (2005) Potent inhibition of human telomerase by helenalin, Cancer Lett. 227, 169-174.

(44). Choi, S.-H., Im, E., Kang, H. K., Lee, J.-H., Kwak, H.-S., Bae, Y.-T., Park, H.-J., and Kim, N. D. (2005) Inhibitory effects of costunolide on the telomerase activity in human breast carcinoma cells, Cancer Lett. 227, 153-162.

(45). Harvey, A. L. (2008) Natural products in drug discovery, Drug Discov. Today 13, 894-901.

(46). Harvey, A. L., Edrada-Ebel, R., and Quinn, R. J. (2015) The re-emergence of natural products for drug discovery in the genomics era, Nat. Rev. Drug Discov. 14, 111.

(47). Thomford, E. N., Senthebane, A. D., Rowe, A., Munro, D., Seele, P., Maroyi, A., and Dzobo, K. (2018) Natural Products for Drug Discovery in the 21st Century: Innovations for Novel Drug Discovery, Int. J. Mol. Sci. 19.

(48). Johnson, D. S., Weerapana, E., and Cravat, B. F. (2010) Strategies for discovering and derisking covalent, irreversible enzyme inhibitors, Future Med. Chem. 2, 949-964.

(49). Jackson, P. A., Widen, J. C., Harki, D. A., and Brummond, K. M. (2017) Covalent Modifiers: A Chemical Perspective on the Reactivity of α,β-Unsaturated Carbonyls with Thiols via Hetero-Michael Addition Reactions, J. Med. Chem. 60, 839-885.

(50). Singh, J., Petter, R. C., Baillie, T. A., and Whitty, A. (2011) The resurgence of covalent drugs, Nat. Rev. Drug Discov. 10, 307-317.

(51). Byrd, J. C., Furman, R. R., Coutre, S. E., Flinn, I. W., Burger, J. A., Blum, K. A., Grant, B., Sharman, J. P., Coleman, M., Wierda, W. G., Jones, J. A., Zhao, W., Heerema, N. A., Johnson, A. J., Sukbuntherng, J., Chang, B. Y., Clow, F., Hedrick, E., Buggy, J. J., James, D. F., and O'Brien, S. (2013) Targeting BTK with Ibrutinib in Relapsed Chronic Lymphocytic Leukemia, N. Eng. J. Med. 369, 32-42.

(52). Nakai, R., Kakita, S., Asai, A., Cniba, S., Akinaga, S., Mizukami, T., and Yamashita, Y. (2001) Chrolactomycin, a Novel Antitumor Antibiotic Produced by *Streptomyces* sp., J. Antibiot (Tokyo) 54, 836-839.

(53). Nakai, R., Ishida, H., Asai, A., Ogawa, H., Yamamoto, Y., Kawasaki, H., Akinaga, S., Mizukami, T., and Yamashita, Y. (2006) Telomerase inhibitors identified by a forward chemical genetics approach using a yeast strain with shortened telomere length, Chem. Biol. 13, 183-190.

(54). Iorio, M., Maffioli, S. I., Gaspari, E., Rossi, R., Mauri, P., Sosio, M., and Donadio, S. (2012) Chrolactomycins from the actinomycete actinospica, J. Nat. Prod. 75, 1991-1993.

(55). Tenenbaum, J. M., Morris, W. J., Custar, D. W., and Scheidt, K. A. (2011) Synthesis of (−)-Okilactomycin by a Prins-Type Fragment-Assembly Strategy, Angew. Chem. Int. Ed. 50, 5892-5895.

(56). Smith, A. B., Basu, K., and Bosanac, T. (2007) Total Synthesis of (−)-Okilactomycin, J. Am. Chem. Soc. 129, 14872-14874.

(57). Custar, D. W., Zabawa, T. P., and Scheidt, K. A. (2008) Total Synthesis and Structural Revision of the Marine Macrolide Neopeltolide, J. Am. Chem. Soc. 130, 804-805.

(58). Custar, D. W., Zabawa, T. P., Hines, J., Crews, C. M., and Scheidt, K. A. (2009) Total Synthesis and Structure-Activity Investigation of the Marine Natural Product Neopeltolide, J. Am. Chem. Soc. 131, 12406-12414.

(59). Crane, E. A., and Scheidt, K. A. (2010) Prins-Type Macrocyclizations as an Efficient Ring-Closing Strategy in Natural Product Synthesis, Angew Chem Int Edit 49, 8316-8326.

(60). Crane, E. A., Zabawa, T. P., Farmer, R. L., and Scheidt, K. A. (2011) Enantioselective Synthesis of (−)-Exiguolide by Iterative Stereoselective Dioxinone-Directed Prins Cyclizations, Angew. Chem. Int. Ed. 50, 9112-9115.

(61). Gillis, A. J., Schuller, A. P., and Skordalakes, E. (2008) Structure of the *Tribolium castaneum* telomerase catalytic subunit TERT, Nature 455, 633-636.

(62). Mitchell, M., Gillis, A., Futahashi, M., Fujiwara, H., and Skordalakes, E. (2010) Structural basis for telomerase catalytic subunit TERT binding to RNA template and telomeric DNA, Nat. Struct. Mol. Biol. 17, 513.

(63). Nguyen, T. H. D., Tam, J., Wu, R. A., Greber, B. J., Toso, D., Nogales, E., and Collins, K. (2018) Cryo-EM structure of substrate-bound human telomerase holoenzyme, Nature 557, 190-195.

(64). Hassan, M., Brown, R. D., Varma-O'Brien, S., and Rogers, D. (2006) Cheminformatics analysis and learning in a data pipelining environment, Mol. Div. 10, 283-299.

(65). Hu, Y., Lounkine, E., and Bajorath, J. (2009) Improving the Search Performance of Extended Connectivity Fingerprints through Activity-Oriented Feature Filtering and Application of a Bit-Density-Dependent Similarity Function, ChemMedChem 4, 540-548.

(66). Warr, W. A. (2012) Scientific workflow systems: Pipeline Pilot and KNIME, J. Comput. Aided Mol. Des. 26, 801-804.

(67). Ghose, A. K., Viswanadhan, V. N., and Wendoloski, J. J. (1999) A knowledge-based approach in designing combinatorial or medicinal chemistry libraries for drug discovery. 1. A qualitative and quantitative characterization of known drug databases, J. Comb. Chem. 1, 55-68.

(68). Friesner, R. A., Banks, J. L., Murphy, R. B., Halgren, T. A., Klicic, J. J., Mainz, D. T., Repasky, M. P., Knoll, E. H., Shelley, M., Perry, J. K., Shaw, D. E., Francis, P., and Shenkin, P. S. (2004) Glide: A New Approach for Rapid, Accurate Docking and Scoring. 1. Method and Assessment of Docking Accuracy, J. Med. Chem. 47, 1739-1749.

(69). Halgren, T. A., Murphy, R. B., Friesner, R. A., Beard, H. S., Frye, L. L., Pollard, W. T., and Banks, J. L. (2004) Glide: A New Approach for Rapid, Accurate Docking and Scoring. 2. Enrichment Factors in Database Screening, J. Med. Chem. 47, 1750-1759.

(70). Friesner, R. A., Murphy, R. B., Repasky, M. P., Frye, L. L., Greenwood, J. R., Halgren, T. A., Sanschagrin, P. C., and Mainz, D. T. (2006) Extra Precision Glide: Docking and Scoring Incorporating a Model of Hydrophobic Enclosure for Protein—Ligand Complexes, J. Med. Chem. 49, 6177-6196.

(71). Toledo Warshaviak, D., Golan, G., Borrelli, K. W., Zhu, K., and Kalid, O. (2014) Structure-Based Virtual Screening Approach for Discovery of Covalently Bound Ligands, J. Chem. Inf. Mod. 54, 1941-1950.

(72). Zhu, K., Borrelli, K. W., Greenwood, J. R., Day, T., Abel, R., Farid, R. S., and Harder, E. (2014) Docking Covalent Inhibitors: A Parameter Free Approach To Pose Prediction and Scoring, J. Chem. Inf. Mod. 54, 1932-1940.

(73). Morris, W. J., Custar, D. W., and Scheidt, K. A. (2005) Stereoselective Synthesis of Tetrahydropyran-4-ones from Dioxinones Catalyzed by Scandium(III) Triflate, Org. Lett. 7, 1113-1116.

(74). Singer, R. A., and Carreira, E. M. (1995) Catalytic, Enantioselective Dienolate Additions to Aldehydes: Preparation of Optically Active Acetoacetate Aldol Adducts, J. Am. Chem. Soc. 117, 12360-12361.

(75). Krüger, J., and Carreira, E. M. (1998) Apparent Catalytic Generation of Chiral Metal Enolates: Enantioselective Dienolate Additions to Aldehydes Mediated by Tol-BINAP-Cu(II) Fluoride Complexes, J. Am. Chem. Soc. 120, 837-838.

(76). Denmark, S. E., and Beutner, G. L. (2003) Lewis Base Activation of Lewis Acids. Vinylogous Aldol Reactions, J. Am. Chem. Soc. 125, 7800-7801.

(77). De Rosa, M., Acocella, M. R., Villano, R., Soriente, A., and Scettri, A. (2003) A convenient catalytic procedure for the highly enantioselective aldol condensation of O-silyldienolates, Tetrahedron: Asymmetry 14, 2499-2502.

(78). Gondi, V. B., Gravel, M., and Rawal, V. H. (2005) Hydrogen Bond Catalyzed Enantioselective Vinylogous Mukaiyama Aldol Reaction, Org. Lett. 7, 5657-5660.

(79). Denmark, S. E., Heemstra, J. R., and Beutner, G. L. (2005) Catalytic, Enantioselective, Vinylogous Aldol Reactions, Angew. Chem. Int. Ed. 44, 4682-4698.

(80). Betori, R. C., Miller, E. R., and Scheidt, K. A. (2017) A Biocatalytic Route to Highly Enantioenriched β-Hydroxydioxinones, Adv. Synth. Catal. 359, 1131-1137.

(81). Kathman, S. G., Xu, Z., and Statsyuk, A. V. (2014) A Fragment-Based Method to Discover Irreversible Covalent Inhibitors of Cysteine Proteases, J. Med. Chem. 57, 4969-4974.

(82). Flanagan, M. E., Abramite, J. A., Anderson, D. P., Aulabaugh, A., Dahal, U. P., Gilbert, A. M., Li, C., Montgomery, J., Oppenheimer, S. R., Ryder, T., Schuff, B. P., Uccello, D. P., Walker, G. S., Wu, Y., Brown, M. F., Chen, J. M., Hayward, M. M., Noe, M. C., Obach, R. S., Philippe, L., Shanmugasundaram, V., Shapiro, M. J., Starr, J., Stroh, J., and Che, Y. (2014) Chemical and Computational Methods for the Characterization of Covalent Reactive Groups for the Prospective Design of Irreversible Inhibitors, J. Med. Chem. 57, 10072-10079.

(83). Cee, V. J., Volak, L. P., Chen, Y., Bartberger, M. D., Tegley, C., Arvedson, T., McCarter, J., Tasker, A. S., and Fotsch, C. (2015) Systematic Study of the Glutathione (GSH) Reactivity of N-Arylacrylamides: 1. Effects of Aryl Substitution, J. Med. Chem. 58, 9171-9178.

(84). Palkowitz, M. D., Tan, B., Hu, H., Roth, K., and Bauer, R. A. (2017) Synthesis of Diverse N-Acryloyl Azetidines and Evaluation of Their Enhanced Thiol Reactivities, Org. Lett. 19, 2270-2273.

(85). Ward, R. A., Anderton, M. J., Ashton, S., Bethel, P. A., Box, M., Butterworth, S., Colclough, N., Chorley, C. G., Chuaqui, C., Cross, D. A. E., Dakin, L. A., Debreczeni, J. E., Eberlein, C., Finlay, M. R. V., Hill, G. B., Grist, M., Klinowska, T. C. M., Lane, C., Martin, S., Orme, J. P., Smith, P., Wang, F., and Waring, M. J. (2013) Structure- and Reactivity-Based Development of Covalent Inhibitors of the Activating and Gatekeeper Mutant Forms of the Epidermal Growth Factor Receptor (EGFR), J. Med. Chem. 56, 7025-7048.

(86). Wilson, A. J., Kerns, J. K., Callahan, J. F., and Moody, C. J. (2013) Keap Calm, and Carry on Covalently, J. Med. Chem. 56, 7463-7476.

(87). Ding, Y., Li, D., Ding, C., Wang, P., Liu, Z., Wold, E. A., Ye, N., Chen, H., White, M. A., Shen, Q., and Zhou, J. (2018) Regio- and Stereospecific Synthesis of Oridonin D-Ring Aziridinated Analogues for the Treatment of Triple-Negative Breast Cancer via Mediated Irreversible Covalent Warheads, J. Med. Chem. 61, 2737-2752.

(88). Cohen, S. B., and Reddel, R. R. (2008) A sensitive direct human telomerase activity assay, Nat. Met. 5, 355.

(89). Tomlinson, C. G., Sasaki, N., Jurczyluk, J., Bryan, T. M., and Cohen, S. B. (2017) Quantitative assays for measuring human telomerase activity and DNA binding properties, Methods 114, 85-95.

(90). Wright, W. E., Shay, J. W., and Piatyszek, M. A. (1995) Modifications of a telomeric repeat amplification protocol (TRAP) result in increased reliability, linearity and sensitivity, Nucleic Acids Res. 23, 3794-3795.

(91). Wu, Y.-Y., Hruszkewycz, A. M., Delgado, R. M., Yang, A., Vortmeyer, A. O., Moon, Y.-W., Weil, R. J., Zhuang, Z., and Remaley, A. T. (2000) Limitations on the quantitative determination of telomerase activity by the electrophoretic and ELISA based TRAP assays, Clin. Chim. Acta 293, 199-212.

(92). Bryan, T. M., Englezou, A., Gupta, J., Bacchetti, S., and Reddel, R. R. (1995) Telomere elongation in immortal human cells without detectable telomerase activity, EMBO J. 14, 4240-4248.

(93). Li, S., Rosenberg, J. E., Donjacour, A. A., Botchkina, I. L., Hom, Y. K., Cunha, G. R., and Blackburn, E. H. (2004) Rapid Inhibition of Cancer Cell Growth Induced by Lentiviral Delivery and Expression of Mutant-Template Telomerase RNA and Anti-telomerase Short-Interfering RNA, Cancer Res. 64, 4833.

(94). Zhao, P., Wang, C., Fu, Z., You, Y., Cheng, Y., Lu, X., Lu, A., Liu, N., Pu, P., Kang, C., Salford, L. G., and Fan, X. (2007) Lentiviral vector mediated siRNA knock-down of hTERT results in diminished capacity in invasiveness and in vivo growth of human glioma cells in a telomere length-independent manner, Int. J. Oncol. 31, 361-368.

(95). Shen, Y., Zhang, Y.-W., Zhang, Z.-X., Miao, Z.-H., and Ding, J. (2008) hTERT-targeted RNA interference inhibits tumorigenicity and motility of HCT116 cells, Canc. Biol. Ther. 7, 228-236.

(96). Mender, I., Gryaznov, S., Dikmen, Z. G., Wright, W. E., and Shay, J. W. (2015) Induction of Telomere Dysfunction Mediated by the Telomerase Substrate Precursor 6-Thio-2'-Deoxyguanosine, Cancer Disc. 5, 82.

(97). Leung, D., Hardouin, C., Boger, D. L., and Cravatt, B. F. (2003) Discovering potent and selective reversible inhibitors of enzymes in complex proteomes, Nat. Biotechnol. 21, 687-691.

(98). Chiang, K. P., Niessen, S., Saghatelian, A., and Cravatt, B. F. (2006) An Enzyme that Regulates Ether Lipid Signaling Pathways in Cancer Annotated by Multidimensional Profiling, Chem. Biol. 13, 1041-1050.

(99). Ahn, K., Johnson, D. S., Fitzgerald, L. R., Liimatta, M., Arendse, A., Stevenson, T., Lund, E. T., Nugent, R. A., Nomanbhoy, T. K., Alexander, J. P., and Cravatt, B. F. (2007) Novel Mechanistic Class of Fatty Acid Amide Hydrolase Inhibitors with Remarkable Selectivity, Biochemistry 46, 13019-13030.

(100). Long, J. Z., Li, W., Booker, L., Burston, J. J., Kinsey, S. G., Schlosburg, J. E., Pavan, F. J., Serrano, A. M., Selley, D. E., Parsons, L. H., Lichtman, A. H., and Cravatt, B. F. (2009) Selective blockade of 2-arachidonoylglycerol hydrolysis produces cannabinoid behavioral effects, Nat. Chem. Biol. 5, 37-44.

(101). Long, J. Z., Nomura, D. K., Vann, R. E., Walentiny, D. M., Booker, L., Jin, X., Burston, J. J., Sim-Selley, L. J., Lichtman, A. H., Wiley, J. L., and Cravatt, B. F. (2009) Dual blockade of FAAH and MAGL identifies behavioral processes regulated by endocannabinoid crosstalk in vivo, Proc. Natl. Acad. Sci. U.S.A. 106, 20270.

(102). Bachovchin, D. A., Ji, T., Li, W., Simon, G. M., Blankman, J. L., Adibekian, A., Hoover, H., Niessen, S., and Cravatt, B. F. (2010) Superfamily-wide portrait of serine hydrolase inhibition achieved by library-versus-library screening, Proc. Natl. Acad. Sci. U.S.A. 107, 20941.

(103). Nomura, D. K., and Casida, J. E. (2011) Activity-Based Protein Profiling of Organophosphorus and Thiocarbamate Pesticides Reveals Multiple Serine Hydrolase Targets in Mouse Brain, J. Agric. Food. Chem. 59, 2808-2815.

(104). Zuhl, A. M., Mohr, J. T., Bachovchin, D. A., Niessen, S., Hsu, K.-L., Berlin, J. M., Dochnahl, M., Lopez-Alberca, M. P., Fu, G. C., and Cravatt, B. F. (2012) Competitive Activity-Based Protein Profiling Identifies Aza-β-Lactams as a Versatile Chemotype for Serine Hydrolase Inhibition, J. Am. Chem. Soc. 134, 5068-5071.

(105). Kaschani, F., Nickel, S., Pandey, B., Cravatt, B. F., Kaiser, M., and van der Hoorn, R. A. L. (2012) Selective inhibition of plant serine hydrolases by agrochemicals revealed by competitive ABPP, Biorg. Med. Chem. 20, 597-600.

(106). Camara, K., Kamat, S. S., Lasota, C. C., Cravatt, B. F., and Howell, A. R. (2015) Combining cross-metathesis and activity-based protein profiling: New β-lactone motifs for targeting serine hydrolases, Biorg. Med. Chem. Lett. 25, 317-321.

(107). Gilad, Y., Nadassy, K., and Senderowitz, H. (2015) A reliable computational workflow for the selection of optimal screening libraries, J Cheminform 7, 61.

(108). Baell, J. B., and Holloway, G. A. (2010) New Substructure Filters for Removal of Pan Assay Interference Compounds (PAINS) from Screening Libraries and for Their Exclusion in Bioassays, J. Med. Chem. 53, 2719-2740.

(109). Zhu, K., Borrelli, K. W., Greenwood, J. R., Day, T., Abel, R., Farid, R. S., and Harder, E. (2014) Docking covalent inhibitors: a parameter free approach to pose prediction and scoring, J Chem Inf Model 54, 1932-1940.

(110). Kuhn, B., Kollman, P. A., and Stahl, M. (2004) Prediction of pKa shifts in proteins using a combination of molecular mechanical and continuum solvent calculations, J. Comput. Chem. 25, 1865-1872.

(111). Harder, E., Damm, W., Maple, J., Wu, C., Reboul, M., Xiang, J. Y., Wang, L., Lupyan, D., Dahlgren, M. K., Knight, J. L., Kaus, J. W., Cerutti, D. S., Krilov, G., Jorgensen, W. L., Abel, R., and Friesner, R. A. (2016) OPLS3: A Force Field Providing Broad Coverage of Drug-like Small Molecules and Proteins, J. Chem. Theory Comput. 12, 281-296.

(112). Halgren, T. (2007) New method for fast and accurate binding-site identification and analysis, Chem Biol Drug Des 69, 146-148.

Example 2—Supporting Information for Targeting Covalent Inhibition of Telomeres

General Information for Chemistry

All reactions were carried out under an argon or nitrogen atmosphere in flame-dried glassware with magnetic stirring. Solvents used in reactions were purified by passage through a bed of activated alumina. Unless stated otherwise, reagents were purified prior to use following the guidelines of Perrin and Armarego.[1] Purification of reaction products was carried out by flash chromatography on Biotage Isolera 4 systems with Ultra-grade silica cartridges. Analytical thin layer chromatography was performed on EM Reagent 0.25 mm silica gel 60-F plates. Visualization was accomplished with UV light. Infrared spectra were recorded on a Bruker Tensor 37 FT-IR spectrometer. 1H NMR spectra were recorded on an AVANCE III 500 MHz spectrometer with direct cryoprobe (500 MHz) and Bruker Avance III 600 MHz (151 MHz) system. Spectra are reported in ppm using solvent as an internal standard (CHCl3 at 7.26 ppm). Peak multiplicities are reported as (s=singlet, d=doublet, t=triplet, q=quartet, quint=quintet, m=multiplet, br=broad; coupling constant(s) in Hz; integration.) Proton-decoupled 13C NMR spectra were recorded on an AVANCE III 500 MHz with direct cryoprobe (125 MHz) spectrometer or Bruker Avance III 600 MHz (151 MHz) system. These are reported in ppm using solvent as an internal standard (CDCl3 at 77.16 ppm). Low-resolution mass spectra were obtained on WATERS Acquity-H UPLC-MS with a single quad detector (ESI) Varian1200 Quadrupole Mass Spectrometer. High-resolution mass spectra were obtained using an Agilent 6120A LC-time of flight mass spectrometer. Gas chromatography experiments were run on Agilent 7890A/5975C GC/MS System.

General Procedure for Synthesis of Racemic Analogues

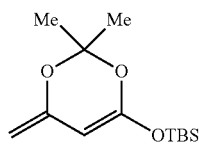
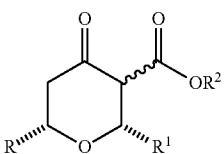

tert-butyl ((2,2-dimethyl-4-methylene-4H-1,3-dioxin-6-yl)oxy)dimethylsilane (1.0 equiv) and the desired aldehyde (1.2 equiv) were added to a 20 mL oven dried scintillation vial equipped with a magnetic stir bar. 4 Å MS (200 wt % relative to tert-butyl((2,2-dimethyl-4-methylene4H-1,3-dioxin-6-yl)oxy)dimethylsilane) was added, and the vial was sealed and placed under inert atmosphere, followed by addition of CH$_2$Cl2 (0.2 M). The reaction vial was cooled to 78° C. BF3.OEt$_2$ (1.2 equiv) was added dropwise over a period of 15 minutes. The reaction was monitored by UPLC-MS until complete consumption of tert-butyl((2,2-dimethyl-4methylene-4H-1,3-dioxin-6-yl)oxy)dimethylsilane was observed (typically 2-4 hours). When consumption was complete, the reaction was warmed to 0° C. Subsequently, the second aldehyde (1.2 equiv) was added by syringe, followed by BF$_3$.OEt$_2$ (2.0 equiv). The reaction was stirred at 0° C., and the reaction progress was monitored by UPLC-MS until complete consumption of the β-hydroxydioxinone was observed. Upon complete consumption, 0.1 M potassium phosphate buffer (pH 7.0) was added by syringe and the reaction was warmed to room temperature. The reaction mixture was diluted with CH2Cl2 and the suspension was then filtered through a Biotage Isolute phase separator and then concentrated. Typically, reactions were of sufficient purity for the subsequent reaction.

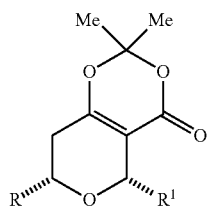

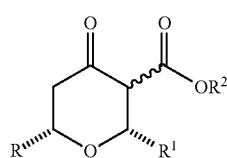

To a microwave vial equipped with a stir bar was added bicyclic dioxinone pyran (1.0 equiv), which was dissolved in toluene (0.2 M). The corresponding alcohol (10 equiv) was added, the microwave vial was capped, and the reaction was heated in a Biotage microwave reactor at 150° C. for 90 min. After the vial was cooled to room temperature, the solution was concentrated, and the crude product was of sufficient purity for the subsequent reaction.

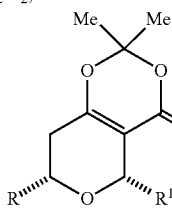
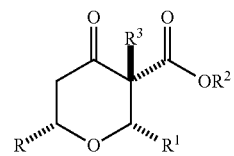

In a microwave vial equipped with a magnetic stir bar was added β-keto ester (1.0 equiv), which was dissolved in acetonitrile (0.2 M). To the solution was added potassium carbonate (4 equiv) and alkyl halide (10 equiv). The reaction mixture was heated to 70° C., and conversion of the starting material was monitored by UPLC-MS (typically 2-4 hours) before cooling to room temperature. The reaction mixture was diluted with CH$_2$Cl2, filtered through a Biotage Isolute phase separator and concentrated to afford the crude product, which was of sufficient purity for the subsequent reaction. When benzyl bromide was used, the concentrated vial was dried under high vacuum at 40° C. overnight to remove residual benzyl bromide.

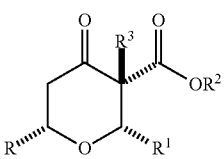
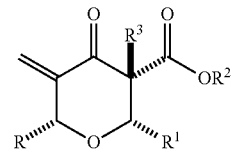

To a microwave vial equipped with a magnetic stir bar was added the alkylated β-keto ester (1.0 equiv), which was dissolved in CH2Cl2 (0.5 M). To the solution was added CH2Br2 (6 equiv) and Et2NH (12 equiv). The container was sealed and the reaction heated in a Biotage microwave reactor at 100° C. for 1 hour. After the vial was cooled to room temperature, the reaction solution was concentrated. Diethyl ether was added to the crude reaction mixture to precipitate out the ammonium salts. The mixture was filtered, and the filtrate was concentrated. The crude product was purified by flash chromatography to yield the desired product.

Characterization of Racemic Telomerase Inhibitors

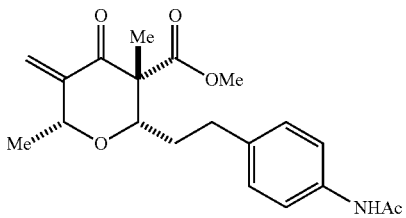

(±) methyl (2S,3R,6R)-2-(4-acetamidophenethyl)-3,6-dimethyl-5-methylene-4-oxotetrahydro2H-pyran-3-carboxylate 1H NMR (500 MHz, Chloroform-d) δ 7.38-7.30 (m, 2H), 7.13 (d, J=7.6 Hz, 1H), 7.00 (d, J=8.0 Hz, 1H), 6.14 (d, J=2.2 Hz, 1H), 5.38 (d, J=2.2 Hz, 1H), 4.50-4.41 (m, 1H), 4.09-4.02 (m, 1H), 3.62 (s, 3H), 2.63 (dt, J=14.8, 8.4 Hz, 2H), 2.15 (s, 3H), 1.92-1.78 (m, 2H), 1.46 (d, J=6.3 Hz, 3H), 1.31 (s, 3H). 13C NMR (126 MHz, CDCl3) δ 197.5, 171.2, 168.2, 142.5, 137.9, 129.0, 124.4, 122.7, 119.9, 117.4, 77.9, 74.7, 60.9, 52.4, 32.2, 29.7, 24.8, 20.2, 14.6. LCMS (ESI): Mass calculated for C20H26NO5 [M+H]+: 360.1733, Found 360.1745

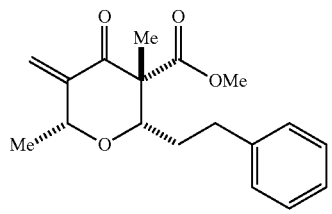 [SMILES: C=C1C(=O)[C@](C)(C(=O)OC)[C@H](CCc2ccccc2)O[C@@H]1C]

(±) methyl (2S,3R,6R)-3,6-dimethyl-5-methylene-4-oxo-2-phenethyltetrahydro-2H-pyran-3 carboxylate 1H NMR (500 MHz, Chloroform-d) δ 7.30-7.13 (m, 5H), 6.14 (d, J=2.1 Hz, 1H), 5.37 (d, J=2.1 Hz, 1H), 3.73-3.61 (m, 2H), 3.61 (s, 3H), 2.94-2.79 (m, 2H), 2.73-2.54 (m, 2H), 1.54 (s, 3H), 1.44 (d, J=2.1 Hz 3H). 13C NMR (126 MHz, CDCl3) δ 197.4, 171.1, 144.3, 141.4, 128.5, 128.4, 128.4, 126.0, 122.6, 77.9, 74.7, 60.9, 52.3, 32.2, 32.2, 20.2, 14.5. LCMS (ESI): Mass calculated for C18H23O4 [M+H]+: 303.1518, Found 303.1522

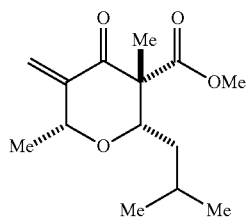 [SMILES: C=C1C(=O)[C@](C)(C(=O)OC)[C@H](CC(C)C)O[C@@H]1C]

(±) methyl (2S,3R,6R)-2-isobutyl-3,6-dimethyl-5-methylene-4-oxotetrahydro-2H-pyran-3 carboxylate 1H NMR (500 MHz, Chloroform-d) δ 6.15 (d, J=2.3, 0.8 Hz, 1H), 5.37 (d, J=2.2, 0.8 Hz, 1H), 4.52-4.44 (m, 1H), 4.19-4.13 (m, 1H), 3.70 (s, 3H), 1.89-1.50 (m, 3H), 1.43 (d, J=6.3 Hz, 3H), 1.30 (s, 3H), 0.98-0.82 (m, 6H). 13C NMR (126 MHz, CDCl3) δ 197.7, 171.3, 144.4, 122.5, 77.2, 74.6, 61.1, 52.3, 39.6, 25.0, 23.4, 21.7, 20.3, 14.4. LCMS (ESI): Mass calculated for C14H23O4 [M+H]+: 255.1518, Found 255.1522

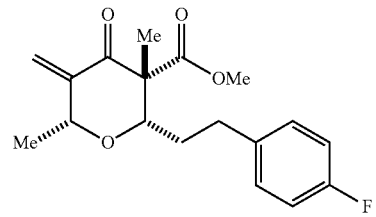 [SMILES: C=C1C(=O)[C@](C)(C(=O)OC)[C@H](CCc2ccc(F)cc2)O[C@@H]1C]

(±) methyl (2S,3R,6R)-2-(4-fluorophenethyl)-3,6-dimethyl-5-methylene-4-oxotetrahydro-2H pyran-3-carboxylate 1H NMR (500 MHz, Chloroform-d) δ 7.34-7.20 (m, 3H), 6.93 (d, J=3.8 Hz, 1H), 6.15 (d, J=2.2 Hz, 1H), 5.38 (d, J=2.2 Hz, 1H), 4.48-4.39 (m, 1H), 4.04-3.94 (m, 1H), 3.63 (s, 3H), 2.87 (dq, J=13.0, 7.3, 5.4 Hz, 2H), 1.94-1.83 (m, 2H), 1.46 (d, J=6.2 Hz, 3H), 1.32 (s, 3H). 13C NMR (126 MHz, CDCl3) δ 201.1, 162.9 (d, J=248 Hz), 144.1, 130.0 (d, J=3.2 Hz), 124.8, 124.6 (d, J=8.2 Hz) 122.8, 115.2 (d, J=21.5 Hz), 77.7, 74.7, 67.1, 52.4, 32.0, 31.9, 20.2, 14.5. LCMS (ESI): Mass calculated for C18H22FO4 [M+H]+: 321.1424, Found 321.1430

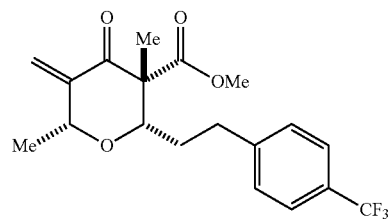

(±) methyl (2S,3R,6R)-3,6-dimethyl-5-methylene-4-oxo-2-(4(trifluoromethyl)phenethyl)tetrahydro-2H-pyran-3-carboxylate 1H NMR (500 MHz, Chloroform-d) δ 7.51 (dd, J=13.9, 5.6 Hz, 2H), 7.33-7.20 (m, 2H), 6.15 (d, J=2.2 Hz, 1H), 5.38 (d, J=2.2 Hz, 1H), 4.91-4.65 (m, 1H), 4.55-4.39 (m, 1H), 3.62 (s, 3H), 2.99-2.66 (m, 2H), 2.11-1.79 (m, 2H), 1.45 (d, J=6.2 Hz, 3H), 1.32 (s, 3H). 13C NMR (126 MHz, CDCl3) δ 197.2, 171.1, 145.5, 144.0, 128.8 (q, J=32.6 Hz), 127.7, 125.4 (q, J=3.7 Hz), 123.2 (q, J=3.7 Hz), 100.3, 77.8, 74.8, 60.8, 52.5, 32.1, 29.4, 20.2, 14.5. LCMS (ESI): Mass calculated for C19H22F3O4 [M+H]+: 371.1392, Found 371.1401

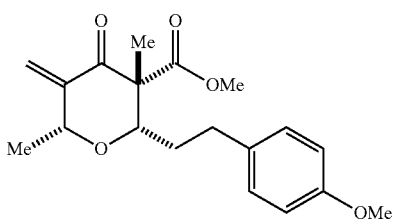

(±) methyl (2S,3R,6R)-2-(4-methoxyphenethyl)-3,6-dimethyl-5-methylene-4-oxotetrahydro2H-pyran-3-carboxylate 1H NMR (500 MHz, Chloroform-d) δ 7.26-7.19 (m, 2H), 6.97-6.94 (m, 2H), 6.30 (d, J=2.2 Hz, 1H), 5.53 (d, J=2.2 Hz, 1H), 4.64-4.55 (m, 1H), 4.19-4.10 (m, 1H), 3.92 (s, 3H), 3.78 (s, 3H), 2.74-2.68 (m, 2H), 2.07-2.01 (m, 2H), 1.62 (d, J=6.3 Hz, 3H), 1.47 (s, 3H). 13C NMR (126 MHz, CDCl3) δ 197.4, 171.2, 157.8, 144.3, 133.7, 129.3, 129.3, 122.6, 113.8, 77.9, 74.7, 55.3, 52.7, 34.3, 30.0, 20.2, 14.6. LCMS (ESI): Mass calculated for C19H25O5 [M+H]+: 333.1624, Found 333.1609

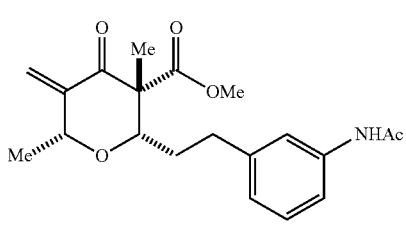

(±) methyl (2S,3R,6R)-2-(3-acetamidophenethyl)-3,6-dimethyl-5-methylene-4-oxotetrahydro2H-pyran-3-carboxylate 1H NMR (500 MHz, Chloroform-d) δ 7.39 (d, J=2.9 Hz, 2H), 7.19-7.15 (m, 1H), 7.11 (d, J=2.4 Hz, 1H), 6.14 (d, J=2.1 Hz, 1H), 5.37 (d, J=2.2 Hz, 1H), 4.43-4.38 (m 1H), 4.02 (m, 1H), 3.62 (s, 3H), 2.61-2.55 (m, 2H), 2.14 (s, 3H), 1.92-1.77 (m, 2H), 1.45 (d, J=6.3 Hz, 3H), 1.31 (s, 3H). 13C NMR (126 MHz, CDCl3) δ 197.4, 171.1, 168.2, 144.2, 137.4, 135.9, 135.2, 129.7, 128.9, 122.7, 120.0, 77.8, 74.7, 60.9, 52.4, 32.1, 31.5, 24.6, 20.3, 14.5. LCMS (ESI): Mass calculated for C20H26NO5 [M+H]+: 360.1733, Found 360.1745

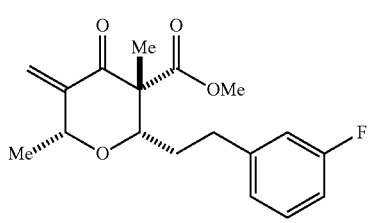

(±) methyl (2S,3R,6R)-2-(3-fluorophenethyl)-3,6-dimethyl-5-methylene-4-oxotetrahydro-2H pyran-3-carboxylate 1H NMR (500 MHz, Chloroform-d) δ 7.17-7.03 (m, 2H), 6.95-6.86 (m, 2H), 6.15 (d, J=2.3 Hz, 1H), 5.38 (d, J=2.3 Hz, 1H), 4.32 (t, J=5.7 Hz, 1H), 4.02-3.92 (m, 1H), 3.63 (s, 3H), 2.81-2.63 (m, 2H), 2.05-1.91 (m, 2H), 1.46 (d, J=6.3 Hz, 3H), 1.31 (s, 3H). 13C NMR (126 MHz, CDCl3) δ 197.2, 171.1, 160.4, 144.2, 137.0, 129.7 (d, J=3.2 Hz), 122.7, 115.2 (d, J=21.5 Hz), 103.6, 100.5, 77.8, 74.7, 60.9, 52.8, 35.8, 32.3, 20.2, 14.5. LCMS (ESI): Mass calculated for C18H22FO4 [M+H]+: 321.1424, Found 321.1432

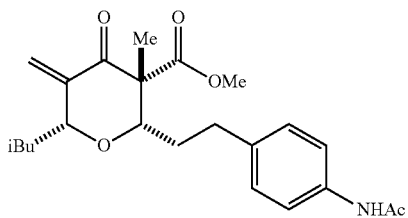

(±) methyl (2S,3R,6R)-2-(4-acetamidophenethyl)-6-isobutyl-3-methyl-5-methylene-4oxotetrahydro-2H-pyran-3-carboxylate 1H NMR (500 MHz, Chloroform-d) δ 7.24 (d, J=3.4 Hz, 2H), 6.91 (d, J=8.3 Hz, 2H), 6.14 (d, J=2.1 Hz, 1H), 5.37 (d, J=2.1 Hz, 1H), 3.77-3.71 (m, 1H), 3.56-3.51 (m, 1H), 3.49 (s, 3H), 2.26-2.06 (m, 2H), 1.97 (s, 3H), 1.79-1.65 (m, 2H), 1.55-1.44 (m, 2H), 1.17 (s, 3H), 1.07-0.99 (m, 1H), 0.82-0.69 (m, 6H). 13C NMR (126 MHz, CDCl3) δ 206.6, 171.4, 168.3, 144.2, 137.3, 136.0, 128.9, 120.0, 79.3, 75.3, 62.4, 52.2, 45.4, 32.3, 31.7, 24.5, 24.4, 23.3, 22.0, 14.3. LCMS (ESI): Mass calculated for C23H32NO5 [M+H]+: 402.2202, Found 402.2210

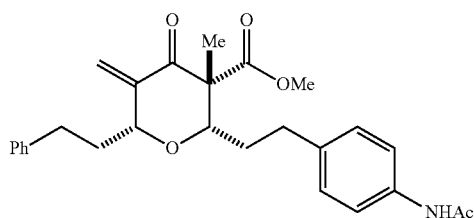

(±) methyl (2S,3R,6R)-2-(4-acetamidophenethyl)-3-methyl-5-methylene-4-oxo-6phenethyltetrahydro-2H-pyran-3-carboxylate 1H NMR (500 MHz, Chloroform-d) δ 7.54-7.48 (m, 2H), 7.37-7.28 (m, 2H), 7.26-7.19 (m, 3H), 7.14-7.09 (m, 2H), 6.14 (d, J=2.1 Hz, 1H), 5.37 (d, J=2.1 Hz, 1H), 3.75-3.67 (m, 1H), 3.67 (s, 3H), 3.22-3.18 (m, 1H), 2.98-2.90 (m, 1H), 2.83-2.73 (m, 1H), 2.73-2.62 (m, 1H), 2.61-2.57 (m, 2H), 2.50-2.27 (m, 2H), 2.16 (s, 3H), 2.09-1.90 (m, 2H), 1.36 (s, 3H). 13C NMR (126 MHz, CDCl3) δ 206.3, 171.3, 168.9, 162.6, 141.2, 136.7, 128.7, 128.5, 128.4, 126.0, 120.0, 79.2, 75.9, 62.3, 52.1, 46.8, 43.6, 37.8, 36.5, 31.4, 24.2, 14.2, 8.7. LCMS (ESI): Mass calculated for C27H32NO5 [M+H]+: 449.2202, Found 449.2198

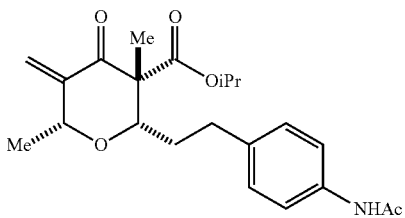

(±) isopropyl (2S,3R,6R)-2-(4-acetamidophenethyl)-3,6-dimethyl-5-methylene-4oxotetrahydro-2H-pyran-3-carboxylate 1H NMR (500 MHz, Chloroform-d) δ 7.41-7.35 (m, 2H), 7.08-7.00 (m, 2H), 6.12 (d, J=2.1 Hz, 1H), 5.36 (d, J=2.0 Hz, 1H), 4.99 (d, J=6.4 Hz, 1H), 4.43-4.33 (m, 1H), 4.04-3.98 (m, 1H), 2.89-2.55 (m, 2H), 2.15 (s, 3H), 2.06-1.84 (m, 2H), 1.46 (d, J=6.2 Hz, 3H), 1.28 (s, 3H), 1.26-1.09 (m, 6H). 13C NMR (126 MHz, CDCl3) δ 197.6, 170.1, 168.1, 144.4, 137.4, 135.9, 129.0, 122.4, 120.0, 77.6, 77.2, 74.7, 68.8, 60.7, 31.5, 29.7, 24.7, 21.4, 20.2, 14.5. LCMS (ESI): Mass calculated for C22H30NO5 [M+H]+: 388.2046, Found 388.2044

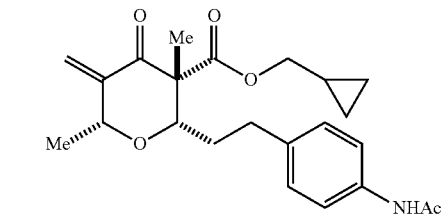

(±) cyclopropylmethyl (2S,3R,6R)-2-(4-acetamidophenethyl)-3,6-dimethyl-5-methylene-4oxotetrahydro-2H-pyran-3-carboxylate 1H NMR (500 MHz, Chloroform-d) δ 7.42-7.24 (m, 2H), 7.10-6.99 (m, 2H), 6.14 (d, J=2.1 Hz, 1H), 5.37 (d, J=2.1 Hz, 1H), 4.45-4.28 (m, 1H), 4.13-4.04 (m, 1H), 4.02-3.79 (m, 2H), 2.94-2.80 (m, 2H), 2.63-2.55 (m, 2H), 2.14 (s, 3H), 1.46 (d, J=6.2 Hz, 3H), 1.31 (s, 3H), 1.06-0.95 (m, 1H), 0.56-0.43 (m, 2H), 0.29-0.15 (m, 2H). 13C NMR (126 MHz, CDCl3) δ 197.5, 170.8, 168.2, 144.3, 137.4, 129.0, 126.6, 122.6, 120.0, 77.9, 74.7, 69.9, 60.9, 32.1, 31.6, 24.7, 20.2, 14.6, 9.7, 3.3, 3.2. LCMS (ESI): Mass calculated for C23H30NO5 [M+H]+: 400.2046, Found 400.2040

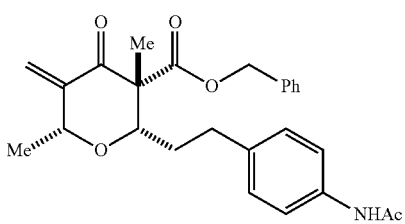

(±) benzyl (2S,3R,6R)-2-(4-acetamidophenethyl)-3,6-dimethyl-5-methylene-4-oxotetrahydro2H-pyran-3-carboxylate 1H NMR (500 MHz, Chloroform-d) δ 7.31-7.26 (m, 4H), 7.10-7.05 (m, 1H), 7.04-7.01 (m, 1H), 6.98-6.90 (m, 3H), 6.14 (d, J=2.1 Hz, 1H), 5.37 (d, J=2.1 Hz, 1H), 5.20-5.03 (m, 2H), 4.42-4.33 (m, 1H), 4.03-3.94 (m, 1H), 2.87-2.46 (m, 2H), 2.15 (s, 3H), 1.89-1.66 (m, 2H), 1.45 (d, J=6.3 Hz, 3H), 1.32 (s, 3H). 13C NMR (126 MHz, CDCl3) δ 197.2, 170.5, 168.1, 144.3, 137.3, 135.8, 135.6, 128.9, 128.5, 128.3, 128.2, 122.6, 119.9, 77.9, 74.7, 66.9, 60.9, 32.1, 31.6, 24.6, 20.2, 14.6. LCMS (ESI): Mass calculated for C26H30NO5 [M+H]+: 436.2046, Found 436.2061

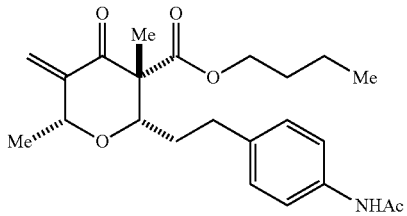

(±) butyl (2S,3R,6R)-2-(4-acetamidophenethyl)-3,6-dimethyl-5-methylene-4-oxotetrahydro2H-pyran-3-carboxylate 1H NMR (500 MHz, Chloroform-d) δ 7.43-7.33 (m, 2H), 7.14-7.05 (m, 2H), 6.18-6.11 (m, 1H), 5.40-5.32 (m, 1H), 4.15-3.99 (m, 2H), 2.85-2.65 (m, 2H), 2.14 (s, 3H), 1.79-1.62 (m, 2H), 1.46 (d, J=6.2 Hz, 3H), 1.38-1.20 (m, 4H), 1.27 (d, J=32.3 Hz, 3H), 0.94-0.82 (m, 3H). 13C NMR (126 MHz, CDCl3) δ 197.5, 170.7, 168.1, 144.4, 137.4, 135.9, 129.0, 122.4, 119.9, 77.9, 74.7, 65.2, 60.9, 32.2, 31.6, 30.4, 24.6, 20.3, 19.0, 14.5, 13.7. LCMS (ESI): Mass calculated for C23H32NO5 [M+H]+: 402.2202, Found 402.2185

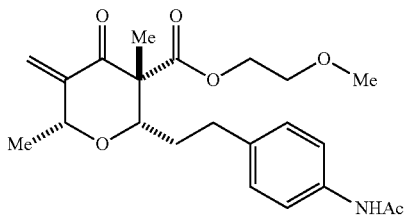

(±) 2-methoxyethyl (2S,3R,6R)-2-(4-acetamidophenethyl)-3,6-dimethyl-5-methylene-4oxotetrahydro-2H-pyran-3-carboxylate 1H NMR (500 MHz, Chloroform-d) δ 7.37 (d, J=3.9 Hz, 2H), 7.17-7.05 (m, 2H), 6.14 (d, J=2.1 Hz, 1H), 5.37 (d, J=2.1 Hz, 1H), 4.50-4.40 (m, 1H), 4.33-4.14 (m, 2H), 4.12-4.08 (m, 1H), 3.58-3.44 (m, 2H), 3.29 (s, 3H), 2.90-2.80 (m, 1H), 2.73-2.55 (m, 2H), 2.14 (s, 3H), 1.89-1.79 (m, 2H), 1.46 (d, J=6.3 Hz, 3H), 1.22 (s, 3H). 13C NMR (126 MHz, CDCl3) δ 197.3, 170.6, 168.1, 144.2, 137.5, 135.8, 129.0, 122.6, 120.0, 78.0, 77.2, 74.7, 70.2, 64.0, 60.9, 58.9, 32.1, 31.7, 24.7, 20.2, 14.5. LCMS (ESI): Mass calculated for C22H30NO6 [M+H]+: 404.1995, Found 404.2001

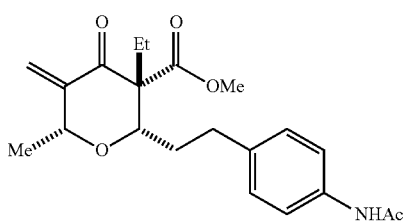

(±) methyl (2S,3R,6R)-2-(4-acetamidophenethyl)-3-ethyl-6-methyl-5-methylene-4oxotetrahydro-2H-pyran-3-carboxylate 1H NMR (500 MHz, Chloroform-d) δ 7.42-7.33 (m, 2H), 7.16 (d, J=7.6 Hz, 1H), 7.03 (d, J=8.0 Hz, 1H), 6.17 (d, J=2.2 Hz, 1H), 5.41 (d, J=2.2 Hz, 1H), 4.53-4.45 (m, 1H), 4.15-4.01 (m, 1H), 3.65 (s, 3H), 2.66 (dt, J=14.8, 8.4 Hz, 2H), 2.18 (s, 3H), 1.99-1.84 (m, 2H), 1.49 (d, J=6.3 Hz, 3H), 0.99-0.91 (m, 6H). 13C NMR (126 MHz, CDCl3) δ 197.8, 171.5, 168.5, 142.9, 138.4, 129.5, 124.7, 123.1, 120.3, 117.7, 78.3, 75.0, 61.3, 52.7, 32.6, 30.1, 25.1, 20.6, 14.9, 14.8. LCMS (ESI): Mass calculated for C21H28NO5 [M+H]+: 374.1967, Found 374.1962

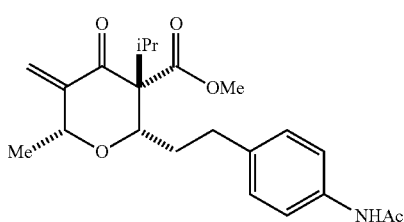

(±) methyl (2S,3R,6R)-2-(4-acetamidophenethyl)-3-isopropyl-6-methyl-5-methylene-4oxotetrahydro-2H-pyran-3-carboxylate 1H NMR (500 MHz, Chloroform-d) δ 7.36-7.29 (m, 2H), 7.12 (d, J=7.6 Hz, 1H), 6.99 (d, J=8.0 Hz, 1H), 6.13 (d, J=2.2 Hz, 1H), 5.37 (d, J=2.2 Hz, 1H), 4.47-4.40 (m, 1H), 4.09-43.99 (m, 1H), 3.61 (s, 3H), 2.61 (dt, J=14.8, 8.4 Hz, 2H), 2.14 (s, 3H), 1.92-1.80 (m, 2H), 1.45 (d, J=6.3 Hz, 3H), 0.93-0.86 (m, 3H). 13C NMR (126 MHz, CDCl3) δ 197.5, 171.3, 168.3, 142.7, 138.1, 129.1, 124.5, 122.9, 120.1, 117.6, 78.1, 74.9, 61.1, 52.6, 32.3, 29.9, 24.9, 20.4, 14.8, 14.7. LCMS (ESI): Mass calculated for C22H30NO5 [M+H]+: 388.2123, Found 388.2110

Correlation Analysis Between Binding Energy and $IC_{50}$ Values for 1st Generation Library The binding energies and $IC_{50}$ of all compounds in Table 1 and Table 2 that demonstrated the ability to inhibit telomerase activity by TRAP assay <100 μM were analyzed to see if a correlation existed between binding energies and $IC_{50}$. Linear regression alysis demonstrated that a positive correlation was observed, with an $R^2$=0.8069.

2nd Generation Library Subset

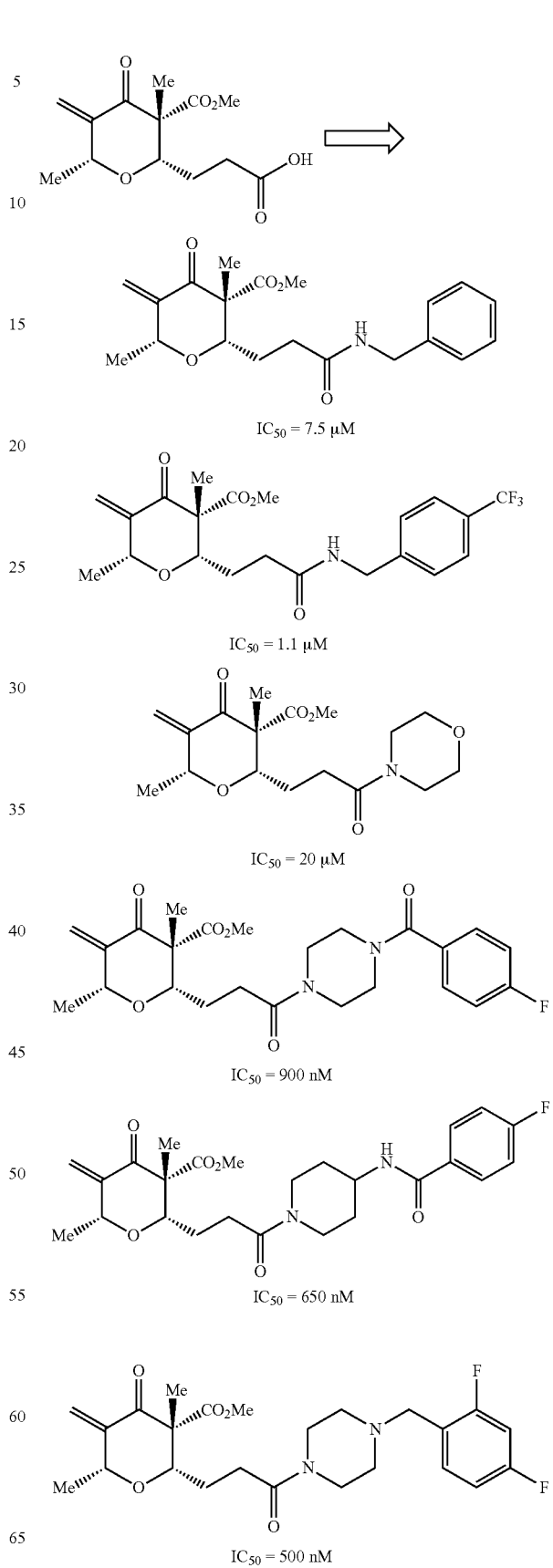

69
-continued
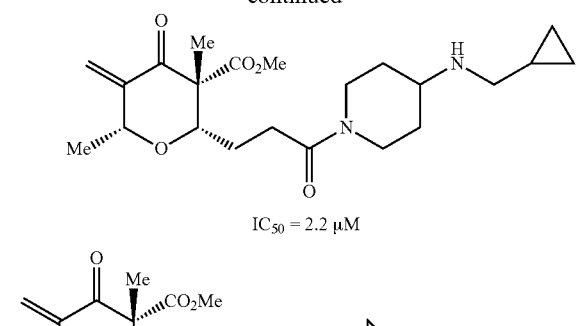
IC$_{50}$ = 2.2 µM
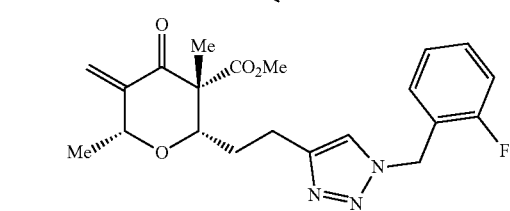
IC$_{50}$ = 300 nM
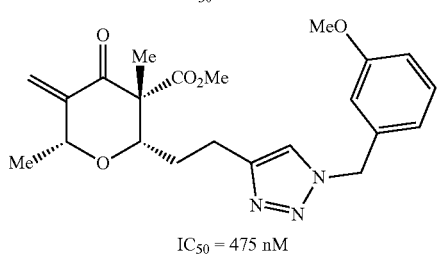
IC$_{50}$ = 475 nM
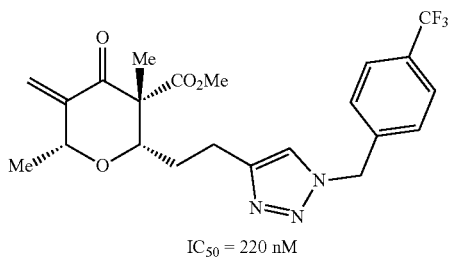
IC$_{50}$ = 220 nM
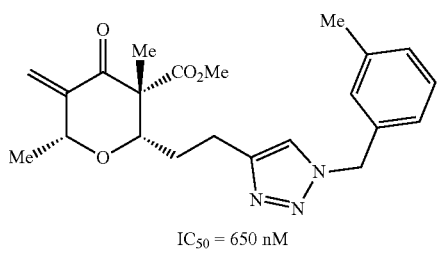
IC$_{50}$ = 650 nM
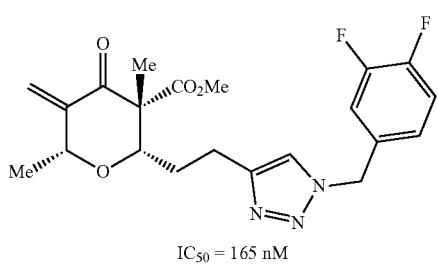
IC$_{50}$ = 165 nM
70
-continued
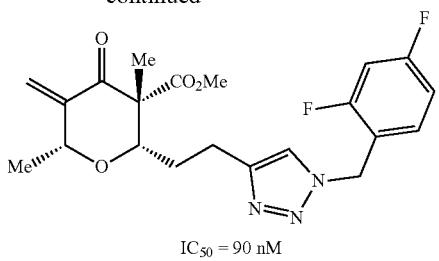
IC$_{50}$ = 90 nM
Synthesis of NU-1
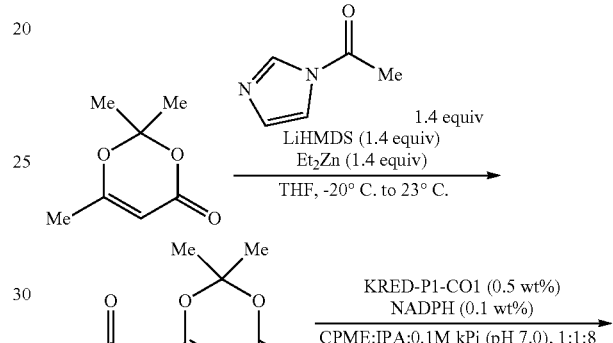

-continued

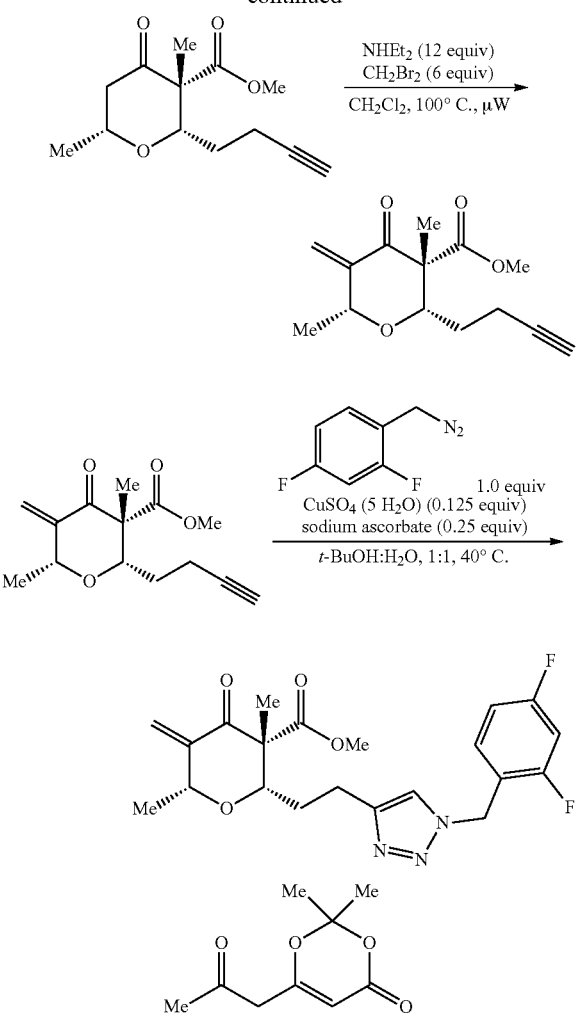

2,2-Dimethyl-6-(2-oxo-2-methylethyl)-4H-1,3-dioxin-4-one (S1)

Prepared according to literature precedent. 2 Dioxinone (1.0 equiv) in THF (2.0 M) was added dropwise to LiHMDS in THF (1.4 equiv, 1.0 M) and THF (1.0 M) at −20° C., and after 45 min, diethylzinc in hexanes (1.4 equiv, 1.0 M) was added over 2 h. After a further 30 min, the reaction mixture was allowed to warm up to −10° C. and N-acetylimidazole (1.4 equiv) was added portionwise over 15 min. After 3.5 h, H2O:THF (1:9; 75 mL) was added dropwise, followed by 6.0 M HCl (100 mL) and EtOAc (250 mL). The pH was adjusted to pH 1-2 using 1.0 M HCl (265 mL), and the layers were separated. The aqueous layer was extracted with EtOAc (250 mL), and the combined organic extracts were washed with brine (250 mL), dried (MgSO4), rotary evaporated, and chromatographed (hexanes:EtOAc 3:2) to give S1 as pale yellow crystals.

Analytical Data: 1H NMR spectroscopy (500 MHz, CDCl3) δ 5.35 (s, 1H), 3.37 (s, 2H), 2.25, (s, 3H), 1.72 (s, 6H); 13C NMR spectroscopy (125 MHz, CDCl3) δ 200.9, 164.4, 160.7, 107.2, 96.6, 47.9, 30.2, 25.0. All physical data for this product correspond with literature values.3

(R)-6-(2-hydroxypropyl)-2,2-dimethyl-4H-1,3-dioxin-4-one (S2)

Prepared according to literature precedent.4 160 mL of 0.1 M phosphate buffer (pH 7.0) was added to a 500 mL 3 neck round bottom flask equipped with an overhead stirrer, a nitrogen inlet, and a septum. 100 mg of KRED-P01-C01 was then added followed by 50 mg of NADPH. In a separate 100 mL round bottom flask, 20.0 g of S1, 20 mL isopropanol (IPA), and 20 mL cyclopentylmethyl ether (CPME) were added. Upon the β-ketodioxinone substrate completely dissolving (required slight heating and stirring), this solution was added to the solution containing KRED-P01-C01. The reaction was stirred for 72 hours at 30° C. Upon reaction completion, solid NaCl was added to the reaction mixture. The solution was then filtered, extracted with ethyl acetate (5×150 mL), dried over MgSO4, filtered, and concentrated in vacuo to obtain >99% pure β-hydroxydioxinone S2

Analytical Data: 1H NMR spectroscopy (500 MHz, CDCl3) δ 5.33 (s, 1H), 4.16-4.08 (m, 1H), 2.38 (1H, d, J=2.8), 2.37 (s, 1H), 1.70 (s, 6H), 1.27 (3H, d, J=6.2). 13C NMR spectroscopy (125 MHz, CDCl3) δ 169.3, 161.3, 106.6, 94.9, 65.1, 43.2, 25.2, 24.9, 23.5.

All physical data for this product corresponds with literature values.3

(5S,7R)-5-(but-3-yn-1-yl)-2,2,7-trimethyl-7,8-dihydro-4H,5H-pyrano[4,3-d][1,3]dioxin-4 one (S3)

A flask was charged with 4 Å MS (2:1 by wt), pent-4-ynal (4.0 equiv) and S2 (1.0 equiv). Dichloromethane (0.25 M) was added and the reaction was cooled to −78° C. Then, TMS OTf (2.0 equiv) was added dropwise and stirred for 5 h. The reaction was quenched at −78° C. with a 1:1 mixture of NEt3/MeOH and allowed to warm to room temperature. The suspension was then filtered through a Biotage Isolute phase separator and then concentrated. The crude product was of sufficient purity and immediately used in the next reaction.

methyl (2S,3R,6R)-2-(but-3-yn-1-yl)-6-methyl-4-oxotetrahydro-2H-pyran-3-carboxylate (S4)

In a microwave vial S3 (1.0 equiv) was dissolved in toluene (0.2 M). Dry methanol (10 equiv) was added, the reaction vial was capped, and the reaction heated in a Biotage microwave reactor at 150° C. for 40 m. After the vial was cooled to room temperature, the solution was concentrated. The crude product was of sufficient purity and was immediately used in the next reaction.

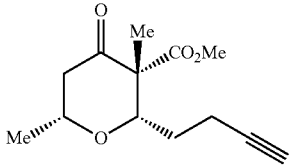 [SMILES: C#CCC[C@@H]1O[C@H](C)CC(=O)[C@]1(C)C(=O)OC]

methyl (2S,3R,6R)-2-(but-3-yn-1-yl)-3,6-dimethyl-4-oxotetrahydro-2H-pyran-3-carboxylate (S5)

S4 (1.0 equiv) was dissolved in acetonitrile (0.2 M) in a vial with stir bar. To the solution was added potassium carbonate (4 equiv) and methyl iodide (10 equiv). The reaction mixture was heated to 70° C. for 2 hours before cooling to room temperature and quenching with saturated aqueous NH4Cl. The mixture was diluted with CH2Cl2, filtered through a Biotage Isolute phase separator, and concentrated. The crude product was of sufficient purity and immediately used in the next reaction.

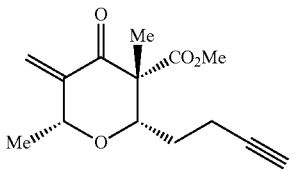 [SMILES: C#CCC[C@@H]1O[C@H](C)C(=C)C(=O)[C@]1(C)C(=O)OC]

methyl (2S,3R,6R)-2-(but-3-yn-1-yl)-3,6-dimethyl-5-methylene-4-oxotetrahydro-2H-pyran-3 carboxylate (S6)

Prepared according to literature precedent.5 To a solution of S5 (1.0 equiv) in CH2Cl2 (0.2 M) in a microwave vial, CH2Br2 (6.0 equiv) and Et2NH (12.0 equiv) were added. The container was sealed, and the reaction heated in a Biotage microwave reactor at 100° C. for 1 hour. After the vial was cooled to room temperature, the reaction solution was concentrated. Diethyl ether was added to the crude reaction mixture to precipitate out the ammonium salts. The mixture was filtered, and the filtrate was concentrated. The crude product was of sufficient purity and immediately used in the next reaction.

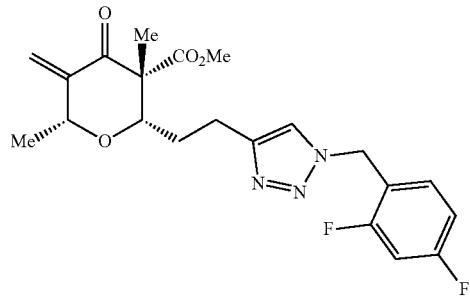 [SMILES: C=C1C(=O)[C@](C)(C(=O)OC)[C@H](CCc2cn(Cc3ccc(F)cc3F)nn2)O[C@@H]1C]

methyl (2S,3R,6R)-2-(2-(1-(2,4-difluorobenzyl)-1H-1,2,3-triazol-4-yl)ethyl)-3,6-dimethyl-5 methylene-4-oxotetrahydro-2H-pyran-3-carboxylate (NU-1)

1-(Azidomethyl)-2,4-difluorobenzene (1.0 equiv) and S6 (1.0 equiv) were dissolved in tBuOH (0.2 M) room temperature. To this, a solution of copper (II) sulfate pentahydrate (0.12 equiv) and sodium (R)-2-((S)-1,2-dihydroxyethyl)-4-hydroxy-5-oxo-2,5-dihydrofuran-3-olate (0.25 equiv) in water (0.2 M) was added. The reaction mixture was stirred at 40° C. for 5 h. After completion, the reaction mixture was extracted with EtOAc (3×). The organic layer was dried over sodium sulfate, and the excess solvent was removed under reduced pressure.

The crude product was purified by column chromatography to yield NU-1.

1H NMR (500 MHz, Chloroform-d) δ 7.36-7.24 (m, 2H), 7.22-7.10 (m, 2H), 6.15 (d, J=2.1 Hz, 1H), 5.50 (s, 2H), 5.38 (d, J=2.1 Hz, 1H), 4.45-4.24 (m, 1H), 4.05 (dd, J=10.2, 2.0 Hz, 1H), 3.61 (s, 3H), 2.73-2.56 (m, 2H), 2.10-1.78 (m, 2H), 1.48-1.39 (m, 3H), 1.32 (s, 3H). 13C NMR (126 MHz, CDCl3) δ 197.2, 171.1, 163.5, 160.4, 144.2, 137.0, 136.8, 129.8 (d, J=3.5 Hz), 125.8, 115.2 (d, J=21.5 Hz), 103.6, 100.5, 77.8, 77.3, 77.0, 76.8, 74.7, 60.9, 52.8, 35.8, 32.3, 20.2, 14.5. LCMS (ESI): Mass calculated for C21H24F2N3O4 [M+H]+ 420.1657, Found 420.1650

REFERENCES (1) Perrin, D. D.; Armarego, W. L. F., Purification of Laboratory Chemicals. 3rd ed.; Pergamon Press: Oxford, 1988.

(2) Patel, B. H.; Mason, A. M.; Patel, H.; Coombes, R. C.; Ali, S.; Barrett, A. G. M. Conversion of α-Amino Acids into Bioactive o-Aminoalkyl Resorcylates and Related Dihydroxyisoindolinones. J. Org. Chem. 2011, 76, 6209-6217.

(3) Fang, Z.; Clarkson, G. J.; Wills, M. Asymmetric reduction of 2,2-dimethyl-6-(2 oxoalkyl/oxoaryl)-1,3-dioxin-4-ones and application to the synthesis of (+)-yashabushitriol.
Tetrahedron Lett. 2013, 54, 6834-6837.

(4) Betori, R. C.; Miller, E. R.; Scheidt, K. A. A Biocatalytic Route to Highly Enantioenriched β Hydroxydioxinones. Adv. Synth. Catal. 2017, 359, 1131-1137.

(5) Hon, Y.-S.; Hsu, T.-R.; Chen, C.-Y.; Lin, Y.-H.; Chang, F.-J.; Hsieh, C.-H.; Szu, P.-H. Dibromomethane as one-carbon source in organic synthesis: microwave-accelerated α-methylenation of ketones with dibromomethane and diethylamine. Tetrahedron 2003, 59, 1509-1520.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having a formula selected from the following formula or a salt or hydrate thereof:

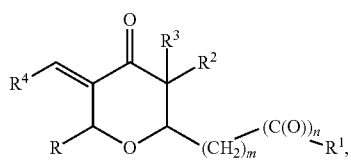

wherein:

R is selected from hydrogen, alkyl, cycloalkyl, aryl, or alkyl(aryl), and R is optionally substituted at one or more positions with halogen;

m is selected from 1-3;

n is 0 or 1;

$R^1$ is selected from hydrogen, alkyl, cycloalkyl, aryl, alkyl(aryl), aldehyde, carboxyalkyl, alkynyl, or hydroxyl; or $R^1$ has a formula selected from —NH-aryl, —NH-diaryl, or —NH-alkyl(aryl), optionally wherein $R^1$ is substituted at one or more positions with alkyl, alkoxy, hydroxyl, halogen, or haloalkyl; or $R^1$ has a formula selected from

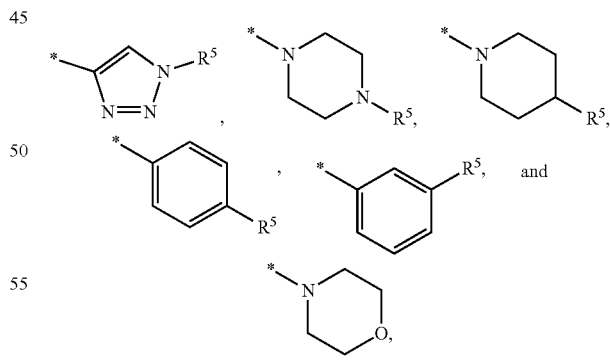

wherein $R^5$ is selected from hydrogen, alkyl, or benzyl, or $R^5$ has a formula selected from —C(O)—NH$_2$, —C(O)—NH-alkyl, —C(O)-phenyl, —C(O)—NH-phenyl, —C(O)—NH-benzyl, —CH$_2$—NH-phenyl, —NH—C(O)-phenyl, —NHAc, —N-alkyl-cycloalkyl, —O-phenyl, —O-benzyl, and $R^5$ optionally is substituted at one or more positions with alkyl, alkoxy, hydroxyl, halogen, and haloalkyl;

$R^2$ is —C(O)—O—$R^6$, wherein $R^6$ is selected from alkyl, cycloalkyl, alkyl(cycloalkyl), aryl, alkyl(aryl), and alkyl(alkoxy);

$R^3$ is hydrogen or alkyl;

$R^4$ is hydrogen;

optionally, wherein at least one of R, $R^1$, $R^2$, $R^3$, and $R^4$ is not hydrogen.

2. The compound of claim 1, wherein R is selected from: —$CH_3$, —$CH_2$—$CH(CH_3)_2$, and —$CH_2$—$CH_2$-phenyl.

3. The compound of claim 1, wherein *$(CH_2)_m$—$(C(O))_n$—$R^1$ is selected from:

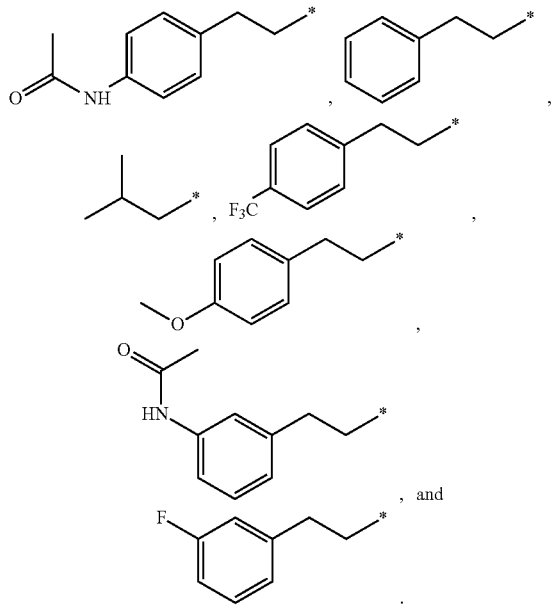

4. The compound of claim 1, wherein *$(CH_2)_m$—$(C(O))_n$—$R^1$ is

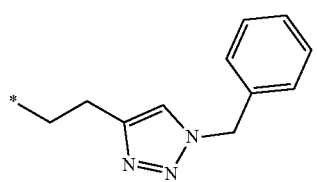 [SMILES: *CCc1cn(Cc2ccccc2)nn1]

and $R^1$ is optionally substituted at one or more positions with halogen.

5. The compound of claim 1, wherein $R^2$ is selected from: —C(O)—O—$CH_3$, —C(O)—O—$CH(CH_3)_2$, —C(0)—O—$(CH_2)_3$—$CH_3$.

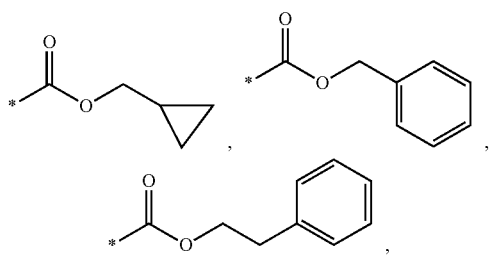

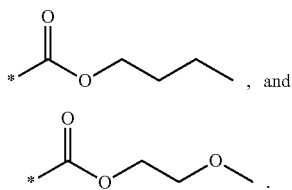

6. The compound of claim 1, wherein $R^3$ is selected from: —$CH_3$, —$CH_2$—$CH_3$, and —$CH(CH_3)_2$.

7. The compound of claim 1 having a formula selected from:

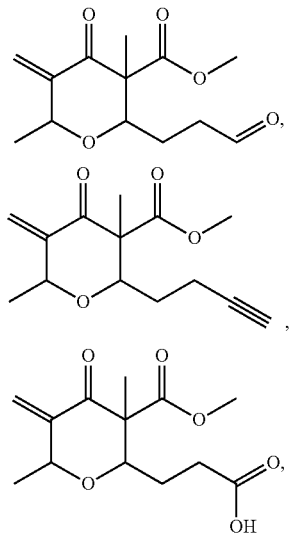

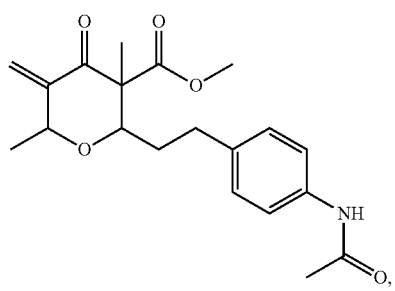

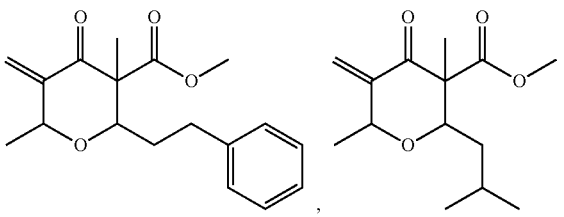

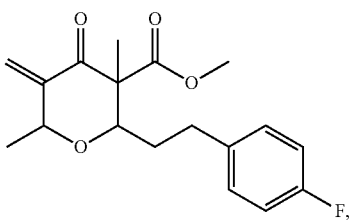

81
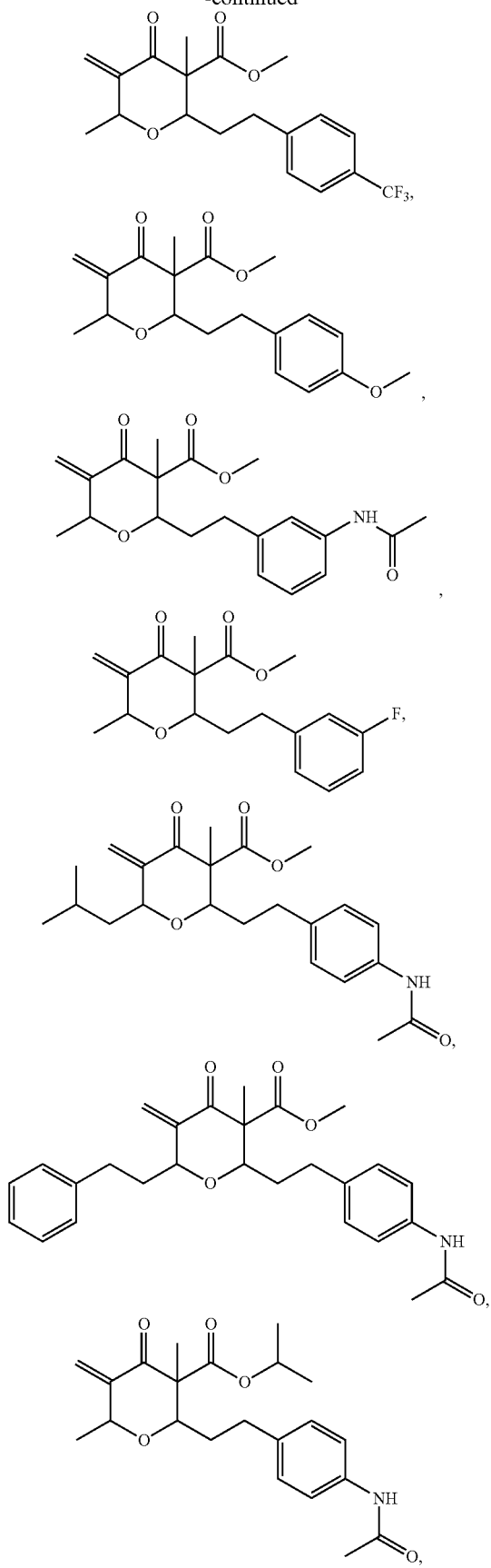
82
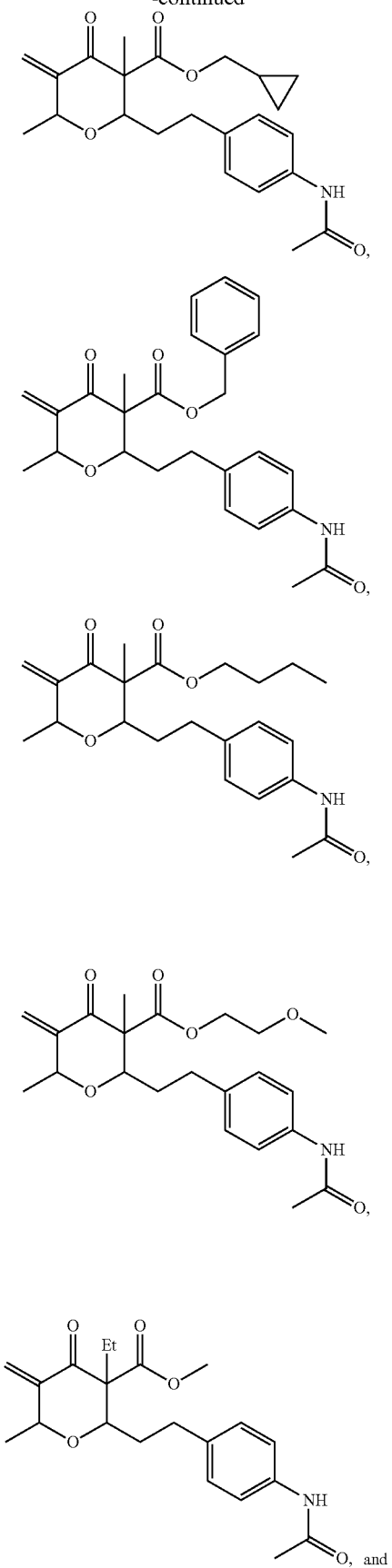

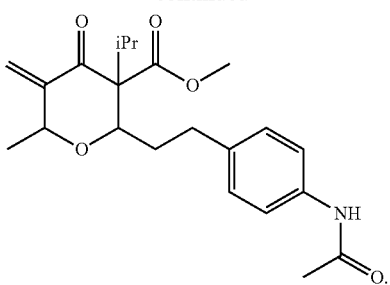
8. The compound of claim 1 having a formula selected from:
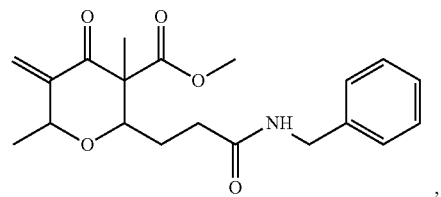
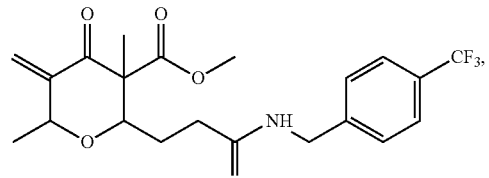
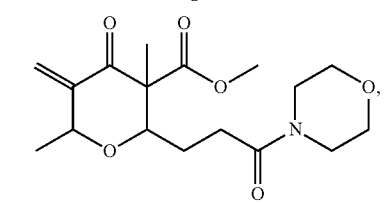
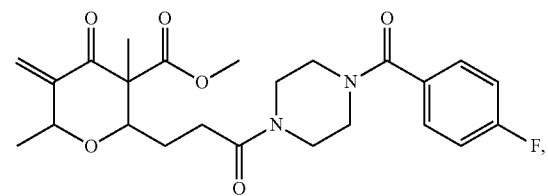
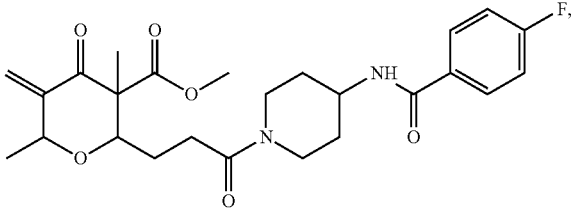
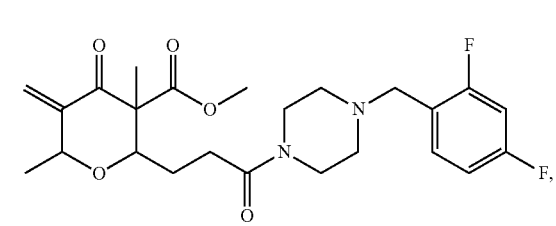
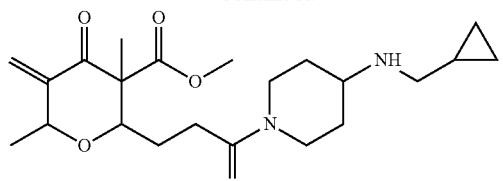
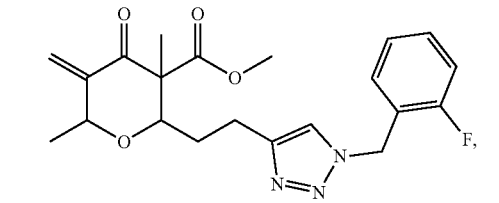
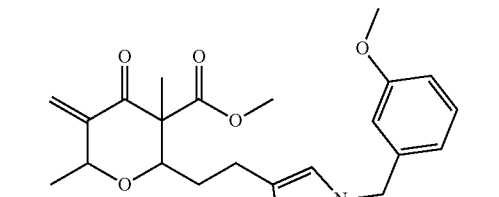
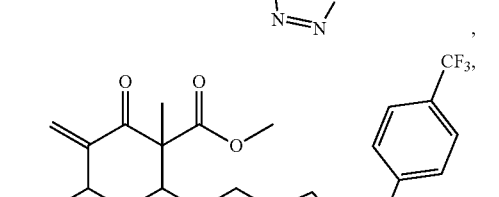
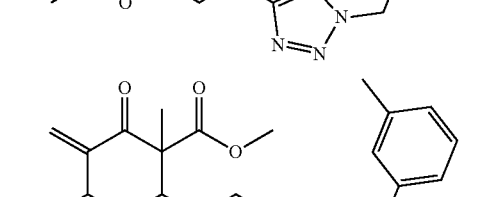
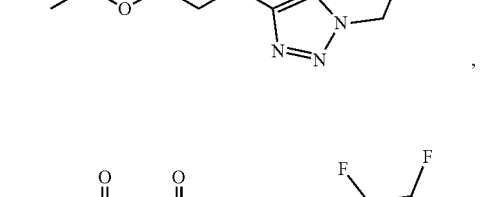
, and
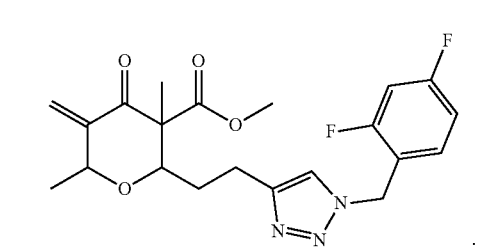

9. The compound of claim 1 having a formula selected from:

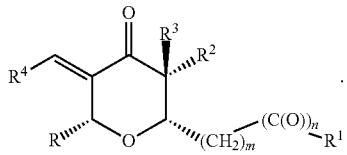

10. The compound of claim 1 having a formula selected from:

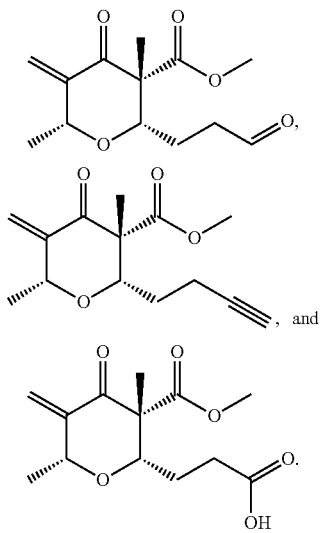

11. The compound of claim 1 having a formula:

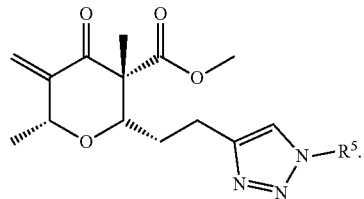

12. The compound of claim 1 having a formula:

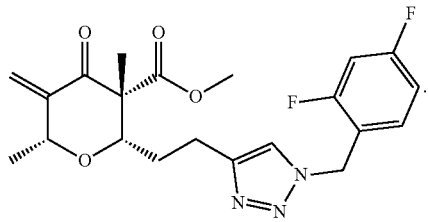 [SMILES: C=C1C(=O)[C@](C)(C(=O)OC)[C@H](CCc2cn(Cc3ccc(F)cc3F)nn2)O[C@@H]1C]

13. A pharmaceutical composition comprising an effective amount of the compound of claim 1 and a pharmaceutically acceptable carrier.

14. The compound of claim 1 having a formula selected from:

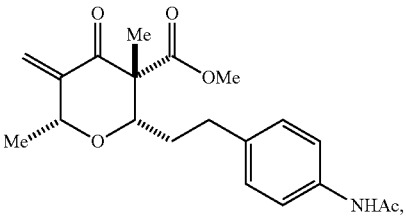

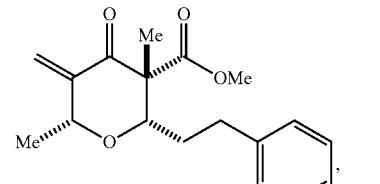

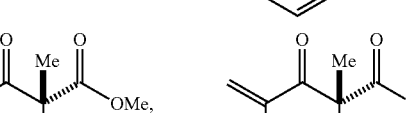

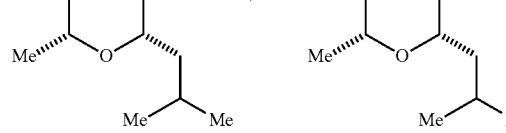

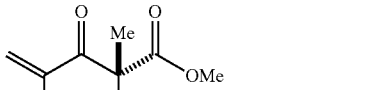

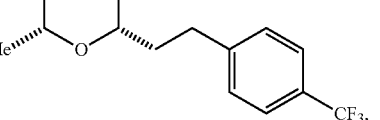

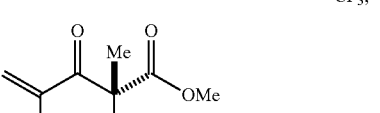

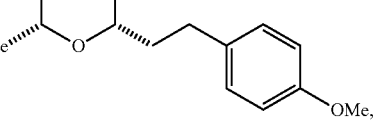

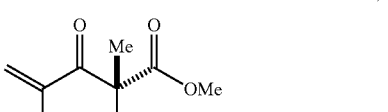

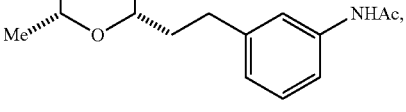

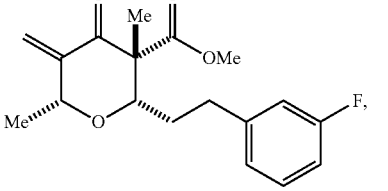

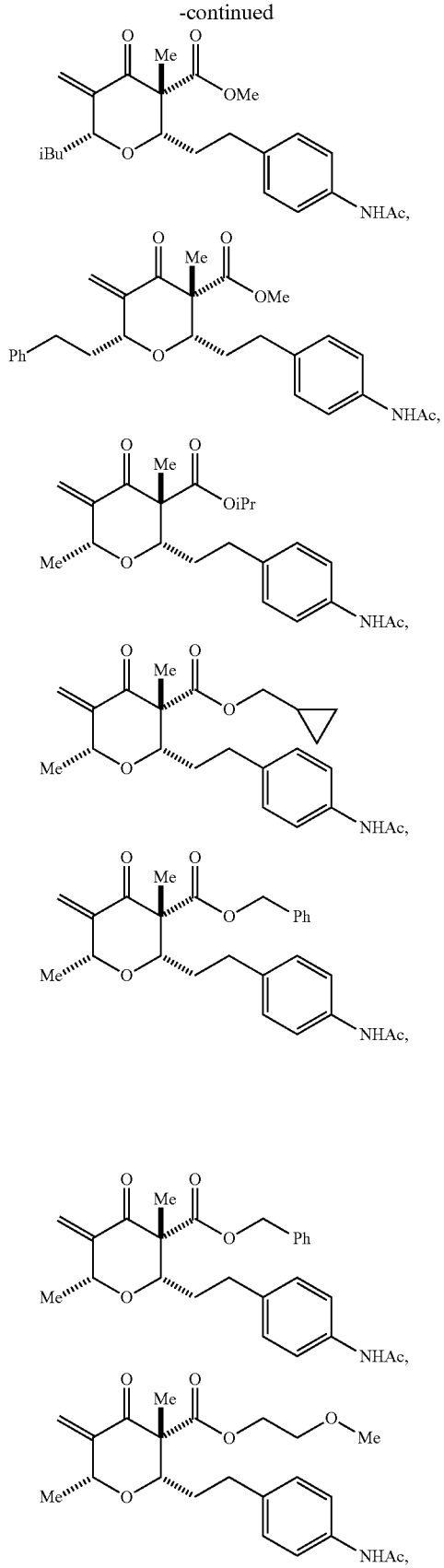
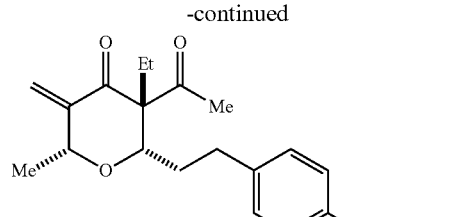
and
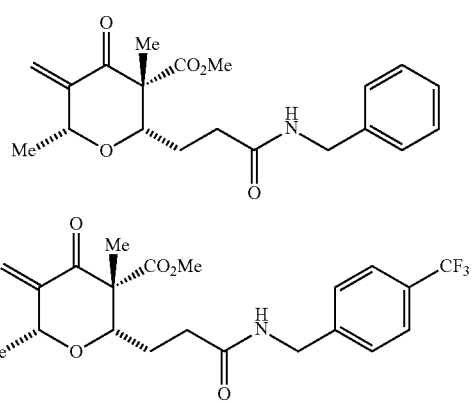
15. The compound of claim 1 having a formula selected from:
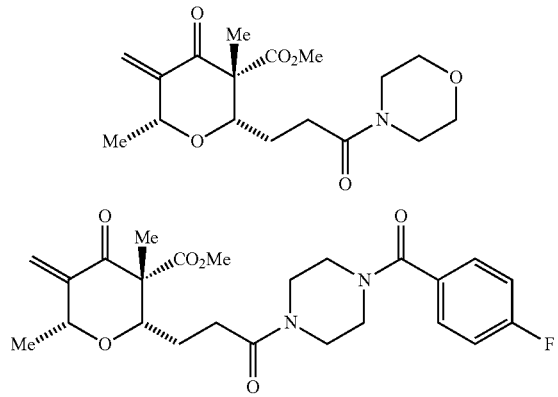
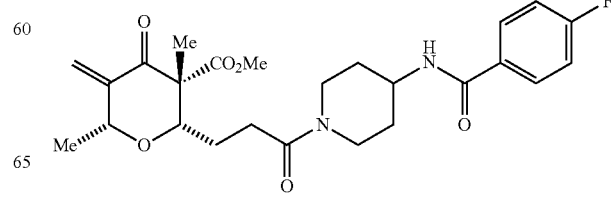

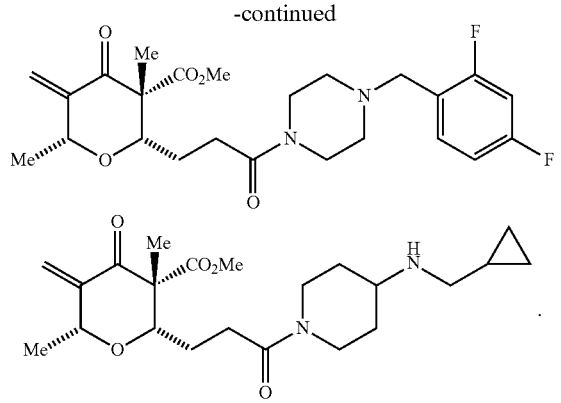
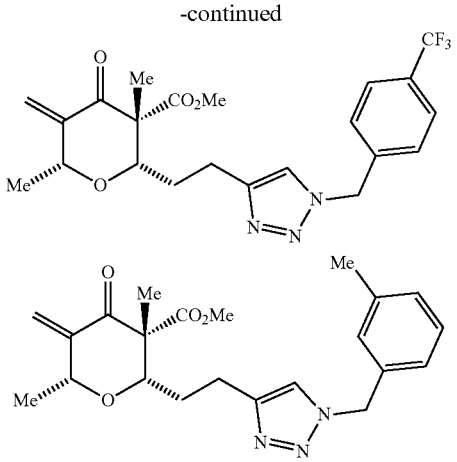
16. The compound of claim 1 having a formula selected from:
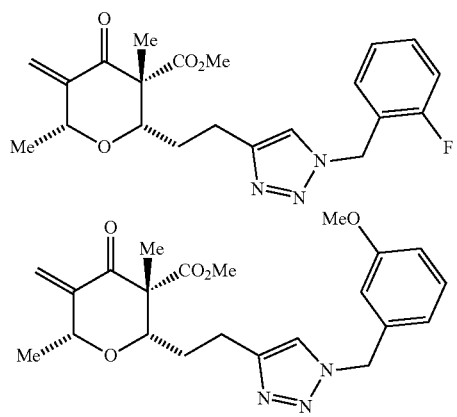
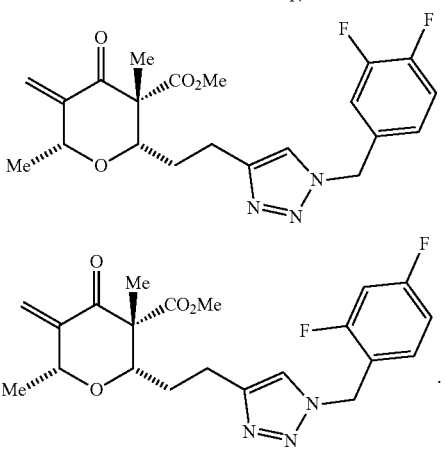
* * * * *

```
                        SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: synthetic

<400> SEQUENCE: 1
ctagacctgt catcattagg gttagggtta ggg                                 33

<210> SEQ ID NO 2
<211> LENGTH: 11
<212> TYPE: PRT
<213> ORGANISM: Artificial Sequence
<220> FEATURE:
<223> OTHER INFORMATION: synthetic

<400> SEQUENCE: 2

His Pro Gln Asp Glu Ile Pro Tyr Cys Gly Lys
1               5                   10

<210> SEQ ID NO 3
<211> LENGTH: 30
<212> TYPE: DNA
<213> ORGANISM: Artificial Sequence
<220> FEATURE:
<223> OTHER INFORMATION: synthetic

<400> SEQUENCE: 3
ctagacctgt catcactaga cctgtcatca                                     30

<210> SEQ ID NO 4
<211> LENGTH: 10
<212> TYPE: DNA
<213> ORGANISM: Artificial Sequence
<220> FEATURE:
<223> OTHER INFORMATION: synthetic

<400> SEQUENCE: 4
aaucccaauc                                                           10

<210> SEQ ID NO 5
<211> LENGTH: 14
<212> TYPE: DNA
<213> ORGANISM: Artificial Sequence
<220> FEATURE:
<223> OTHER INFORMATION: synthetic

<400> SEQUENCE: 5
ttagggttag ggag                                                      14
```

```
<210> SEQ ID NO 6
<211> LENGTH: 22
<212> TYPE: DNA
<213> ORGANISM: Artificial Sequence
<220> FEATURE:
<223> OTHER INFORMATION: synthetic

<400> SEQUENCE: 6
ttagggttag ggttagggtt ag                                              22

<210> SEQ ID NO 7
<211> LENGTH: 15
<212> TYPE: PRT
<213> ORGANISM: Artificial Sequence
<220> FEATURE:
<223> OTHER INFORMATION: synthetic

<400> SEQUENCE: 7

His Pro Gln Asp Glu Ile Pro Tyr Cys Gly Lys Ile Phe Asn Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Pro Ala His Gly Leu Phe Pro Trp Cys Gly Leu Leu Leu Asp Thr
1               5                   10                  15
```